(12) United States Patent
Levitzki et al.

(10) Patent No.: US 7,172,749 B2
(45) Date of Patent: Feb. 6, 2007

(54) RADIOLABELED IRREVERSIBLE INHIBITORS OF EPIDERMAL GROWTH FACTOR RECEPTOR TYROSINE KINASE AND THEIR USE IN RADIOIMAGING AND RADIOTHERAPY

(75) Inventors: Alexander Levitzki, Jerusalem (IL); Eyal Mishani, Mevaseret Zion (IL); Giuseppina Ortu, Cambridge (GB); Iris Ben-David, Ashdod (IL); Yulia Rozen, Jerusalem (IL)

(73) Assignees: Yissum Research Development Company of the Hebrew University of Jerusalem, Jerusalem (IL); Hadasit Medical Research Services and Development Ltd., Jerusalem (IL)

( * ) Notice: Subject to any disclaimer, the term of this patent is extended or adjusted under 35 U.S.C. 154(b) by 200 days.

(21) Appl. No.: 10/659,747

(22) Filed: Sep. 11, 2003

(65) Prior Publication Data

US 2004/0265228 A1    Dec. 30, 2004

Related U.S. Application Data

(63) Continuation-in-part of application No. PCT/IL02/00199, filed on Mar. 12, 2002, which is a continuation-in-part of application No. 09/802,928, filed on Mar. 12, 2001, now Pat. No. 6,562,319.

(51) Int. Cl.
*A61K 51/00* (2006.01)

(52) U.S. Cl. .................... 424/1.81; 424/1.11; 424/1.65; 424/1.85; 424/1.89; 424/9.3; 424/9.37; 544/224; 514/247; 514/248

(58) Field of Classification Search ............... 424/1.11, 424/1.65, 1.81, 1.85, 1.89, 9.1, 9.3, 9.37, 424/9.4, 9.5, 9.6, 9.7, 9.8; 544/224, 242, 544/244, 245, 253; 514/247, 248
See application file for complete search history.

(56) References Cited

U.S. PATENT DOCUMENTS

| | | | |
|---|---|---|---|
| 5,760,041 A | | 6/1998 | Wissner et al. |
| 6,126,917 A | * | 10/2000 | Mishani et al. ............ 424/1.89 |
| 6,127,374 A | | 10/2000 | Bridges |
| 6,153,617 A | | 11/2000 | Bridges |
| 6,251,912 B1 | | 6/2001 | Wissner et al. |
| 6,562,319 B2 | * | 5/2003 | Mishani et al. ............ 424/1.81 |
| 2002/0128553 A1 | | 9/2002 | Mishani et al. |
| 2004/0265228 A1 | * | 12/2004 | Levitzki et al. ............ 424/1.11 |

FOREIGN PATENT DOCUMENTS

| | | |
|---|---|---|
| WO | WO 99/09016 | 2/1999 |
| WO | WO 02/073235 | 9/2002 |
| WO | WO 2004/046101 | 3/2004 |
| WO | WO 2005/023315 | 3/2005 |

OTHER PUBLICATIONS

Smaill et al. "Tyrosine Kinase Inhibitors. 17. Irreversible Inhibitors of the Epidermal Growth Factor Receptor: 4-(Phenylamino)Quinazoline- and 4-(Phenylamino)Pyrido[3,2-d]Pyrimidine-6-Acrylamides Bearing Additional Solubilizing Functions", Journal of Medicinal Chemistry, 43: 1380-1397, 2000. Compound 18, 25-27, Table 1.
Smaill et al. "Tyrosine Kinase Inhibitors. 15. 4-(Phenylamino)Quiazoline and 4-(Phenylamino)Pyrido[d]Pyrimidine Acrylamides as Irreversible Inhibitors of the ATP Binding Site of the Epidermal Growth Factor Receptor", Journal of Medicinal Chemistry, 42: 1802-1815, 1999.
Mishani et al. "Carbon-11 Labeling of -Dimethylamino-But-2-Enoic Acid [4-(Phenylamino)-Quinazolin-6-Yl]-Amides, A New Class of EGFR Irreversible Inhibitors", Journal of Labelled Compounds and Radiopharmaceuticals, 46(S1): S2, 2003. Abstract.
Ortu et al. "Labeled EGFR-TK Irreversible Inhibitor (ML03) In Vitro and In Vivo Properties, Potential as Pet Biomarker for Cancer and Feasibility as Anticancer Drug", International Journal of Cancer, 101: 360-370, 2002. Conclusion, p. 361, Col.1,§ 1, Fig.1.
Johnström et al. "Synthesis of [Methoxy-11C]PD153035, A Selective EGF Receptor Tyrosine Kinase Inhibitor", Journal of Labbelled Compounds and Radiopharmaceuticals, XLI: 623-629, 1998. p. 627, Fig.3.
Mishani et al. "Novel Carbon-11 Labeled 4-Dimethylamino-But-2-Enoic Acid [4-(Phenylamino)-Quinazoline-6-Yl]-Amides: Potential PET Bioprobes for Molecular Imaging of EGFR-Positive Tumors", Nuclear Medicine and Biology, 31(4): 469-476, 2004. P.474, Col.2, § 4—p. 475, Figs.2, 3.

* cited by examiner

Primary Examiner—Dameron L. Jones

(57) ABSTRACT

Radiolabeled epidermal growth factor receptor tyrosine kinase (EGFR-TK) irreversible inhibitors and their use as biomarkers for medicinal radioimaging such as Positron Emission Tomography (PET) and Single Photon Emission Computed Tomography (SPECT) and as radiopharmaceuticals for radiotherapy are disclosed.

135 Claims, 7 Drawing Sheets
(4 of 7 Drawing Sheet(s) Filed in Color)

Projections : 10-40 minutes post injection

FDG 　　　　[C-11]ML04

Bladder excretion

RADIOLABELED IRREVERSIBLE INHIBITORS OF EPIDERMAL GROWTH FACTOR RECEPTOR TYROSINE KINASE AND THEIR USE IN RADIOIMAGING AND RADIOTHERAPY

This is a continuation-in-part of PCT/IL02/00199, filed Mar. 12, 2002, which is a continuation-in-part of U.S. patent application Ser. No. 09/802,928, filed Mar. 12, 2001, now U.S. Pat. No. 6,562,319, issued May 13, 2003.

FIELD AND BACKGROUND OF THE INVENTION

The present invention relates to radiolabeled compounds and their use in radioimaging and/or radiotherapy. More particularly, the present invention relates to radiolabeled irreversible inhibitors of epidermal growth factor receptor tyrosine kinase (EGFR-TK) and their use as biomarkers for medicinal radioimaging such as Positron Emission Tomography (PET) and Single Photon Emission Computed Tomography (SPECT), and as radiopharmaceuticals for radiotherapy.

The use of radioactive nuclides for medicinal purposes is well known in the art. Biologically active compounds that bind to specific cell surface receptors or that in other ways modify cellular functions have received some consideration as radiopharmaceuticals, and therefore, when labeled with a radioactive nuclide, such compounds are used as biospecific agents in radioimaging and radiotherapy.

Positron Emission Tomography (PET), a nuclear medicine imagine technology which allows the three-dimensional, quantitative determination of the distribution of radioactivity within the human body, is becoming an increasingly important tool for the measurement of physiological, biochemical, and pharmacological function at a molecular level, both in healthy and pathological states. PET requires the administration to a subject of a molecule labeled with a positron-emitting nuclide (radiotracer) such as $^{15}$O, $^{13}$N, $^{11}$C and $^{18}$F, which have half-lives of 2, 10, 20, and 110 minutes, respectively.

Single Photon Emission Computed Tomography (SPECT) is a form of chemical imaging in which emissions from radioactive compounds, labeled with gamma-emitting radionuclides, are used to create cross-sectional images of radioactivity distribution in vivo. SPECT requires the administration to a subject of a molecule labeled with a gamma-emitting nuclide such as $^{99m}$Tc, $^{67}$Ga, $^{111}$In and $^{123}$I.

Polypeptides such as growth factors, differentiation factors, and hormones often mediate their pleiotropic actions by binding to and activating cell surface receptors with an intrinsic intracellular protein tyrosine kinase activity. Epidermal growth factor receptor-tyrosine kinase (EGFR-TK) is over is expressed in breast cancer and other neoplasia. A suitable radiotracer that binds to EGFR-TK might allow, through a nuclear medicine imaging technique such as PET and SPECT, the mapping and quantification of this receptor-kinase. This would allow the study of changes in levels of expression of this receptor, including the monitoring of response to hormonal or other chemotherapy, and could lead to better patient management and differentiation in regard to therapeutic course of action.

Moreover, such radiotracer that comprises a suitable radioactive nuclide can be further used as an EGFR-TK biospecific agent for radiotherapy.

Recently, $^{99m}$Tc-labeled anti EGFR antibody was synthesized and biodistribution and dosimetry studies were performed in humans [1, 2]. However this labeled antibody, similar to other protein radiopharmaceuticals, has high and prolonged retention of radioactivity in the liver which constitutes a major problem for clinical applications. Furthermore, the researchers found that it was difficult to obtain accurate quantification of activity in tumors within normal organs because of varying background activities, particularly in lung lesions where fluid and atelectasis could not be differentiated from tumor.

EGF itself has been labeled for nuclear medicine imaging with gamma emitting nuclides including $^{99m}$Tc [3, 4] and indium-111 [5, 6), and the positron-emitting nuclide bromine-76 [7, 8]. The biodistribution in normal rats of the latter, bromine-76 EGF (murine), was reported [8], but no other in vivo studies in laboratory animals or humans have been reported.

4-Anilinoquinazolines, also referred to herein as 4-(phenylamino)quinazolines, have been shown to potently and selectively inhibit EGFR-TK activity by binding reversibly to an inner membrane ATP binding site on EGFR-TK, the prototype for such compounds being the small-molecules PD 153035 [9] and AG 1478 [10]. A report of a radioiodinated analog of PD 153035 including in vitro binding studies in MDA-486 cells has been presented [11].PD 153035 labeled with carbon-11 in the 6,7-methoxy groups has been evaluated in rats implanted with human neuroblastoma xenografts (SH-SY5Y) but specific uptake was not determined in a blocking study [12]. PD 153035 was also labeled with carbon-11 specifically in the 7-methoxy position and biodistribution experiments were performed in normal mice, but uptake specificity could not be demonstrated as administration of an enzyme-blocking dose of PD 153035 caused an increase in tracer uptake in the tissues studied [13]. The same abstract reported the labeling of the 7-(2-fluoroethoxy) PD 153035 analog with fluorine-18, but no biological experiments with this tracer were described. Additionally, the 2-$^{18}$F-fluoroethyl group might be subject to a high rate of $^{18}$F-hydrogen fluoride elimination to give the corresponding alkene ether, potentially resulting in high uptake of fluorine-18 in bone, giving poor in vivo images. Further, these ultra potent (IC$_{50}$<30 pM) inhibitors may only measure flow or permeability surface area rather than biochemical changes [14].

U.S. Pat. No. 6,126,917 teaches 4-(anilino)quinazoline derivatives, reversible inhibitors of EGFR-TK, labeled with fluorine-18 on the aniline ring. These compounds were tested in vitro, in vivo and by PET image analysis. While some of these compounds showed effective (reversible) inhibition activity in vitro, they were found to be ineffective as tracers for the imaging of EGFR-TK in vivo due to kinetic factors such as k$_{on}$ and k$_{off}$ and rapid blood clearance, as was fiber demonstrated by an animal PET comparative study between fluorine-18 FDG and these radiolabeled compounds. It is assumed that the discrepancy between the encouraging in vitro results and the discouraging in vivo results derives from the ATP competition at the compounds' binding site.

Thus, in order to achieve better imaging results, the non-specific binding of the radiolabeled compounds should be reduced. This can potentially be achieved by the use of derivatives of irreversible EGFR-TK inhibitors that are labeled with a positron-emitting nuclide. The irreversible binding of such compounds could potentially result in higher diagnostic performance. Furthermore, such irreversible inhibitors, when labeled with a suitable radioactive nuclide, can be used as effective radiotherapy agents as well, based on their high affinity toward, and irreversible binding to, tumor cells expressing EGFR-TK. Thus, such radiolabeled compounds that are targeted to the EGF receptor can bind preferentially to tumor cells and would lead to a high effective concentration of the radionuclides and therefore cause preferential cell killing at the site of the tumor.

Irreversible EGFR-TK inhibitors were recently described [15, 16, 19 and U.S. Pat. Nos. 6,153,617 and 6,127,374]. The irreversible binding thereof is achieved by 4-(anilino) quinazoline derivatives that are substituted at the 6 or 7 position of the quinazoline ring with an αβ-unsaturated carboxylic group, preferably an acrylamide group, which binds covalently to the Cys-773 at the EGFR-TK ATP binding site. Some of these compounds showed high potency toward EGFR inhibition in both in vitro and in vivo experiments. However, these compounds were not radiolabeled, and therefore cannot be used for radioimaging or radiotherapy.

There is thus a widely recognized need for, and it would be highly advantageous to have, radiolabeled irreversible inhibitors of EGFR-TK for use in radioimaging and radiotherapy.

SUMMARY OF THE INVENTION

According to the present invention there are provided novel radiolabeled compounds that are irreversible inhibitors of EGFR-TK and methods of using same in radioimaging and radiotherapy.

Thus, according to one aspect of the present invention there is provided a radiolabeled compound of a formula:

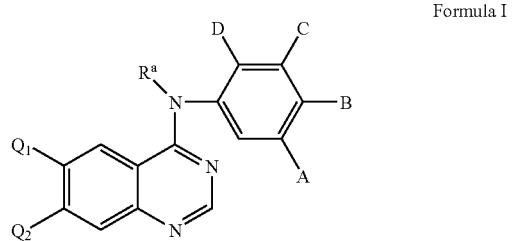

Formula I

Wherein:

Q1 is X—Y(=O)-Z and Q2 is selected from the group consisting of is hydrogen, halogen, alkoxy, hydroxy, thiohydroxy, thioalkoxy, alkylamino and amino, or Q1 is selected from the group consisting of hydrogen, halogen, alkoxy, hydroxy, thiohydroxy, thioalkoxy, alkylamino and amino and Q2 is X—Y(=O)-Z;

X is selected from the group consisting of —NR$^1$—, —O—, —NH—NR$^1$—, —O—NR$^1$—, NH—CHR$^1$—, —CHR$^1$—NH—, —CHR$^1$—O—, —O—CHR$^1$—, —CHR—CH$_2$— and —CHR$^1$—S— or absent;

Y is selected from the group consisting of a non-radioactive carbon and a radioactive carbon;

Z is selected from the group consisting of —R$^2$C=CR$^3$, —C≡C—R$^3$ and —R$^2$C=C=CHR$^3$;

R$^a$ is selected from the group consisting of hydrogen or alkyl having 1–8 carbon atoms;

A, B, C and D are each independently selected from the group consisting of hydrogen, a non-radioactive derivatizing group and a radioactive derivatizing group selected from a radioactive bromine, a radioactive iodine and a radioactive fluorine;

R$^1$ is selected from the group consisting of hydrogen and substituted or non-substituted alkyl having 1–6 carbon atoms;

R$^2$ is selected from the group consisting of hydrogen, halogen and alkyl having 1–6 carbon atoms; and R$^3$ is selected from the group consisting of hydrogen, halogen, carboxy, alkenyl, alkoxy, carbonyl, substituted or non-substituted alkyl having 1–6 carbon atoms and substituted or non-substituted phenyl;

provided that the compound comprises at least one radioactive atom.

According to further features in preferred embodiments of the invention described below, the non-radioactive derivatizing group is selected from the group consisting of hydrogen, halogen, alkyl, haloalkyl, hydroxy, alkoxy, carboxy, carbalkoxy, thiohydroxy, thiocarboxy, thioalkoxy, alkylsulfinyl, alkylsulfonyl, amino, diamino, carbamyl, dicarbamoyl, nitro and cyano.

According to still further features in the described preferred embodiments Q1 is X—Y(=O)-Z and Q2 is selected from the group consisting of hydrogen, halogen, alkoxy, hydroxy, thiohydroxy, thioalkoxy, alkylamino and amino.

According to still further features in the described preferred embodiments Q1 is X—Y(=O)-Z and Q2 is hydrogen.

According to still further features in the described preferred embodiments Q1 is X—Y(=O)-Z and Q2 is alkoxy.

According to still further features in the described preferred embodiments the alkoxy comprises a morpholino group.

According to still fixer features in the described preferred embodiments Q1 is X—Y(=O)-Z and Q2 is alkylamino. Preferably, the alkylamino comprises a piperazino group.

According to still further features in the described preferred embodiments X is —NR$^1$— and Z is —R$^2$C=CHR$^3$.

According to still further features in the described preferred embodiments each of R$^1$, R$^2$ and R$^3$ is hydrogen.

According to still further features in the described preferred embodiments R$^3$ is a substituted alkyl having 1–6 carbon atoms.

According to still further features in the described preferred embodiments the substituted alkyl comprises a radioactive atom.

According to still further features in the described preferred embodiments the substituted alkyl comprises a substituted amino group, e.g., an alkylamino group or a dialkylamino group.

According to still further features in the described preferred embodiments the substituted amino group comprises the radioactive atom.

According to still further features in the described preferred embodiments the radioactive atom is a radioactive carbon, preferably carbon-11.

According to still further features in the described preferred embodiments Y is a radioactive carbon.

According to still further features in the described preferred embodiments at least one of A, B, C and D is a radioactive fluorine.

According to still further features in the described preferred embodiments D is a radioactive fluorine.

According to still further features in the described preferred embodiments D is a radioactive fluorine, A and B are each chlorine and C is hydrogen.

According to still further features in the described preferred embodiments A is a radioactive bromine or a radioactive iodine.

According to still further features in the described preferred embodiments the radioactive carbon is carbon-11.

According to still further features in the described preferred embodiments Y is carbon-11, A and B are each chlorine, C is hydrogen and D is fluorine.

According to still further features in the described preferred embodiments Y is carbon-11, A is bromine or iodine and B, C and D are each hydrogen.

According to still further features in the described preferred embodiments the radioactive fluorine is fluorine-18.

According to still fixer features in the described preferred embodiments the radioactive bromine is bromine-76 or bromine-77.

According to still further features in the described preferred embodiments the radioactive iodine is iodine-123, iodine-124 or iodine-131, preferably iodine-124.

According to another aspect of the present invention there is provided a pharmaceutical composition comprising as an active ingredient the radiolabeled compound of the invention and a pharmaceutical acceptable carrier.

According to yet another aspect of the present invention there is provided a method of monitoring the level of epidermal growth factor receptor within a body of a patient comprising (a) administering to the patient the radiolabeled compound of the invention; and (b) employing a nuclear imaging technique for monitoring a distribution of the compound within the body or within a portion thereof.

According to further features in preferred embodiments of the invention described below, the technique is positron emission tomography or single photon emission computed tomography.

According to still another aspect of the present invention there is provided a method of radiotherapy comprising administering to a patient a therapeutically effective amount of the radiolabeled compound of the invention.

According to an additional aspect of the present invention there is provided a method of synthesizing a radiolabeled compound of a formula:

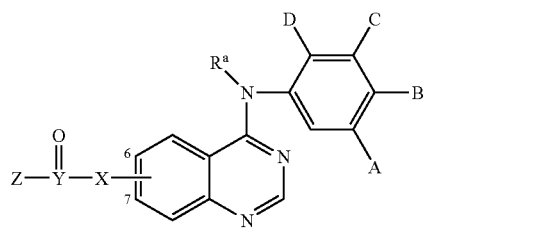

Formula II

Wherein:

X—Y(=O)-Z is at position 6 or 7 of the quinazoline ring;

X is selected from the group consisting of —NR$^1$—, —O—, —NH—NR$^1$—, —O—NR$^1$—, NH—CHR$^1$—, —CHR$^1$—NH—, —CHR$^1$—O—, —O—CHR$^1$—, —CHR$^1$—CH$_2$— and —CHR$^1$—S— or absent;

Y is carbon-11;

Z is selected from the group consisting of —R$^2$C=CHR$^3$, —C≡C—R$^3$ and —R$^2$C=C=CHR$^3$;

R$^a$ is selected from the group consisting of hydrogen or alkyl having 1–8 carbon atoms;

A, B, C and D are each independently selected from the group consisting of hydrogen and a non-radioactive derivatizing group;

R$^1$ is selected from the group consisting of hydrogen, and substituted or non-substituted alkyl having 1–6 carbon atoms;

R$^2$ is selected from the group consisting of hydrogen, halogen and alkyl having 1–6 carbon atoms; and R$^3$ is selected from the group consisting of hydrogen, halogen, carboxy, alkenyl, alkoxy, carbonyl, substituted or non-substituted alkyl having 1–6 carbon atoms and substituted or non-substituted phenyl.

The method comprising: (a) coupling an aniline derivatized by the R$^a$, A, B, C and D with a 4-chloroquinazoline substituted at position 6 and/or 7 by one or more reactive group(s), so as to produce a reactive 4-(phenylamino)quinazoline derivatized by the R$^a$, A, B, C and D; and (b) reacting the reactive 4-(phenylamino)quinazoline with a reactive carbon-11 labeled α,β-unsaturated carboxylic derivative.

According further features in preferred embodiments of the invention described below, the reactive 4-(phenylamino)quinazoline is 4-(phenylamino)-6-nitroquinazoline, and the method further comprising, prior to step (b), reducing the 4-(phenylamino)-6-nitroquinazoline so as to produce a 4-(phenylamino)-6-aminoquinazoline derivatized by A, B, C and D.

According to still further features in the described preferred embodiments the 4-chloroquinazoline is substituted at positions 6 and 7 by a first and a second reactive groups, the method flirter comprising, prior to step (c), reacting the reactive 4-(phenylamino)quinazoline with a chemically reactive group.

According to still further features in the described preferred embodiments the reactive carbon-11 labeled α,β-unsaturated carboxylic derivative is carbon-11 labeled acryloyl chloride.

According to yet an additional aspect of the present invention there is provided a method of synthesizing a radiolabeled compound of formula II as described hereinabove, wherein:

X—Y(=O)-Z is at position 6 or 7 of the quinazoline ring;

X is selected from the group consisting of —NR$^1$—, —O—, —NH—NR$^1$—, —O—NR$^1$—, NH—CHR$^1$—, —CHR$^1$—NH—, —CHR$^1$—O—, —O—CHR$^1$—, —CHR$^1$—CH$_2$— and —CHR$^1$—S— or absent;

Y is non-radioactive carbon;

Z is selected from the group consisting of —R$^2$C=CHR$^3$, —C≡C—R$^3$ and —R$^2$C=C=CHR$^3$;

R$^a$ is selected from the group consisting of hydrogen or alkyl having 1–8 carbon atoms;

A, B, C and D are each independently selected from the group consisting of (i) hydrogen, (ii) a non-radioactive derivatizing group; and (iii) fluorine-18, provided that at least one of A, B, C and D is fluorine-18;

R$^1$ is selected from the group consisting of hydrogen, and substituted or non-substituted alkyl having 1–6 carbon atoms;

R$^2$ is selected from the group consisting of hydrogen, halogen and alkyl having 1–6 carbon atoms; and R$^3$ is selected from the group consisting of hydrogen, halogen, carboxy, alkenyl, alkoxy, carbonyl, substituted or non-substituted alkyl having 1–6 carbon atoms and substituted or non-substituted phenyl.

The method comprising: (a) preparing a fluorine-18 labeled aniline derivatized by the R$^a$, A, B, C and D, wherein at least one of A, B, C and D is fluorine-18; (b) coupling the fluorine-18 labeled aniline derivatized by the R$^a$, A, B, C and D with 4-chloroquinazoline substituted at position 6 and/or 7 by one or more reactive group(s), so as to produce a reactive fluorine-18 labeled 4-(phenylamino))quinazoline derivatized by A, B, C and D; and (c) reacting the reactive fluorine-18 labeled 4-(phenylamino)quinazoline with a reactive α,β-unsaturated derivative, so as to produce a fluorine-18 labeled 4-(phenylamino)quinazoline substituted by an α,β-unsaturated group.

According to further features in preferred embodiments of the invention described below, the reactive fluorine-18 labeled 4-(phenylamino)-quinazoline is fluorine-18 labeled 4-(phenylamino)-6-nitroquinazoline and the method further comprising, prior to step (c), reducing the fluorine-18 labeled 4-(phenylamino)-6-nitroquinazoline so as to produce a fluorine-18 labeled 4-(phenylamino)-6-aminoquinazoline derivatized by A, B, C and D.

According to still farther features in the described preferred embodiments the 4-chloroquinazoline is substituted at positions 6 and 7 by a first and a second reactive groups and the method further comprising, prior to step (c), reacting the reactive fluorine-18 labeled 4-(phenylamino)quinazoline with a chemically reactive group.

According to still further features in the described preferred embodiments the reactive α,β-unsaturated carboxylic derivative is acryloyl chloride.

According to still further features in the described preferred embodiments $R^3$ is the substituted alkyl having 1–6 carbon atoms and the reactive α,β-unsaturated carboxylic derivative terminates with a reactive group, and the method further comprising reacting the fluorine-18 labeled 4-(phenylamino)quinazoline substituted by the α,β-unsaturated carboxylic group with a reactive substituted alkyl having 1–6 carbon atoms.

According to still an additional aspect of the present invention there is provided a method of synthesizing a radiolabeled compound of formula II as described hereinabove, wherein:

X—Y(═O)-Z is at position 6 or 7 of the quinazoline ring;

X is selected from the group consisting of —$NR^1$—, —O—, —NH—$NR^1$—, —O—$NR^1$—, NH—$CHR^1$—, —$CHR^1$—NH—, —$CHR^1$—O—, —O—$CHR^1$—, —$CHR^1$—$CH_2$— and —$CHR^1$—S— or absent;

Y is a non-radioactive carbon;

Z is selected from the group consisting of —$R^2$C═$CHR^3$, —C≡C—$R^3$ and —$R^2$C═C═$CHR^3$;

$R^a$ is selected from the group consisting of hydrogen or alkyl having 1–8 carbon atoms;

A, B, C and D are each independently selected from the group consisting of (i) hydrogen, (ii) a non-radioactive derivatizing group and (iii) a radioactive atom selected from a radioactive bromine and a radioactive iodine, provided that at least one of A, B, C and D is a radioactive bromine or a radioactive iodine;

$R^1$ is selected from the group consisting of hydrogen, and substituted or non-substituted alkyl having 1–6 carbon atoms;

$R^2$ is selected from the group consisting of hydrogen, halogen and alkyl having 1–6 carbon atoms; and $R^3$ is selected from the group consisting of hydrogen, halogen, carboxy, alkenyl, alkoxy, carbonyl, substituted or non-substituted alkyl having 1–6 carbon atoms and substituted or non-substituted phenyl.

The method comprising: (a) coupling an aniline derivatized by the $R^a$, A, B, C and D, wherein at least one of A, B, C and D is a halogen atom, with 4-chloroquinazoline substituted at position 6 and/or 7 by one or more reactive group(s), so as to produce a reactive 4-(phenylamino) quinazoline derivatized by A, B, C and D; (b) radiolabeling the reactive 4-(phenylamino)quinazoline derivatized by A, B, C and D with a radioactive bromine or a radioactive iodine, so as to produce a radioactive bromine labeled or a radioactive iodine labeled reactive 4-(phenylamino) quinazoline derivatized by A, B, C and D, wherein at least one of the A, B, C and D is a radioactive bromine or a radioactive iodine; and (c) reacting the radioactive bromine labeled or radioactive iodine labeled reactive 4-(phenylamino)quinazoline with a reactive α,β-unsaturated derivative.

According to further features in the preferred embodiments of the invention described below, the reactive 4-(phenylamino)-quinazoline is 4-(phenylamino)-6-nitroquinazoline and the method further comprising, prior to step (b), reducing the 4-(phenylamino)-6-nitroquinazoline, so as to produce a 4-(phenylamino)-6-aminoquinazoline derivatized by A, B, C and D, wherein at least one of the A, B, C and D is a halogen.

According to still further features in the described preferred embodiments the halogen is bromine.

According to still further features in the described preferred embodiments the 4-chloroquinazoline is substituted at positions 6 and 7 by a first and a second reactive groups and the method further comprising, prior to step (c), (e) reacting the reactive radioactive bromine labeled or radioactive iodine labeled 4-(phenylamino)quinazoline with a chemically reactive group.

According to still further features in the described preferred embodiments $R^3$ is the substituted alkyl having 1–6 carbon atoms, the reactive α,β-unsaturated carboxylic derivative terminates with a reactive group and the method further comprising reacting the radioactive bromine labeled or radioactive iodine labeled reactive 4-(phenylamino) quinazoline substituted by the α,β-unsaturated carboxylic group with a reactive substituted alkyl having 1–6 carbon atoms.

According to still further features in the described preferred embodiments the reactive α,β-unsaturated carboxylic derivative is 4-bromocrotonyl chloride. According to still further features in the described preferred embodiments the reactive substituted alkyl is dimethylamine.

According to still further features in the described preferred embodiments the chemically reactive group comprises a morpholinoalkoxy group.

According to a further aspect of the present invention, there is provided a method of synthesizing a radiolabeled compound of formula II as described hereinabove, wherein:

X—Y(═O)-Z is at position 6 or 7 of the quinazoline ring;

X is selected from the group consisting of —$NR^1$—, —O—, —NH—$NR^1$—, —O—$NR^1$—, NH—$CHR^1$—, —$CHR^1$—NH—, —$CHR^1$—O—, —O—$CHR^1$—, —$CHR^1$—$CH_2$— and —$CHR^1$—S— or absent;

Y is a non-radioactive carbon;

Z is selected from the group consisting of —$R^2$C═$CHR^3$, —C≡C—$R^3$ and —$R^2$C═C═$CHR^3$;

$R^a$ is selected from the group consisting of hydrogen or alkyl having 1–8 carbon atoms;

A, B, C and D are each independently selected from the group consisting of (i) hydrogen, (ii) a non-radioactive derivatizing group and (iii) a radioactive atom selected from a radioactive bromine and a radioactive iodine, provided that at least one of A, B, C and D is a radioactive bromine or a radioactive iodine;

$R^1$ is selected from the group consisting of hydrogen, and substituted or non-substituted alkyl having 1–6 carbon atoms;

$R^2$ is selected from the group consisting of hydrogen, halogen and alkyl having 1–6 carbon atoms; and R³ is substituted alkyl having 1–6 carbon atoms, which comprises a carbon-11 atom.

The method comprising: (a) coupling an aniline derivatized by R^a, A, B, C and D with a 4-chloroquinazoline substituted at position 6 or 7 by a first reactive group, so as to produce a reactive 4-(phenylamino)quinazoline derivatized by A, B, C and D; (b) reacting the reactive 4-(phenylamino)quinazoline with a reactive α,β-unsaturated carboxylic derivative, the reactive α,β-unsaturated carboxylic derivative terminating with a second reactive group, so as to produce a 4-(phenylamino)quinazoline substituted at position 6 or 7 by an α,β-unsaturated carboxylic group terminating with the second reactive group; (c) reacting the 4-(phenylamino)quinazoline substituted at position 6 or 7 by the α,β-unsaturated carboxylic group terminating with the second reactive group with a reactive substituted alkyl having 1–6 carbon atoms, so as to produce a 4-(phenylamino)quinazoline substituted at position 6 or 7 by the α,β-unsaturated carboxylic group terminating with the reactive substituted alkyl; and (d) reacting the 4-(phenylamino)quinazoline substituted at position 6 or 7 by the α,β-unsaturated carboxylic group terminating with the reactive substituted alkyl with a carbon-11 labeled reactive compound.

According to further features in preferred embodiments of the invention described below, the reactive 4-(phenylamino)quinazoline is 4-(phenylamino)-6-nitroquinazoline and the method further comprising, prior to step (b), reducing the 4-(phenylamino)-6-nitroquinazoline so as to produce a 4-(phenylamino)-6-aminoquinazoline derivatized by A, B, C and D.

According to still further features in the described preferred embodiments the reactive α,β-unsaturated carboxylic derivative is acryloyl chloride.

According to still further features in the described preferred embodiments the second reactive group is halogen.

According to still further features in the described preferred embodiments the halogen is selected from the group consisting of bromine and iodine.

According to still further features in the described preferred embodiments the reactive α,β-unsaturated carboxylic derivative terminating with the second reactive group is 4-bromocrotonyl chloride.

According to still further features in the described preferred embodiments the reactive substituted alkyl having 1–6 carbon atoms is methylamine.

According to still further features in the described preferred embodiments the carbon-11 labeled reactive compound is carbon-11 methyl iodide.

According to still further features in the described preferred embodiments the X—Y(=O)-Z group is at position 6 of the quinazoline ring.

The present invention successfully addresses the shortcomings of the presently known configurations by providing novel irreversible biomarkers for radioimaging and radiopharmaceuticals for radiotherapy.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars showing are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings

Figure 1:
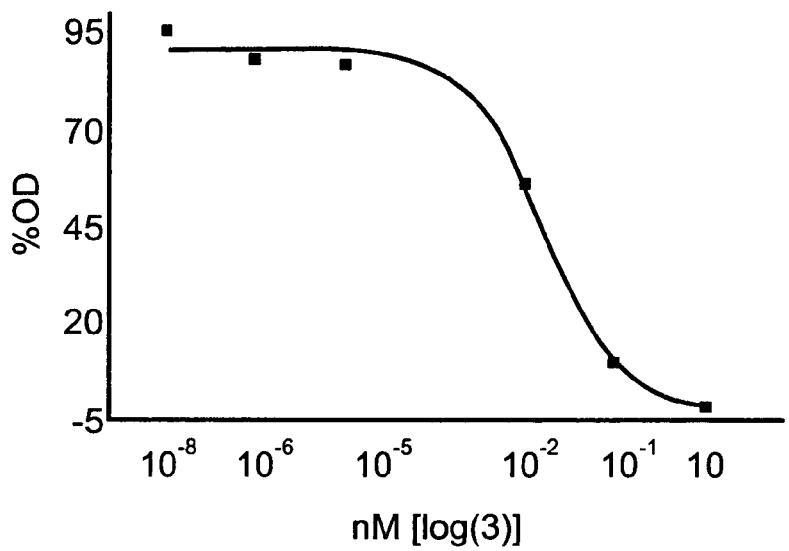
Figure 2:
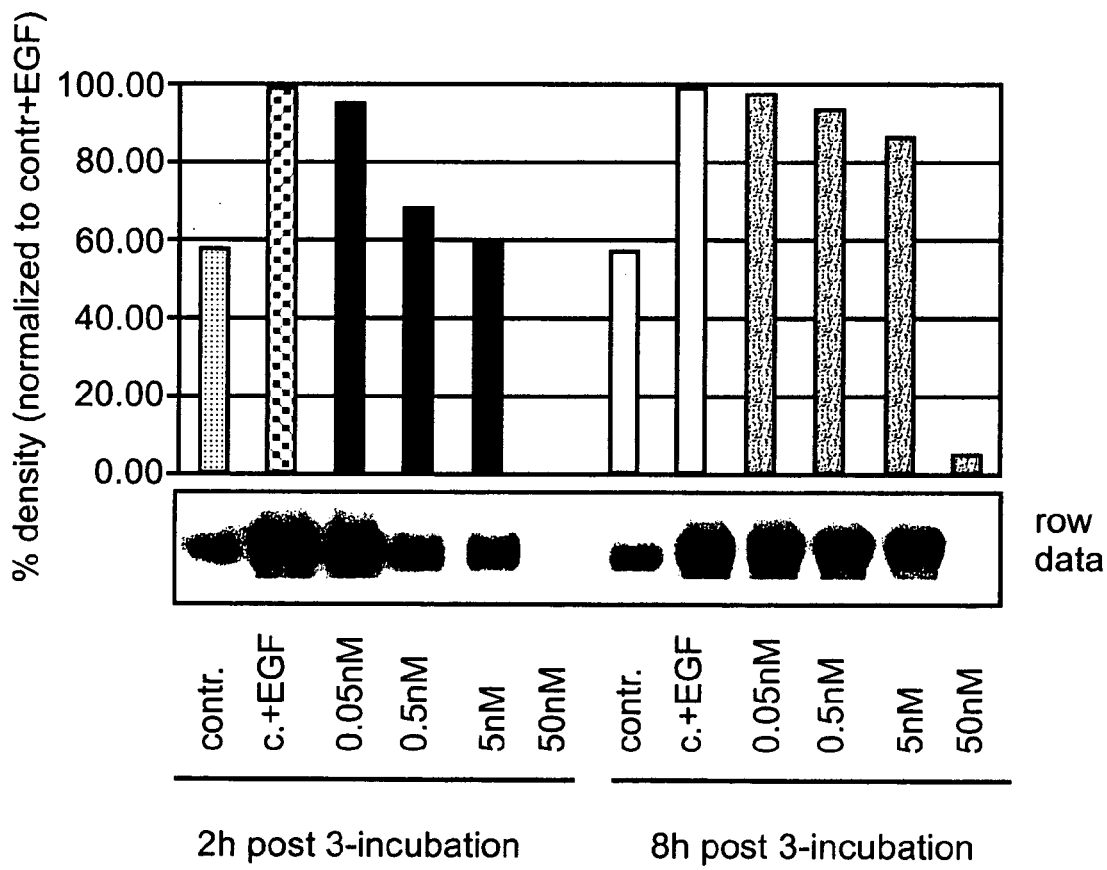
Figure 3:
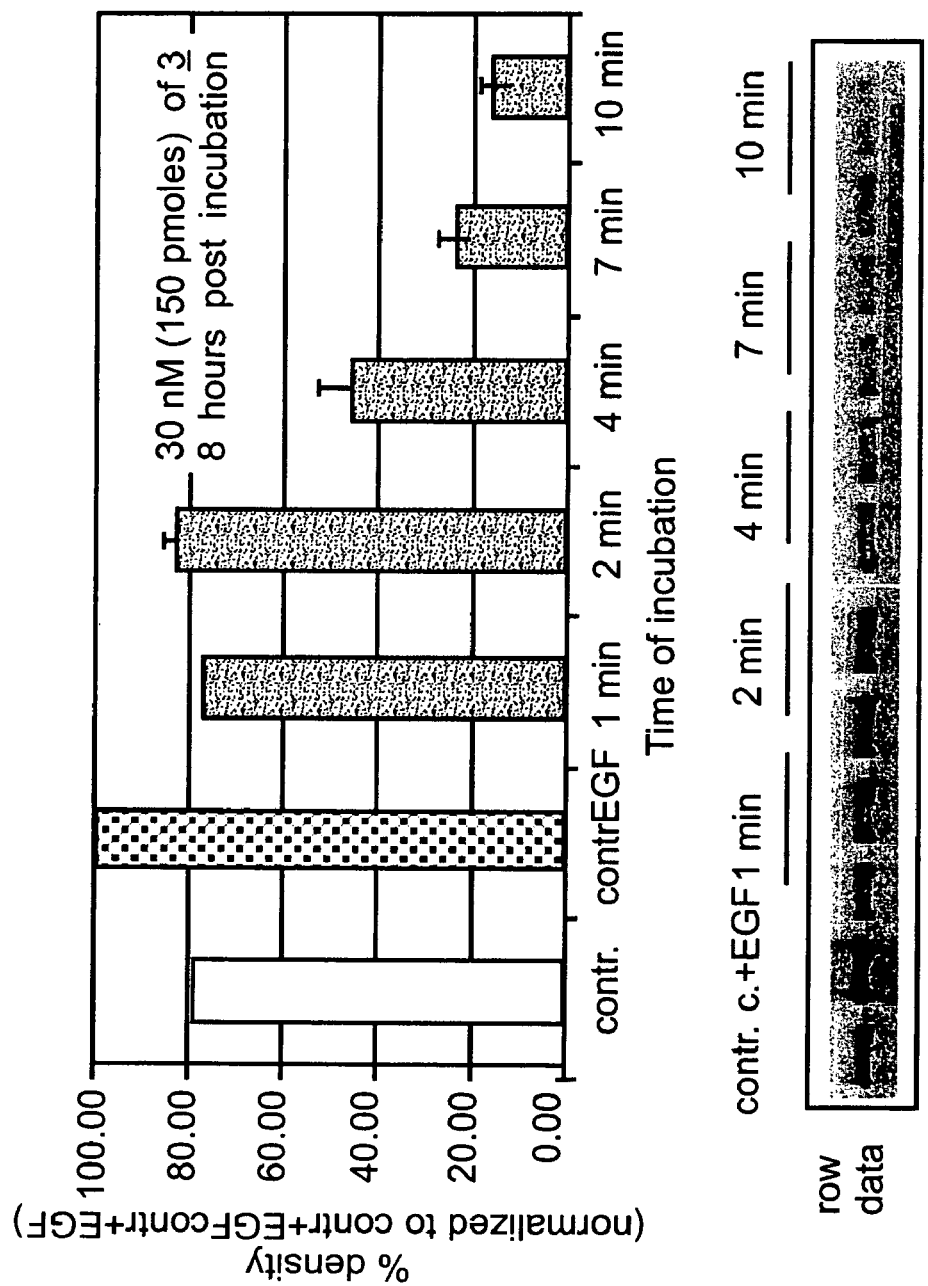
Figure 4:
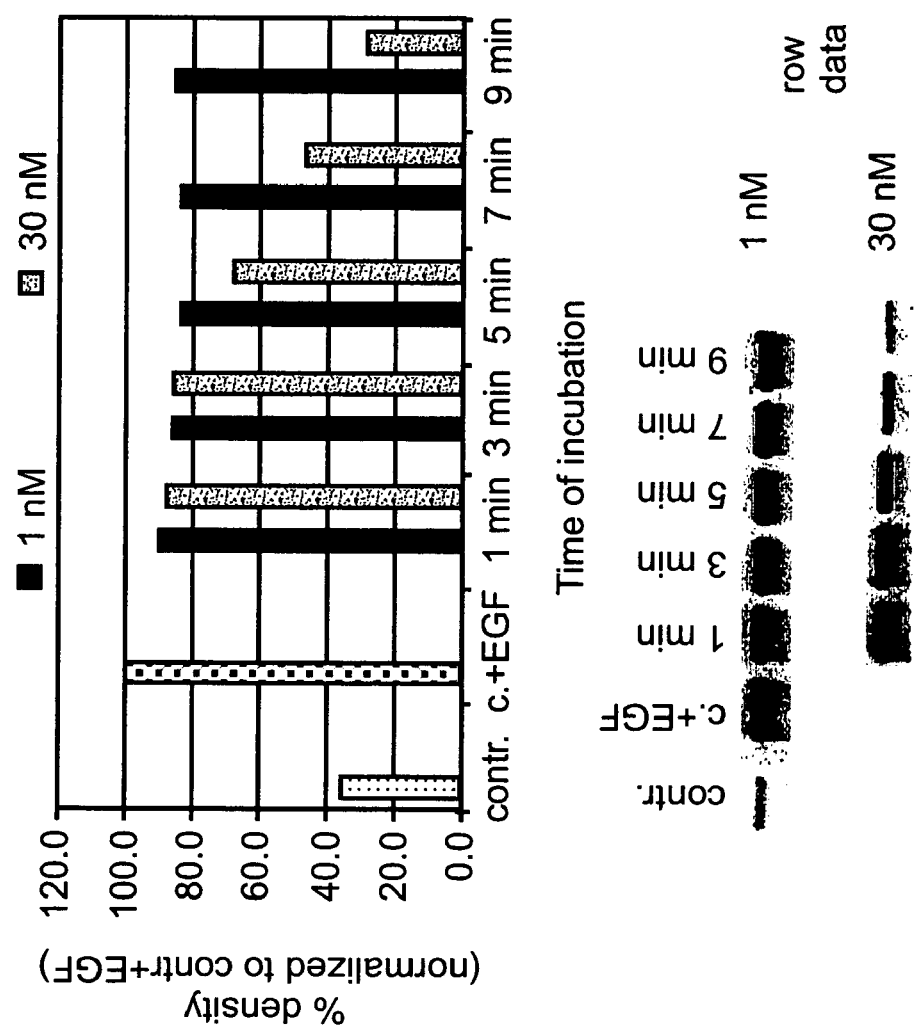
Figure 5:
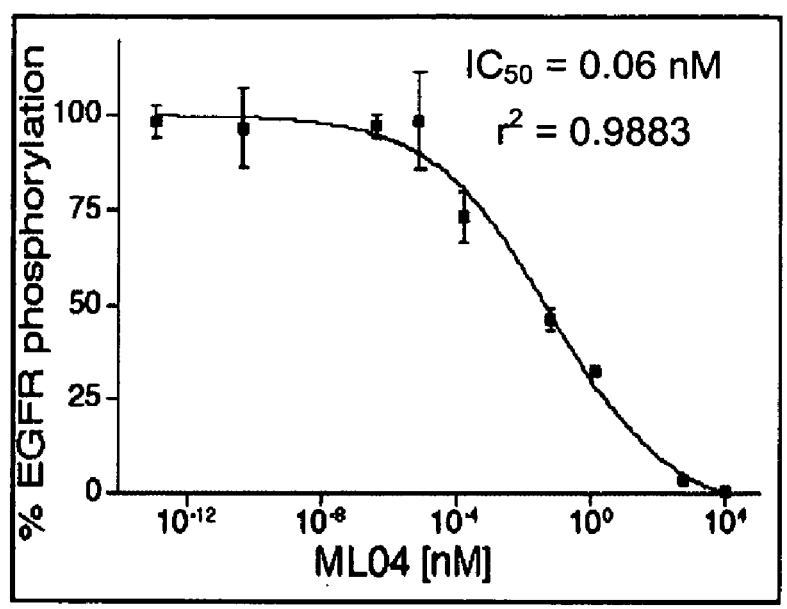
Figure 6:
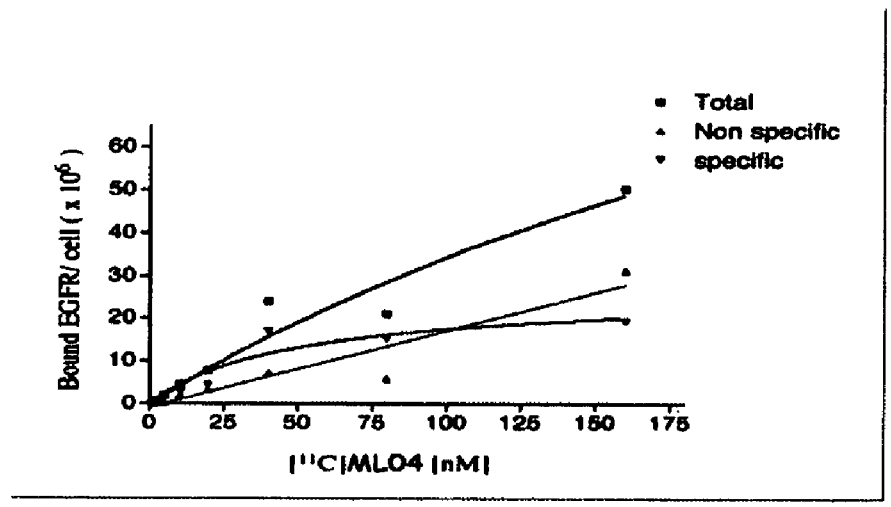
Figure 7:
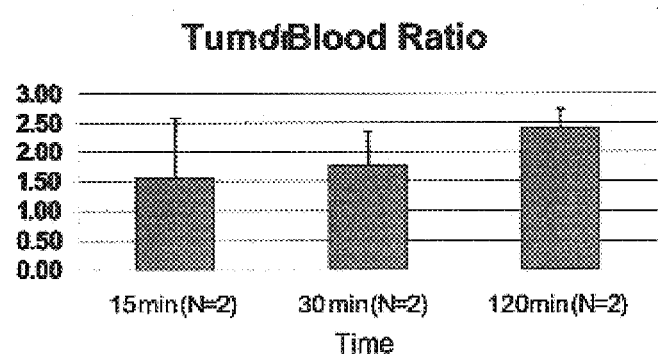
Figure 8A:
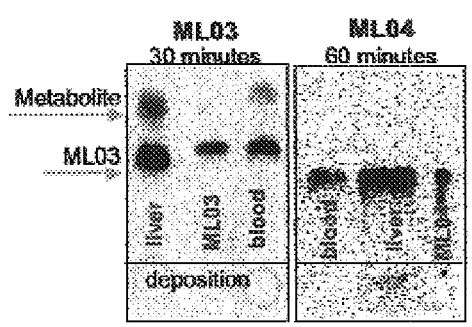
Figure 8B:
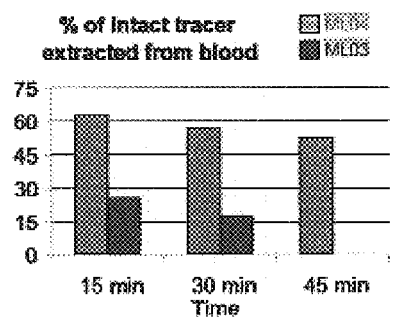
Figure 9:
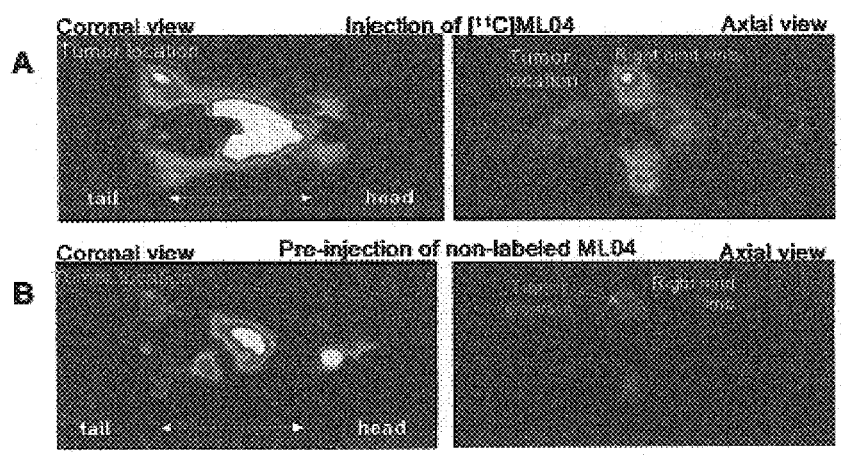
Figure 10:
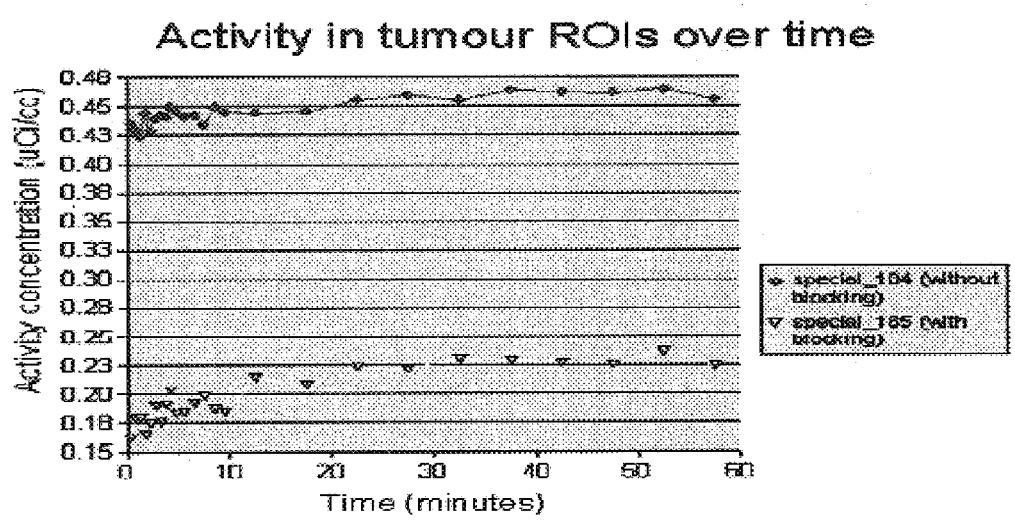
Figure 11:
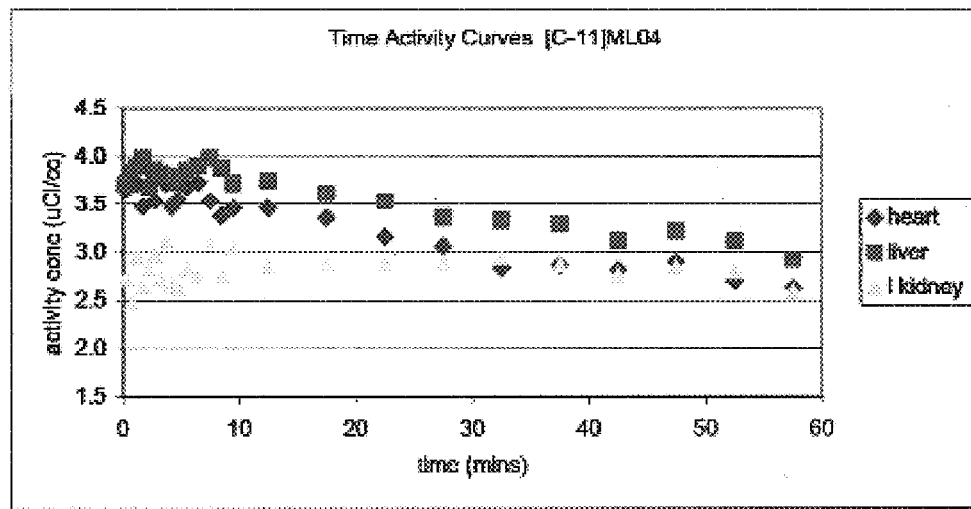
Figure 12:
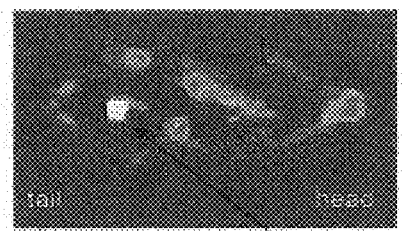
Figure 12:
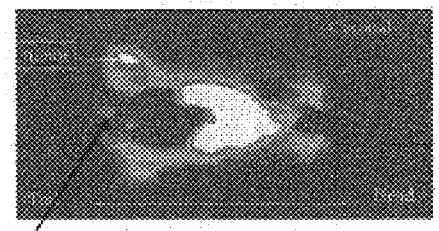

FIG. 1 presents an example of dose-response autophosphorylation inhibition curve for Compound 3 of the invention with an $IC_{50}$ value of 0.051 nM and a range of 0.0088/0.294 as 95% confidence interval;

FIG. 2 is a bar graph presenting the EGFR autophosphorylation level in A431 cells following incubation with various concentrations of Compound 3 and EGF stimulation-lysis at 2 hours and 8 hours post-incubation time (white bars with and without dots are control without EGF stimulation, bars with squared pattern are controls stimulated with EGF and the other bars show the described EGFR autophosphorylation level). The inset below shows a Western blot for each concentration at 2 hours and 8 hours post-incubation time and is coaligned with the bars;

FIG. 3 is a bar graph presenting the autophosphorylation levels of EGFR in A431 cells after varying incubation time with Compound 3, at 8-hour post-incubation time (the bars are the result of two determinations). The inset below shows a Western blot for each data point and is coaligned with the bars;

FIG. 4 is a bar graph presenting the autophosphorylation levels of EGFR in A431 cells after varying incubation time with 1 nM and 30 nM of Compound 3, at 1-hour post-incubation time. The inset below shows a Western blot for each data point and is coaligned with the bars;

FIG. 5 presents an example of dose-response autophosphorylation inhibition curve for Compound 4 of the present invention (denoted as ML04) with an $IC_{50}$ value of 0.06 nM;

FIG. 6 presents comparative plots demonstrating the specific binding of carbon-11 labeled Compound 4 of the present invention (denoted as ML04) to A431 cells;

FIG. 7 presents bar graphs demonstrating the tumor/blood ratio (in % ID/gram) in tumor-bearing rats injected with carbon-11 labeled Compound 4, 15, 30 and 120 minutes post injection;

FIGS. 8a–b presents comparative TLC chromatograms demonstrating the metabolism of C-11 radiolabeled Compound 3 (denoted as ML03) and Compound 4 (denoted as ML04), 30 minutes and 60 minutes post injection thereof to tumor bearing rats, respectively (FIG. 8a) and a bar graph demonstrating the percentages of intact tracer (radiolabeled Compounds 3 and 4), extracted from the blood 15, 30 and 45 minutes post injection;

FIG. 9 presents PET images of tumor bearing nude rats injected with carbon-11 labeled Compound 4 (A) and with non-labeled Compound 4 followed by carbon-11 labeled Compound 4 (B);

FIG. 10 presents comparative plots demonstrating the activity concentration of carbon-11 labeled Compound 4 in tumor over time, when administered to rats alone (diamonds) and when administered 10 minutes following administration of non-labeled Compound 4 (triangles);

FIG. 11 presents plots demonstrating the activity concentration of carbon-11 labeled Compound 4 over time in the heart (diamond), liver (squares) and kidney (triangles) of rats; and FIG. 12 presents PET coronal views demonstrating the bladder excretion of PDG (left image) and carbon-11 labeled Compound 4 (right image).

DESCRIPTION OF THE PREFERRED EMBODIMENTS

The present invention is of novel radiolabeled compounds which can be used as biomarkers for radioimaging such as Positron Emission Tomography (PET) and Single Photon Emission Computed Tomography (SPECT) and as radiopharmaceuticals for radiotherapy. Specifically, the novel radiolabeled compounds can be used as irreversible PET or SPECT biomarkers and/or as radiopharmaceuticals, for quantification, mapping and radiotherapy of epidermal growth factor receptor tyrosine kinase (EGFR-TK) associated diseases, such as a variety of cancers in which amplification, mutation and/or over expression of EGFR-TK has occurred.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the examples. The invention is capable of other embodiments or of being practiced or carried out in various ways. Also, it is to be understood that the phraseology and terminology employed herein is for the purpose of description and should not be regarded as limiting.

According to one aspect of the present invention there is provided a radiolabeled compound of a formula:

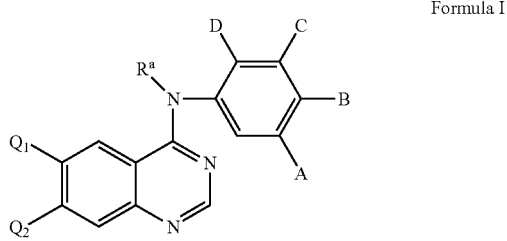

Formula I

Wherein:

Q1 is X—Y(=O)-Z and Q2 is selected from the group consisting of hydrogen, halogen, alkoxy, hydroxy, thiohydroxy, thioalkoxy, alkylamino and amino, or Q1 is selected from the group consisting of hydrogen, halogen, alkoxy, hydroxy, thiohydroxy, thioalkoxy, alkylamino and amino and Q2 is X—Y(=O)-Z;

X is selected from the group consisting of —NR$^1$—, —O—, —NH—NR$^1$—, —O—NR$^1$—, NH—CHR$^1$—, —CHR$^1$—NH—, —CHR$^1$—O—, —O—CHR$^1$—, —CHR—CH$_2$— and —CHR$^1$—S— or absent;

Y is selected from the group consisting of a non-radioactive carbon and a radioactive carbon;

Z is selected from the group consisting of —R$^2$C=CR$^3$, —C≡C—R$^3$ and —R$^2$C=C=CHR$^3$;

R$^a$ is selected from the group consisting of hydrogen or alkyl having 1–8 carbon atoms;

A, B, C and D are each independently selected from the group consisting of hydrogen, a non-radioactive derivatizing group and a radioactive derivatizing group selected from a radioactive bromine, a radioactive iodine and a radioactive fluorine;

R$^1$ is selected from the group consisting of hydrogen and substituted or non-substituted alkyl having 1–6 carbon atoms;

R$^2$ is selected from the group consisting of hydrogen, halogen and alkyl having 1–6 carbon atoms; and R$^3$ is selected from the group consisting of hydrogen, halogen, carboxy, alkenyl, alkoxy, carbonyl, substituted or non-substituted alkyl having 1–6 carbon atoms and substituted or non-substituted phenyl;

with the provision that the compound comprises at least one (e.g., one, two or more) radioactive atom.

As used herein in the specification and in the claims section that follows, the phrase "radiolabeled compound" or "radioactive atom" (type specified or not) refer to a compound that comprises one or more radioactive atoms or to a radioactive atom with a specific radioactivity above that of background level for that atom. It is well known, in his respect, that naturally occurring elements are present in the form of varying isotopes, some of which are radioactive isotopes. The radioactivity of the naturally occurring elements is a result of the natural distribution of these isotopes, and is commonly referred to as a background radioactive level. However, there are known methods of enriching a certain element with isotopes that are radioactive. The result of such enrichment is a population of atoms characterized by higher radioactivity than a natural population of that atom, and thus the specific radioactivity thereof is above the background level.

Thus, the radiolabeled compounds of the present invention have a specific radioactivity that is higher than the corresponding non-labeled compounds, and can therefore be used as agents for radioimaging and radiotherapy.

Furthermore, the term "non-radioactive", as used herein with respect to an atom or a derivatizing group, refers to an atom or a derivatizing group that does not comprise a radioactive atom and thus the specific radioactivity thereof is of a background level.

The term "radioactive", as used herein with respect to an atom or a derivatizing group, refers to an atom or a derivatizing group that comprises a radioactive atom and therefore the specific radioactivity thereof is above the background level.

As used herein in the specification and in the claims section that follows, the term "derivatizing group" refers to a major portion of a group which is covalently attached to another group.

As used herein in the specification and in the claims section that follows, the term "halogen", which is also referred to herein as "halo", refers to fluorine, chlorine, bromine or iodine.

As used herein, the term "hydroxy" refers to an —OH group.

As used herein, the term "alkyl" refers to a saturated aliphatic hydrocarbon including straight chain and branched chain groups. Preferably, the alkyl group is a medium size alkyl having 1 to 10 carbon atoms. More preferably, it is a lower alkyl having 1 to 6 carbon atoms. Most preferably it is an alkyl having 1 to 4 carbon atoms. Representative examples of an alkyl group are methyl, ethyl, propyl, isopropyl, butyl, tert-butyl, pentyl and hexyl.

The alkyl group, according to the present invention, may be substituted or non-substituted. When substituted, the substituent group can be, for example, cycloalkyl, alkenyl, aryl, heteroaryl, heteroalicyclic, hydroxy, alkoxy, aryloxy, thiohydroxy, thioalkoxy, thioaryloxy, halo, perhalo, trihalomethyl, carboxy, alkoxycarbonyl, thiocarhoxy, carbamyl, cyano, nitro, N-piperidinyl, N-piperazinyl, $N_1$-piperazinyl-$N_4$-alkyl, N-pyrrolidyl, pyridinyl, N-imidazoyl, N-morpholino, N-thiomorpholino, N-hexahydroazepine, amino or NRbRc, wherein Rb and Rc are each independently hydrogen, alkyl, hydroxyalkyl, N-piperidinyl, N-piperazinyl, $N_1$-piperazinyl-$N_4$-alkyl, N-pyrrolidyl, pyridinyl, N-imidazoyl, N-morpholino, N-thiomorpholino and N-hexahydroazepine.

As used herein, the term "cycloalkyl" refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptadiene and adamantane.

The term "alkoxy" refers to both an —O-alkyl and an —O-cycloalkyl group, as defined hereinabove. Representative examples of alkoxy groups include methoxy, ethoxy, propoxy and tert-butoxy.

The —O-alkyl and the O-cycloalkyl groups, according to the present invention, may be substituted or non-substituted. When substituted, the substituent group can be, for example, cycloalkyl, alkenyl, aryl, heteroaryl, heteroalicyclic, hydroxy, alkoxy, aryloxy, thiohydroxy, thioalkoxy, thioaryloxy, halo, perhalo, trihalomethyl, carboxy, alkoxycarbonyl, thiocarboxy, carbamyl, cyano, nitro, N-piperidinyl, N-piperazinyl, $N_1$-piperazinyl-$N_4$-alkyl, N-pyrrolidyl, pyridinyl, N-imidazoyl, $N_1$-morpholino, N-thiomorpholino, N-hexahydroazepine, amino or NRbRc, wherein Rb and Rc are each independently hydrogen, alkyl, hydroxyalkyl, N-piperidinyl, N-piperazinyl, $N_1$-piperazinyl-$N_4$-alkyl, N-pyrrolidyl, pyridinyl, N-imidazoyl, N-morpholino, N-thiomorpholino and N-hexahydroazepine.

The term "thiohydroxy" refers to a —SH group.

The term "thioalkoxy" refers to both an —S-alkyl group, and an —S-cycloalkyl group, as defined herein The term "amino" refers to a —$NH_2$ group.

The term "alkylamino" refers to a —NRbRc group wherein Rb and Rc are each independently hydrogen, alkyl, hydroxyalkyl, N-piperidinyl, N-piperazinyl, $N_1$-piperazinyl-$N_4$-alkyl, N-pyrrolidyl, pyridinyl, N-imidazoyl, N-morpholino, N-thiomorpholino and N-hexahydroazepine, or, alternatively, Rb and Rc are covalently attached one to the other so as to form a cyclic amino compound such as, but not limited to, N-piperidinyl, N-piperazinyl, $N_1$-piperazinyl-$N_4$-alkyl, N-pyrrolidyl, pyridin, N-imidazoyl, N-morpholino, N-thiomorpholino and N-hexahydroazepine.

The term "carboxy" refers to a —C(=O)— group.

The term "alkoxycarbonyl" group, also referred to herein as "carbalkoxy", refers to a —C(=O)—O—R' group, where R' is alkyl, cycloalkyl, alkenyl, aryl, heteroaryl (bonded through a ring carbon) or heteroalicyclic (bonded through a ring carbon) as defined hereinabove.

An "alkenyl" group refers to an alkyl group which consists of at least two carbon atoms and at least one carbon-carbon double bond.

An "aryl" group refers to an all-carbon monocyclic or fused-ring polycyclic (i.e., rings which share adjacent pairs of carbon atoms) group having a completely conjugated pi-electron system. Examples, without limitation, of aryl groups are phenyl, naphthalenyl and anthracenyl.

A "phenyl" group, according to the present invention can be substituted by one to three substituents or non-substituted. When substituted, the substituent group may be, for example, halogen, alkyl, alkoxy, nitro, cyano, trihalomethyl, alkylamino or monocyclic heteroaryl.

The term "heteroaryl" group includes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system.

An "aryloxy" group refers to both an —O-aryl and an —O-heteroaryl group, as defined herein.

An "thioaryloxy" group refers to both an —S-aryl and an —S-heteroaryl group, as defined herein.

A "trihalomethyl" group refers to a —$CX_3$ group, wherein X is a halogen as defined herein. A representative example of a trihalomethyl group is a —$CF_3$ group.

A "perhalo" group refers to a group in which all the hydrogen atoms thereof have been replaced by halogen atoms.

A "thiocarboxy" group refers to a —C(=S)—R' group, where R' is as defined herein.

An "alkylsulfinyl" group refers to an —S(=O)—R' group, where R' is as defined herein.

An "alkylsulfonyl" group refers to an —$S(=O)_2$—R' group, where R' is as defined herein.

A "carbamyl" group refers to an —OC(=O)—NRbRc group, where Rb and Rc are as defined herein.

A "nitro" group refers to a —$NO_2$ group.

A "cyano" group refers to a —C≡N group.

The radiolabeled compounds of the present invention are derivatized 4-(phenylamino)quinazolines that are substituted at position 6 or 7 of the quinazoline ring by an α,β-unsaturated carboxylic group, also defined herein as an X—Y(=O)-Z group.

As used herein in the specification and in the claims section that follows, the term "α,β-unsaturated carboxylic group" refers to any group that comprises a —C(=O)— group and is linked at the distal end thereof to an unsaturated group. The carboxylic group can be, for example, an amide, an ester, a hydrazinamide or a ketone.

The term "unsaturated group" refers to a substituted or non-substituted hydrocarbon that comprise at least two carbon atoms and at least one unsaturated bond. Representative examples of an unsaturated group include alkenyl, alkynyl and diene.

This class of derivatized 4-(phenylamino)quinazolines is known to bind irreversibly to the ATP site of EGFR-TK due to the α,β-unsaturated carboxylic group attached to the anilinoquinazoline ring [15, 16 and U.S. Pat. Nos. 6,153,617 and 6,127,374]. The α,β-unsaturated carboxylic group was found to covalently attach to the Cys-773 at the EGFR-TK ATP binding site, and thus acts as a Michael acceptor.

Prior to the disclosure of this class of compounds, derivatized 4-(phenylamino)quinazolines were known to bind reversibly to the EGFR-TK ATP site. The level of the biological activity of these compounds is influenced by the nature of the derivatizing groups at the anilino ring thereof. However, the covalent binding to the receptor, which is effected by the α,β-unsaturated carboxylic group attached to this class of quinazolines, enables the use of 4-(phenylamino)quinazolines that are derivatized by various derivatizing groups as EGFR-TK inhibitors. Nevertheless, the derivatizing groups can be attached to both the aniline ring and the quinazoline ring of the compounds of the present invention. The nature of these derivatizing groups may affect the binding affinity of the compound to the receptor as well as other biological activity parameters such as specificity, metabolism of the compound and kinetic rates.

Thus, according to a preferred embodiment of the present invention, the non-radioactive derivatizing group of the radiolabeled compound of the present invention is attached to the aniline ring and includes, for example, hydrogen, halogen, alkyl, haloalkyl, hydroxy, alkoxy, carboxy, carbalkoxy, thiohydroxy, thiocarboxy, thioalkoxy, alkylsulfinyl, alkylsulfonyl, amino, diamino, carbamyl, dicarbamoyl, nitro and cyano, as these terms are defined hereinabove.

According to another preferred embodiment of the invention, a non-radioactive derivatizing group is attached to the quinazoline group (as is represented in Formula I hereinabove by either Q1 or Q2) and includes, for example, halogen, alkoxy, hydroxy, thiohydroxy, thioalkoxy, alkylamino and amino. Preferably, this derivatizing group is an alkoxy group and, more preferably, it is an alkoxy group that comprises a morpholino group such as, but not limited to, a 3-(4-morpholinyl)propoxy group. Further preferably, the derivatizing group is a substituted or non-substituted morpholino group or a substituted or non-substituted piperazino group. The presence of a morpholino or piperazino group in this class of compounds in known to increase their biological availability [15].

Another factor which influences the binding potency of the derivatized 4-(phenylamino)quinazolines of the present invention is the position of the α,β-unsaturated carboxylic group attached to the quinazoline ring. A 6-position α,β-unsaturated carboxylic group has higher binding potency to the EGFR-TK ATP site [15, 16 and U.S. Pat. Nos. 6,153,617 and 6,127,374]. Thus, according to another preferred embodiment of the present invention, the X—Y(=O)-Z group of the radiolabeled compound is attached to position 6 of the quinazoline ring.

According to still another preferred embodiment of the invention, the 6-position α,β-unsaturated carboxylic group is an acrylamide group. Thus, a preferred radiolabeled compound according to the present invention is a radiolabeled N-[4-(phenylamino)quinazolin-6-yl]acrylamide derivatized by the $R^a$, A, B, C and D as these symbols are defined above.

The acrylamide group can be further derivatized by a derivatizing group that includes, for example, halogen, carboxy, alkenyl, alkoxy, carbonyl, substituted or non-substituted alkyl and substituted or non-substituted phenyl, as these terms are defined hereinabove. Preferably, the acrylamide group is derivatized by a substituted alkyl and, more preferably, the alkyl is substituted by an amino group such as, but not limited to, an alkylamino group and a dialkylamino group. More preferably, the alkyl is substituted by a dialkylamino group such as, but not limited to, dimethylamino, diethylamino, dipropylamino and diisopropylamino. Optionally, the alkyl is substituted by a morpholino group.

Thus, according to another preferred embodiment of the present invention, the α,β-unsaturated carboxylic group is 4-(dialkylamino)-2-butenamide. The presence of an α,β-unsaturated carboxylic group derivatized by a dialkylamino group is advantageous since the dialkylamino group increases the solubility of the compound under physiological conditions and hence increases the biological availability of the compound [19]. Furthermore, the presence of a dialkylamino group reduces the chemical reactivity of the unsaturated center of the compound as a Michael acceptor in nucleophilic reactions, due to electronic and steric effects. This reduced chemical reactivity is advantageous since the unsaturated center in this class of compounds is highly reactive and thus reacts, in addition to the targeted Cys-773 at the EGFR-TK ATP binding site, with other —SH residues that are present in the blood and other organs. Thus, by reducing its reactivity, the dialkylamino group enhances the binding specificity of the compound to the receptor.

U.S. Pat. No. 6,126,917 further teaches that 4-(phenylamino)quinazolines that are derivatized at position 6 of the anilino group by fluorine are potent inhibitors of EGFR-TK. The highest affinity toward the receptor is achieved using 4-[(3,4-dichloro-6-fluorophenyl)amino]quinazolines.

Thus, according to a preferred embodiment of the invention Y is a carbon, X is —NH, Z is $CH_2=CH$—, $R^a$ is hydrogen, A and B are each chlorine, C is hydrogen and D is fluorine, which is referred to hereinbelow as Compound 3.

According to another preferred embodiment of the invention, Y is a radioactive carbon, and the radioactive carbon is carbon-11.

According to still another preferred embodiment of the invention, at least one of A, B, C and D is a radioactive fluorine, and the radioactive fluorine is fluorine-18. Preferably, D is fluorine-18.

According to yet another preferred embodiment of the present invention, A is bromine or iodine and B, C and D are each hydrogen.

Thus, according to a presently most preferred embodiment of the invention, in Compound 3, Y is carbon-11.

According to another presently preferred embodiment of the invention, in Compound 3, D is fluorine-18.

According to another preferred embodiment of the present invention, Y is a carbon, X is —NH, Z is $(CH_3)_2N$—$CH_2$—$CH=CH$—, $R^a$ is hydrogen and A, B, C and D are as defined hereinabove, which is referred to hereinbelow as Compound 4.

Preferably, in Compound 4, A and B are each chlorine, C is hydrogen and D is fluorine. Alternatively, A is bromine or iodine and B, C and D are each hydrogen.

Further preferably, in Compound 4, Y is a non-radioactive carbon and at least one of A, B, C and D is a radioactive fluorine, and the radioactive fluorine is fluorine-18. Preferably, D is fluorine-18.

Further preferably, in Compound 4, Y is a non-radioactive carbon and at least one of A, B, C and D is a radioactive iodine, and the radioactive iodine is iodine-124. Preferably, A is iodine-124. This compound is referred to hereinbelow as Compound 5.

Most preferably, in Compound 4, a methyl group in the derivatizing dimethylamino group comprises a radioactive carbon and the radioactive carbon is carbon-11.

Further according to preferred embodiments of the invention the radioactive atom is a radioactive bromine such as bromine-76 and bromine-77. Preferably, A is the radioactive bromine. A bromine-76 labeled compound of the invention can be used for PET radioimaging, while a bromine-77 labeled compound of the invention can be used for radiotherapy.

According to another preferred embodiments of the present invention the radioactive atom is a radioactive iodine such as iodine-123, iodine-124 or iodine-131. Preferably, A is the radioactive iodine. An iodine-123 labeled compound of the invention can be used for SPECT radioimaging, an iodine-124 labeled compound of the invention can be used for both PET radioimaging and/or radiotherapy and an iodine-131 labeled compound of the invention can be used for radiotherapy.

Radiosyntheses:

According to another aspect of the present invention, there are provided methods for the syntheses of the radiolabeled compounds of the invention.

The radiolabeling of the compounds can be performed using three alternative strategies as follows:

The first strategy involves the incorporation of fluorine-18 atom within the aniline ring and therefore requires that the radiolabeling be the first step of a multi-step radiosynthesis, which typically includes a total of four- to eight-step radiosynthesis, as is further exemplified in the Examples section that follows.

The second strategy for radiolabeling according to the present invention involves the incorporation of a carbon-11 atom within the α,β-unsaturated carboxylic residue which is performed at the final step of the synthesis, this being an advantageous one-step radiosynthesis. The incorporation of the carbon-11, according to this strategy, can be performed either at the α-carbon or at the ω-atom of the α,β-unsaturated carboxylic residue.

The third strategy involves the incorporation of radioactive bromine or radioactive iodine within the anilino ring of the 4-(phenylamino)quinazoline, prior to the final step of the synthesis, resulting in an advantageous two-step radiosynthesis, wherein the final step is simple to perform (see below).

Thus, according to still another aspect of the present invention, there is provided a method of synthesizing a carbon-11 labeled compound as is described hereinabove. The method is effected by coupling an aniline derivatized by $R^a$, A, B, C and D with a 4-chloroquinazoline substituted at position 6 and/or 7 by one or more reactive group(s), so as to produce a reactive 4-(phenylamino)quinazoline derivatized by $R^a$, A, B, C and D, and reacting the reactive 4-(phenylamino)quinazoline with a reactive carbon-11 labeled α,β-unsaturated carboxylic derivative. Alternatively, the method further includes reacting the reactive 4-(phenylamino)quinazoline with a chemically reactive group, prior to its reaction with the α,β-unsaturated carboxylic derivative, so as to produce a reactive substituted 4-(phenylamino)quinazoline.

As used herein in the specification and in the claims section that follows, the term "reactive" with respect to a group or a derivative refers to a group or derivative which can be easily reacted with another group so as to produce a new compound that comprises a new functional group. Representative examples of a reactive group include nitro, amino, hydroxy, alkoxy and halogen. A carboxylic acid chloride is a representative example of a reactive derivative. An alkoxy group which comprises a metal salt of hydroxyalkyl is a representative example of a chemically reactive group. Preferably, the chemically reactive group comprises a metal salt, e.g., sodium salt, potassium salt or lithium salt, of 3-(4-morpholinyl)-1-propanol, which is also referred to herein as 3-(4-morpholinyl)propoxy.

In one particular, which includes a quinazoline that is substituted by one reactive group at position 6 thereof, 3,4-dichloro-6-fluoroaniline is reacted with 4-chloro-6-nitroquinazoline, so as to produce 4-[(3,4-dichloro-6-fluorophenyl)amino]-6-nitroquinazoline, which is reduced, by means of an ethanolic solution of hydrazine hydrate and Raney®Nickel, so as to produce 4-[(3,4-dichloro-6-fluorophenyl)amino]-6-aminoquinazoline. Then, the 4-[(3,4-dichloro-6-fluorophenyl)amino]-6-aminoquinazoline is reacted with a carbon-11 labeled acryloyl chloride so as to produce a carbon-11 labeled N-{4-[(3,4-dichloro-6-fluorophenyl)amino]quinazoline-6-yl}acrylamide (carbon-11 labeled Compound 3).

Optionally, the starting material is 3-bromoaniline or 3-iodoaniline and the final product is N-{4-[(3-bromophenyl)amino]quinazoline-6-yl}acrylamide or N-{4-[(3-iodophenyl)amino]quinazoline-6-yl}acrylamide, respectively.

In another particular, which includes a quinazoline that is substituted by two different reactive groups at positions 6 and 7 thereof, 3,4-dichloro-6-fluoroaniline is reacted with 4-chloro-7-fluoro-6-nitroquinazoline, so as to produce 4-[(3,4-dichloro-6-fluorophenyl)amino]-7-fluoro-6-nitroquinazoline. The 4-[(3,4-dichloro-6-fluorophenyl)amino]-7-fluoro-6-nitroquinazoline is then reacted with a sodium salt of 3-(4-morpholinyl-1-propanol), so as to produce 4-[(3,4-dichloro-6-fluoro-phenyl)amino]-7-[3-(4-morpholinyl)propoxy]-6-nitroquinazoline, which is reduced, by means of an ethanolic solution of hydrazine hydrate and Raney®Nickel, so as to produce 6-amino-4-[(3,4-dichloro-6-fluorophenyl)amino]-7-[3-(4-morpholinyl)propoxy]quinazoline. The product is then reacted with a carbon-11 labeled acryloyl chloride so as to produce a carbon-11 labeled N-{4-[(3,4-dichloro-6-fluorophenyl)amino]-7-[3-(4-morpholinyl)propoxy]quinazoline-6-yl}acrylamide (carbon-11 labeled morpholino-substituted Compound 3).

Optionally, the starting material is 3-bromoaniline or 3-iodoaniline and the product is {4-[(3-bromophenyl)amino]-7-[3-(4-morpholinyl)propoxy]quinazoline-6-yl}acrylamide or {4-[(3-iodophenyl)amino]-7-[3-(4-morpholinyl)propoxy]quinazoline-6-yl}acrylamide, respectively.

Alternatively, and according to another aspect of the present invention, there is provided another method of synthesizing a carbon-11 labeled compound as is described hereinabove. The method is effected by coupling an aniline derivatized by $R^a$, A, B, C and D with a 4-chloroquinazoline substituted at position 6 and/or 7 by one or more reactive group(s), so as to produce a reactive 4-(phenylamino)quinazoline derivatized by $R^a$, A, B, C and D, reacting the reactive 4-(phenylamino)quinazoline with a reactive α,β-unsaturated carboxylic derivative, which is terminating with a second reactive group, so as to produce a 4-(phenylamino)quinazoline substituted at position 6 or 7 by an α,β-unsaturated carboxylic group terminating with the second reactive group, reacting the produced substituted 4-(phenylamino)quinazoline with a reactive substituted alkyl having 1–6 carbon atoms, so as to produce a 4-(phenylamino)quinazoline substituted at position 6 or 7 by the α,β-unsaturated carboxylic group terminating with the reactive substituted alkyl and reacting the 4-(phenylamino)quinazoline substituted at position 6 or 7 by the α,β-unsaturated carboxylic group terminating with the reactive substituted alkyl with a carbon-11 labeled reactive compound.

Representative examples of a reactive α,β-unsaturated carboxylic derivative, which is terminating with a second reactive group, include ω-halogenated α,β-unsaturated carboxylic derivatives such as, but not limited to, 4-bromocrotonyl chloride, 4-chlorocrotonyl chloride and 4-iodocrotonyl chloride.

Representative examples of a reactive substituted alkyl include alkylamines such as, but not limited to, methylamine, ethylamine, propylamine and isopropylamine.

Representative examples of a carbon-11 reactive compound include carbon-11 methyl iodide, carbon-11 ethyl iodide, carbon-11 propyl iodide and carbon-11 methyl triflate, with carbon-11 methyl triflate being preferable due to its relative reactivity and low volatility.

In one particular, 3,4-dichloro-6-fluoroaniline is reacted with 4-chloro-6-nitroquinazoline, so as to produce 4-[(3,4-dichloro-6-fluorophenyl)amino]-6-nitroquinazoline, which is reduced, by means of an ethanolic solution of hydrazine hydrate and Raney®Nickel, so as to produce 4-[(3,4-dichloro-6-fluorophenyl)amino]-6-aminoquinazoline. Then, the 4-[(3,4-dichloro-6-fluorophenyl)amino]-6-aminoquinazoline is reacted with 4-bromocrotonyl chloride, so as to produce 4-bromo-N-{4-[(3,4-dichloro-6-fluorophenyl)amino]quinazoline-6-yl}-2-butenamide, which is then reacted with methylamine, so as to produce N-{4-[(3,4-dichloro-6-fluorophenyl)amino]quinazoline-6-yl}-4-(methylamino)-2-butenamide. The obtained methylamino derivative of the butenamide is reacted with a carbon-11 labeled methyliodide, so as to produce a carbon-11 labeled N-{4-[(3,4-dichloro-6-fluorophenyl)amino]quinazoline-6-yl}-4-(dimethylamino)-2-butenamide (carbon-11 labeled Compound 4).

Optionally, the starting material is 3-bromoaniline or 3-iodoaniline and the obtained product is a carbon-11 labeled N-{4-[(3-bromophenyl)amino]quinazoline-6-yl}-4-(dimethylamino)-2-butenamide or a carbon-11 labeled N-{4-[(3-iodophenyl)amino]quinazoline-6-yl}-4-(dimethylamino)-2-butenamide.

According to yet another aspect of the present invention, there is provided a method of synthesizing a fluorine-18 labeled compound as is described hereinabove. The method is effected by preparing a fluorine-18 labeled aniline derivatized by A, B, C and D by means of reacting a pre-selected nitrobenzene with a $^{18}$F-fluoride ion and thereafter reducing the fluoronitrobenzene obtained, by means of an ethanolic solution of hydrazine hydrate and Raney®Nickel. Then, coupling the derivatized fluorine-18 labeled aniline with 4-chloroquinazoline substituted at position 6 and/or 7 by one or more reactive group(s) as defined herein, so as to produce a reactive fluorine-18 labeled 4-(phenylamino)quinazoline derivatized by A, B, C and D, and reacting the reactive fluorine-18 labeled 4-(phenylamino)quinazoline with a reactive α,β-unsaturated carboxylic derivative.

In one particular, fluorine-18 labeled 3,4-dichloro-6-fluoroaniline is prepared by reacting 1,2-dichloro-4,5-dinitrobenzene with $^{18}$F-fluoride ion and reducing the obtained fluorine-18 labeled 3,4-dichloro-6-fluoronitrobenzene as described hereinabove. The fluorine-18 labeled aniline is then reacted with 4-chloro-6-nitroquinazoline, and the obtained fluorine-18 labeled 4-[(3,4-dichloro-6-fluorophenyl)amino]-6-nitroquinazoline is reduced thereafter, by means of an ethanolic solution of hydrazine hydrate and Raney®Nickel, so as to produce fluorine-18 labeled 4-[(3,4-dichloro-6-fluorophenyl)amino]-6-aminoquinazoline, which is reacted with an acryloyl chloride so as to produce a fluorine-18 labeled N-{4-[(3,4-dichloro-6-fluorophenyl)amino]quinazoline-6-yl}acrylamide (fluorine-18 labeled Compound 3).

Optionally, the fluorine-18 labeled aniline is reacted with 4-chloro-7-fluoro-6-nitroquinazoline, and the obtained product is then reduced as described hereinabove so as to produce fluorine-19 labeled 6-amino-4-[(3,4-dichloro-6-fluorophenyl)amino]-7-[3-(4-morpholinyl)propoxy]quinazoline. The obtained fluorine-18 labeled substituted aminoquinazoline is then reacted with the acryloyl chloride so as to produce the radiolabeled (fluorine-18 labeled) Compound 3 derivatized by a morpholino group.

Further optionally, the obtained fluorine-18 labeled 4-[(3,4-dichloro-6-fluorophenyl)amino]-6-aminoquinazoline is reacted with 4-bromocrotonyl chloride and thereafter with dimethylamine, so as to produce the radiolabeled (fluorine-18 labeled) Compound 4.

According to still another aspect of the present invention, there is provided a method of synthesizing a radioactive bromine labeled or a radioactive iodine labeled compound as is described hereinabove. The method is effected by coupling an aniline derivatized by $R^a$, A, B, C and D, wherein at least one of A, B, C and n is a halogen, with 4-chloroquinazoline substituted at position 6 and/or 7 by one or more reactive group(s) as defined herein, so as to produce a reactive 4-(phenylamino)quinazoline derivatized by A, B, C and D as defined herein, and radiolabeling the reactive 4-(phenylamino)quinazoline by means of reacting the reactive 4-(phenylamino)quinazoline derivatized by A, B, C and D, with bistributyltin, using tetrakis(triphenylphosphine) palladium as catalyst, so as to produce a reactive 4-(phenylamino)quinazoline derivatized by A, B, C and D, wherein at least one of A, B, C and D is tributyltin, and thereafter reacting the stanylated product with a radioactive bromine or a radioactive iodine, in the presence of an oxidizing agent, so as to produce a reactive radioactive bromine labeled or radioactive iodine labeled 4-(phenylamino)quinazoline. Then, reacting the reactive radioactive bromine labeled or radioactive iodine labeled 4-(phenylamino)quinazoline with a reactive α,β-unsaturated carboxylic derivative.

In one particular, 3-bromoaniline is reacted with 4-chloro-6-nitroquinazoline to produce 4-[(3-bromophenyl)amino]-6-nitroquinazoline, which is reduced thereafter, by means of an ethanolic solution of hydrazine hydrate and Raney®Nickel, to the corresponding 6-aminoquinazoline. The 4-[(3-bromophenyl)amino]-6-aminoquinazoline is then reacted with bistributyltin in the presence of tetrakis(triphenylphosphine)palladium in THF solution and the obtained stanylated product is reacted thereafter with iodine 124, as described hereinabove. The obtained iodine-124 labeled 4-[(3-iodophenyl)amino]-6-aminoquinazoline is then reacted with an acryloyl chloride to produce an iodine-124 labeled N-{4-[(3-iodophenyl)amino]quinazoline-6-yl}acrylamide.

Optionally, the iodine-124 labeled aniline is reacted with 4-chloro-7-fluoro-6-nitroquinazoline, and the obtained product is then reduced as described hereinabove so as to produce iodine-124 labeled 6-amino-4-[(3-iodophenyl)amino]-7-[3-(4-morpholinyl)propoxy]quinazoline. The obtained iodine-124 labeled substituted aminoquinazoline is then reacted with the acryloyl chloride so as to produce the iodine-124 labeled N-{4[(3-iodophenyl)amino]quinazoline-6-yl}acrylamide derivatized by a morpholino group.

Further optionally, the obtained iodine-124 labeled 4-[(3-iodophenyl)amino]-6-aminoquinazoline is reacted with 4-bromocrotonyl chloride and thereafter with dimethylamine, so as to produce the radiolabeled Compound 5.

Iodine-124 is a presently most promising radionuclides which can be used for both effective radioimaging and radiotherapy. Hence, irreversible inhibitors radiolabeled by iodine-124, such as Compound 5, are highly potent agents, as is further detailed hereinbelow.

Radioimaging and Radiotherapy:

The radiolabeled compounds herein described can be used as radioimaging and radiotherapy agents carbon-11 labeled, fluorine-18 labeled, bromine-76 labeled and iodine-124 labeled compounds of the invention can be used as biomarkers for PET radioimaging, whereas iodine-123 labeled compounds of the invention can be used as biomarkers for SPECT radioimaging. Bromine-77 labeled, iodine-124 and iodine-131 labeled compounds of the invention can be used as radiopharmaceuticals for radiotherapy. Thus, the radiolabeled compounds of the invention can be used to effect a method of monitoring the level of epidermal growth factor receptor within) a body of a patient by administering to the patient any of the carbon-11, fluorine-18, bromine-76, iodine-123 or iodine-124 radiolabeled compounds described herein and employing a nuclear imaging technique, such as positron emission tomography or single photon emission computed tomography, for monitoring a distribution of the compound within the body or within a portion thereof.

Nuclear imaging dosing depends on the affinity of the compound to its receptor, the isotope employed and the specific activity of labeling. Persons ordinarily skilled in the art can easily determined optimum nuclear imaging dosages and dosing methodology.

The bromine-77, iodine-124 and iodine-131 radiolabeled compounds herein described can be used to effect a method of radiotherapy by administering to a patient a therapeutically effective amount of a radiolabeled compound as described herein, Led with, for example, a pharmaceutically acceptable carrier.

For any compound used in the method of the invention, a therapeutically effective amount, also referred to herein as a therapeutically effective dose, can be estimated initially from cell culture assays. For example, a dose can be formulated in animal models to achieve a circulating concentration range that includes the $IC_{50}$ or the $IC_{100}$ as determined in cell culture. Such information can be used to more accurately determine useful doses in humans. Initial dosages can also be estimated from in vivo data. Using these initial guidelines one having ordinary skill in the art could determine an effective dosage in humans.

Moreover, toxicity and therapeutic efficacy of the radiolabeled compounds described herein can be determined by standard pharmaceutical procedures in cell cultures or experimental animals, e.g., by determining the $LD_{50}$ and the $ED_{50}$. The dose ratio between toxic and therapeutic effect is the therapeutic index and can be expressed as the ratio between $LD_{50}$ and $ED_{50}$. Compounds which exhibit high therapeutic indices are preferred. The data obtained from these cell cultures assays and animal studies can be used in formulating a dosage range that is not toxic for use in human. The dosage of such compounds lies preferably within a range of circulating concentrations that include the $ED_{50}$ with little or no toxicity. The dosage may vary within this is range depending upon the dosage form employed and the route of administration utilized. The exact formulation, route of administration and dosage can be chosen by the individual physician in view of the patient's condition. (See, e.g., Fingl et al., 1975, In: The Pharmacological Basis of Therapeutics, chapter 1, page 1).

Dosage amount and interval may be adjusted individually to provide plasma levels of the active compound which are sufficient to maintain therapeutic effect. Usual patient dosages for oral administration range from about 50–2000 mg/kg/day, commonly from about 100–1000 mg/kg/day, preferably from about 150–700 mg/kg/day and most preferably from about 250–500 mg/kg/day. Preferably, therapeutically effective serum levels will be achieved by administering multiple doses each day. In cases of local administration or selective uptake, the effective local concentration of the drug may not be related to plasma concentration. One having skill in the art will be able to optimize therapeutically effective local dosages without undue experimentation.

Pharmaceutical Compositions:

Any of the radiolabeled compounds described herein can be formulated into a pharmaceutical composition which can be used for radiotherapy of a disease or for imaging. Such a composition includes as an active ingredient any of the radiolabeled compounds described herein and a pharmaceutically acceptable carrier.

As used herein a "pharmaceutical composition" refers to a preparation of one or more of the radiolabeled compounds described herein, with other chemical components such as pharmaceutically suitable carriers and excipients. The purpose of a pharmaceutical composition is to facilitate administration of a compound to an organism.

Hereinafter, the term "pharmaceutically acceptable carrier" refers to a carrier or a diluent that does not cause significant imitations to an organism and does not abrogate the biological activity and properties of the administered compound. Examples, without limitations, of carriers are: propylene glycol, saline, emulsions and mixtures of organic solvents with water. Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition.

Routes of administration: Suitable routes of administration may, for example, include oral, rectal, transmucosal, transdermal, intestinal or parenteral delivery, including intramuscular, subcutaneous and intramedullary injections as well as intrathecal, direct intraventricular, intravenous, intraperitoneal, intranasally, or intraocular injections.

Composition/formulation: Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more pharmaceutically acceptable carriers comprising excipients and auxiliaries, which facilitate processing of the active compounds into preparations which, can be used pharmaceutically. Proper formulation is dependent upon the route of administration chosen.

For injection, the compounds of the invention may be formulated in aqueous solutions, preferably in physiologically compatible buffers such as Hank's solution, Ringer's solution, or physiological saline buffer with or without organic solvents such as propylene glycol, polyethylene glycol. For transmucosal administration, penetrants are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by inhalation, the compounds for use according to the present invention are conveniently delivered ill the form of an aerosol spray presentation from a pressurized pack or a nebulizer with the use of a suitable propellant, e.g., dichlorodifluoromethane, trichlorofluoromethane, dichlorotetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The radiolabeled compounds described herein may be formulated for parenteral administration, e.g., by bolus injection or continuos infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active compounds may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile, pyrogen-free water, before use.

The radiolabeled compounds of the present invention may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Additional objects, advantages, and novel features of the present invention will become apparent to one ordinarily skilled in the art upon examination of the following examples, which are not intended to be limiting. Additionally, each of the various embodiments and aspects of the present invention as defined hereinabove and as claimed in the claims section below finds experimental support in the following examples.

EXAMPLES

Reference is now made to the following examples, which together with the above descriptions, illustrate the invention in a non-limiting fashion, Materials, Syntheses and Experimental Methods Syntheses:
Materials and Methods:
Chemicals were purchased from Sigma Chemical Co. (St. Louis, Mo.), Fisher Scientific (Pittsburgh, Pa.), Aldrich Co. (Milwaukee, Wis.) or Carlo Erba. All the chemicals were used as supplied, except DMSO which was stored over activated molecular sieves for at least one day prior to use, THF which was freshly distilled prior to use and vinyl magnesium which was freshly prepared by reacting vinyl bromide and magnesium turnings, according to well-known procedures, prior to use. Microwave heating was performed in a conventional oven (BR 740XL, Brother) operating at 500 W (full power).

Generation of [F-18]Fluoride ion: $^{18}$F-Fluoride ion was produced by the $^{18}$O(p, n) $^{18}$F nuclear reaction on about 350 μl $^{18}$O-enriched water (97% isotopic purity, Rotem, Israel) as a target in the Hadassab-Hebrew University IBA 18/9 cyclotron (Belgium). Reactive organic $^{18}$F-fluoride ion was prepared by adding 10–50 μl irradiated target water to Kryptofix®2.2.2 (10 mg, 27 μl) and $K_2CO_3$ (1 mg) in water-acetonitrile. Azeotropic removal of water with acetonitrile was achieved by heating under a stream of nitrogen. The dried Kryptofix®2.2.2—potassium $^{18}$F-fluoride was then dissolved in 300 μl anhydrous DMSO for use in radiolabeling.

Generation of carbon-11 $CO_2$: carbon-11 $CO_2$ was produced by the $^{14}$N(p, α) $^{11}$C nuclear reaction on a mixture of $N_2$/0.5% $O_2$ as a target, in the Hadassah-Hebrew University IBA 18/9 cyclotron (Belgium).

Generation of carbon-11 methyl iodide: carbon-11 methyl iodide is produced according to a known procedure [20].

Generation of iodine-124 sodium iodide: [Iodine-124] sodium iodide was purchased from Eldan Inc., Israel.

HPLC was performed on a Varian 9012Q pump, a Varian 9050 variable wavelength UV detector operating at 254 nm, and a Bioscan Flow-Count radioactivity detector with a NaI crystal.

The carbon-11 labeled, fluorine-18 labeled, radioactive bromine labeled and radioactive iodine labeled compounds were purified on a reverse phase system using a C18-reverse phase-prep column and the following mobile phase system: 48% CH$_3$CN in 52% acetate buffer (pH=3.8), at 15 ml/minute flow rate. Eluent fractions (2.5 ml) were collected on a fraction collector (FC205, Gilson). Analysis of formulated radiotracers was performed on C18 column μ Bondapak analytical column, using 40% CH$_3$CN in 60% acetate buffer (pH=3.8) as elute, at a flow rate of 1.7 ml/min Radiotracers formulation was performed as follows: The product was collected in a vial that contained 50 ml water and 1 ml NaOH (1 M). The solution was passed through a pre-washed (10 ml water) activated C18 cartridge, and washed with 10 ml sterile water. The product was eluted using 1 ml ethanol followed by 5 ml of saline.

General Synthetic Schemes:

Carbon-11 Labeled 4-(phenylamino)quinazolines substituted by an α,β-Unsaturated Carboxylic Group (Michael Acceptor Side-chain):

A general synthetic pathway for producing carbon-11 labeled 4-(phenylamino)quinazolines substituted by an α,β-unsaturated carboxylic group, as is presented in Scheme 1, includes the steps of: (i) coupling a derivatized or non-derivatized aniline with 4-chloroquinazoline that is substituted at position 6 or 7 by a reactive group (L, Scheme 1, see examples below), so as to produce a reactive 4-(phenylamino)quinazoline; and (ii) reacting the reactive quinazoline, under the appropriate conditions, with a reactive derivative of a carbon-11 labeled α,β-unsaturated carboxylic group (X—Y(=O)-M, Scheme 1), so as to produce the carbon-11 labeled 4-(phenylamino)quinazoline substituted at position 6 or 7 thereof by an α,β-unsaturated carboxylic group,

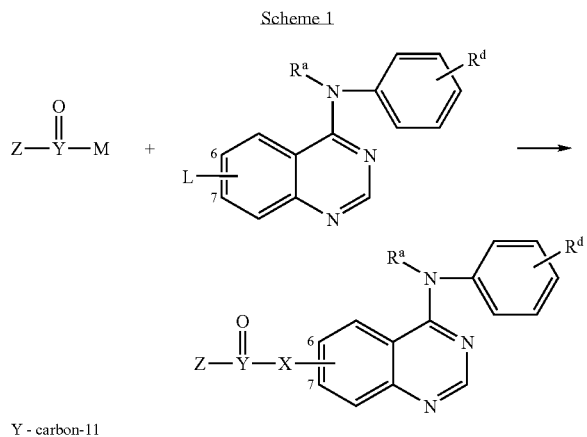

Scheme 1

Y - carbon-11

Thus, according to the general pathway described above (Scheme 1), carbon-11 labeled 4-(phenylamino)quinazolines substituted by the following α,β-unsaturated carboxylic side-chain groups are synthesizable:

Amine-linked side-chains: 4-(phenylamino)quinazoline substituted at position 6 or 7 by a nitro group is reduced to the corresponding amine, which is acylated by a carbon-11 labeled α,β-unsaturated carboxylic acid in the presence of a coupling agent, such as EI or AC, or by the acid chloride.

Oxygen-linked side-chains: 4-(phenylamino)quinazoline substituted at position 6 or 7 by a methoxy group is cleaved to produce the corresponding hydroxyl compound, which is then acylated either by a carbon-11 labeled α,β-unsaturated carboxylic acid in the presence of a coupling agent such as EDAC, or by the acid chloride.

Carbon-linked side-chains: 4-(phenylamino)quinazoline substituted at position 6 or 7 by iodine is converted to the corresponding arylzinc compound which is coupled with a carbon-11 labeled α,β-unsaturated carboxylic group that comprises an activated halide.

Hydrazino-linked side-chains: 4-(phenylamino)quinazoline substituted at position 6 or 7 by a nitro group is reduced to the corresponding amine, which is diazotized and then reduced to the hydrazine compound. The distal nitrogen of the hydrazine is then acylated, using methods well known to one skilled in the art, by an appropriate carbon-11 labeled α,β-unsaturated carboxylic derivative.

Hydroxylamino-O-linked side-chains: 4-(phenylamino)quinazoline substituted at position 6 or 7 by a nitro group is reduced under appropriate mildly reducing conditions to the hydroxylamine compound which is then acylated, using methods well-known to one skilled in the art, by an appropriate carbon-11 labeled α,β-unsaturated carboxylic derivative.

Methyleneamino-N-linked side-chains: 4-(phenylamino)quinazoline substituted at position 6 or 7 by a nitro group is reduced to the corresponding amine which is diazotized and then converted to nitrile, preferably in the presence of copper or nickel salt catalysis. The nitrile compound is then reduced to a methylamine compound which is acylated, using methods well known to one skilled in the art, by an appropriate carbon-11 labeled α,β-unsaturated carboxylic derivative.

Methyleneoxy-O-linked side-chains: 4-(phenylamino)quinazoline substituted at position 6 or 7 by a hydroxymethyl is produced using methods obvious to one skilled in the art. For example, 4-(phenylamino)quinazoline substituted at position 6 or 7 by a nitro group is reduced to the corresponding amine which is diazotized, converted to the nitrile as described above, partially reduced to an imine, hydrolyzed and reduced to the corresponding hydroxymethyl. The hydroxyl group is then acylated, using methods well known to one skilled in the art, by an appropriate carbon-11 labeled α,β-unsaturated carboxylic derivative.

Ethano-linked side-chains: 4-(phenylamino)quinazoline substituted at position 6 or 7 by iodine is converted, via an organozincate, to the corresponding cuprate. The cuprate is reacted with an appropriately mono-masked carbon-11 labeled divinylketone, which is then subjected to unmasking of the remaining unsaturated functionality.

Aminomethyl-C-linked side-chains: 4-phenylamino)quinazoline substituted at position 6 or 7 by a nitro group is reduced to the corresponding amine which is alkylated by a double-bond protected derivative of carbon-11 labeled 1-bromobut-3-ene-2-one. The protecting group is then removed by to methods known to one skilled in the art.

Hydroxymethyl-C-linked side-chains: 4-(phenylamino)quinazoline substituted at position 6 or 7 by a methoxy group is cleaved to the corresponding hydroxyl compound which is alkylated by a double-bond protected derivative of carbon-11 labeled 1-bromobut-3-ene-2-one. The protecting group is then removed by methods known to one skilled in the art.

Thiomethyl-C-linked side-chains: 4-(phenylamino)quinazoline substituted at position 6 or 7 by halide is converted to the corresponding mercapto compound which is then alkylated by a double-bond protected derivative of carbon-11 labeled 1-bromobut-3-ene-2-one. The protecting group is then removed by methods known to one skilled in the art.

Alternatively, carbon-11 labeled 4-(phenylamino) quinazolines having an α,β-unsaturated carboxylic side-chain are synthesized by: (i) coupling a derivatized or non-derivatized aniline with 4-chloroquinazoline that is substituted at position 6 or 7 by a reactive group, so as to produce a reactive 4-(phenylamino)quinazoline; (ii) reacting the reactive 4-(phenylamino)quinazoline with a reactive α,β-unsaturated carboxylic derivative, which is terminating with a second reactive group, so as to produce a 4-(phenylamino)quinazoline substituted at position 6 or 7 by an α,β-unsaturated carboxylic group terminating with the second reactive group; (iii) reacting the produced substituted 4-(phenylamino)quinazoline with a reactive substituted alkyl having 1–6 carbon atoms, so as to produce a 4-(phenylamino)quinazoline substituted at position 6 or 7 by the α,β-unsaturated carboxylic group terminating with the reactive substituted alkyl; and (iv) reacting, wider the appropriate conditions, the 4-(phenylamino)quinazoline substituted at position 6 or 7 by the α,β-unsaturated carboxylic group terminating with the reactive substituted alkyl with a carbon-11 labeled reactive compound.

Fluorine-18 Labeled 4-(phenylamino)quinazolines Having an α,β-unsaturated Carboxylic Side-chain (Michael Acceptor Side-chain):

A general synthetic pathway for producing fluorine-18 labeled 4-(phenylamino)quinazolines having an α,β-unsaturated carboxylic side-chain, as is presented in Scheme 2, includes the steps of: (i) preparing a fluorine-18 labeled aniline derivative by reacting a [F-18]fluoride ion with the corresponding dinitrobenzene derivative and then reducing the fluorine-18 labeled fluoronitrobenzene; (ii) reacting the fluorine-18 labeled aniline derivative with 4-chloroquinazoline that is substituted by a reactive group (L, Scheme 2, see examples below), so as to produce a reactive fluorine-18 labeled 4-(phenylamino)quinazoline; and (iii) reacting the reactive fluorine-18 labeled 4-(phenylamino)quinazoline with a reactive derivative of an α,β-unsaturated carboxylic group (X—Y(=O)-M, Scheme 2), so as to produce the fluorine-18 labeled 4-(phenylamino)quinazoline substituted at position 6 or 7 thereof by an α,β-unsaturated carboxylic side-chain.

Thus, fluorine-18 labeled 4-(phenylamino)quinazolines substituted by various α,β-unsaturated carboxylic side-chains can be synthesized according to the general pathway described above. The reactive fluorine-18 labeled 4-(phenylamino)quinazoline can be reacted with the reactive α,β-unsaturated carboxylic derivatives using the methods described hereinabove.

Radioactive Bromine Labeled and Radioactive Iodine Labeled 4-(phenylamino)quinazolines Having an α,β-Unsaturated Carboxyic Side-chain (Michael Acceptor Side-chain):

A general synthetic pathway for producing radioactive bromine labeled and radioactive iodine labeled 4-(phenylamino)-quiazolines having an α,β-unsaturated carboxylic side-chain, as is presented in Scheme 3, includes the steps of: (i) coupling an aniline that is derivatized by a halogen with 4-chloroquinazoline that is substituted by a reactive group (L, Scheme 3, see examples below), so as to produce a reactive 4-(phenylamino)quinazoline that is derivatized by a halogen; (ii) radiolabeling the reactive 4-(phenylamino) quinazoline by reacting the 4-(phenylamino)quinazoline that is derivatized by a halogen with bistributyltin, using tetrakis (triphenylphosphine)palladium as catalyst and reacting thereafter the obtained stanylated product with a radioactive bromine or a radioactive iodine, in the presence of an oxidizing agent, so as to produce a reactive radioactive bromine labeled or radioactive iodine labeled 4-(phenylamino)quinazoline; and (iii) reacting the reactive radioactive bromine labeled or radioactive iodine labeled 4-(phenylamino)quinazoline with a reactive derivative of an α,β-unsaturated carboxylic group (X—Y(=O)-M, Scheme 3), so as to produce the radioactive bromine labeled or radioactive iodine labeled 4-(phenylamino)-quinazoline substituted at position 6 or 7 thereof by an α,β-unsaturated carboxylic side-chain.

Scheme 2

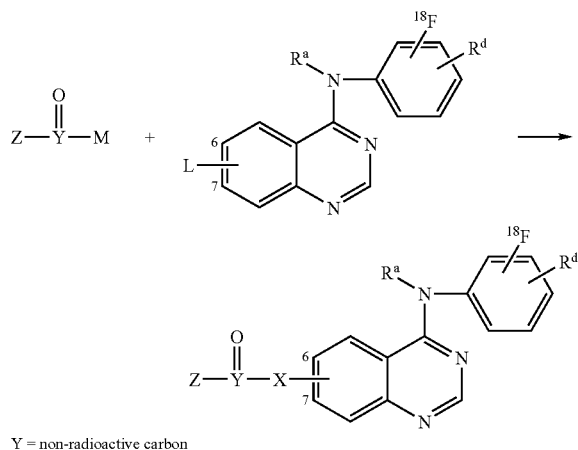

Y = non-radioactive carbon

Scheme 3

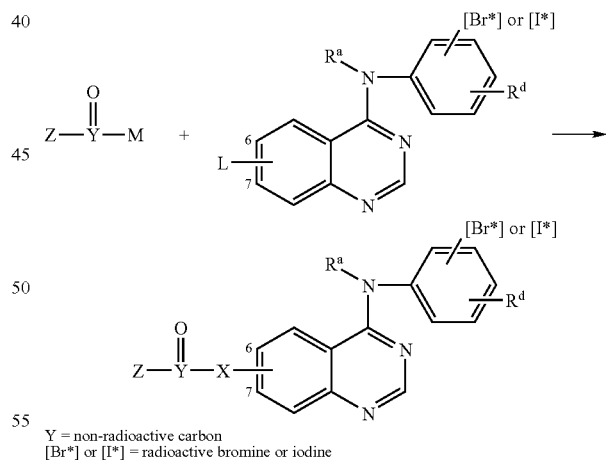

Y = non-radioactive carbon
[Br*] or [I*] = radioactive bromine or iodine

The radioactive bromine can be bromine-76 or bromine-77, and the radioactive iodine can be iodine-123, iodine-124 or iodine-131.

Thus, 4-(phenylamino)quinazolines that are radiolabeled by bromine-76, bromine-77, iodine-123, iodine-124 or iodine-131 and substituted by various α,β-unsaturated carboxylic side-chains can be synthesized according to the general pathway described above. The reactive radioactive bromine labeled or radioactive iodine labeled 4-(phenylamino)quinazoline can be reacted with the reactive α,β-unsaturated carboxylic derivatives using the methods described hereinabove.

Synthesis of α,β-unsaturated [4-(phenylamino)-quinazoline-6-yl]amides—general procedure:

(i) Aniline or derivatized aniline (1 equivalent) is reacted with 4-chloro-6-nitroquinazoline (3.5 equivalents), in a polar solvent such as iso-propyl alcohol. The product, 4-(phenylamino)-6-nitroquinazoline, is obtained after filtration.

(ii) A solution of 4-(phenylamino)-6-nitroquinazoline in ethanol/water and a polar solvent such as iso-propylalcohol is reacted at reflux temperature with hydrazine hydrate and Raney®Nickel. The reaction mixture is filtered, evaporated and purified by silica gel chromatography, to give the product, 4-(phenylamino)-6-aminoquinazoline.

(iii) 4-(Phenylamino)-6-aminoquinazoline is reacted with α,β-unsaturated acyl chloride at 0° C. in THF to give the final product in quantitative yield.

(iv) Optionally, 4-(phenylamino)-6-aminoquinazoline is reacted with α,β-unsaturated acyl chloride that is terminated with a reactive halogen group, at 0° C. in THF, in the presence of a tertiary amine, and the obtained product is then reacted with a substituted alkyl at 0° C. in THF and purified by silica gel chromatography, to give a substituted [4-(phenylamino)-quinazoline-6-yl]alkylamide, as a final product. Further optionally, the obtained product is further reacted thereafter with a reactive compound such as alkyl iodide, at 40° C., to give the final product.

Synthesis of N-{4-[(3,4-dichloro-6-fluorophenyl)amino] quinazoline-6-yl}acrylamide (Compound 3):

(i) 3,4-Dichloro-6-fluoroaniline (1 equivalent, prepared as described in U.S. Pat. No. 6,126,917) was reacted with 4-chloro-6-nitroquinazoline (3.5 equivalents, prepared by reacting 6-nitroquinazoline with thionyl chloride, according to known procedures), in iso-propylalcohol. After filtration, 4-[(3,4-dichloro-6-fluorophenyl)amino]-6-nitroquinazoline (compound 1) was obtained in 60% yield. m.p.=270–271° C.; MS (m/z): 353.2, 355.2 (M⁺); $^1$H-NMR: δ=6.97 (d, 1H), 7.345 (d, 1H), 7.885 (d, 1H), 8.405 (d, 1H), 8.554 (dd, 1H), 8.8 (d, 1H) ppm. HPLC conditions: C-18 column, 55% acetate buffer, PH=3.8/45% acetonitrile, flow=1 ml/min; r.t.=7.15 minutes.

(ii) A solution of 4-[(3,4-dichloro-6-fluorophenyl)amino]-6-nitroquinazoline (709 mg, 2.076 mmol) in 140 ml of 1:9:10 water:ethanol:iso-propylalcohol was heated to reflux temperature (95° C.). Additional 60 ml of the solvents mixture was added until complete dissolution. The reaction mixture was then cooled to 65° C., and 200 µl hydrazine hydrate (4.12 mmol) and 0.5 ml Raney®Nickel (in water) were added subsequently thereto. The resulting mixture was heated up to 80–85° C., additional 0.5 ml Raney®Nickel and 50 µl of hydrazine hydrate (1.03 mmol) were added, and gentle reflux was maintained for about 15–20 minutes. Filtration and evaporation gave 4-[(3,4-dichloro-6-fluorophenyl)amino]-6-aminoquinazoline (compound 2) in 83% yield. m.p.=265° C.; MS (m/z): 323.4, 325.4 (M⁺); Anal. calcd.: C, 52.9; H, 2.78; N, 17.33. Found: C, 52.19; H, 2.99; N, 17.14. HPLC analysis. C-18 column, 55% acetate buffer, PH=3.8/45% acetonitrile, flow=1 ml/min; r.t=6.6 minutes.

(iii) Acryloyl chloride was reacted with 4-[(3,4-dichloro-6-fluorophenyl)amino]-6-aminoquinazoline in THF, at 0° C. The final product was obtained in quantitative yield.

Synthesis of N-{4-[(3,4-dichloro-6-fluorophenyl)amino]-7-[3-(4-morpholinyl)propoxy]quinazoline-6-yl}acrylamide (morpholino-substituted Compound 3):

(i) 3,4-Dichloro-6-fluoroaniline (1 equivalent) was reacted with 4-chloro-7-fluoro-6-nitroquinazoline (3.5 equivalents), in iso-propylalcohol. After filtration, 4-[(3,4-dichloro-6-fluorophenyl)amino]-7-fluoro-6-nitroquinazoline was obtained in 78% yield.

(ii) Sodium metal (5 equivalents) was added, under nitrogen atmosphere, to a solution of 3-(4-morpholinyl)-1-propanol (4 equivalents) in THF. The obtained suspension was stirred at 20° C. for two hours and was thereafter cannulated, under nitrogen atmosphere, into a solution of 4-[(3,4-dichloro-6-fluorophenyl)amino]-7-fluoro-6-nitroquinazoline. The reaction mixture was refluxed for 18 hours, the solvent was thereafter partially removed under reduced pressure and the residue was diluted with water and extracted with ethyl acetate. Drying the combined organic extracts, evaporation and silica gel chromatography (using a mixture of 20% MeOH/30% CH$_2$Cl$_2$/50% EtOAc as elute) gave 4-[(3,4-dichloro-6-fluorophenyl)amino]-7-[3-(4-morpholinyl)propoxy]-6-nitroquinazoline in 72% yield.

(iii) 4-[(3,4-dichloro-6-fluorophenyl)amino]-7-[3-(4-morpholinyl)propoxy]-6-nitroquinazoline was reacted with hydrazine hydrate and Raney®Nickel, as described hereinabove, to produce 6-amino-4-[(3,4-dichloro-6-fluorophenyl)amino]-7-[3-(4-morpholinyl)propoxy]quinazoline in 75% yield.

(iv) Acryloyl chloride was reacted with 6-amino-4-[(3,4-dichloro-6-fluorophenyl)amino]-7-[3-(4-morpholinyl)propoxy]quinazoline in THF, at 0° C. The final product was obtained in quantitative yield.

Synthesis of N-{4-[(3,4-dichloro-6-fluorophenyl)amino] quinazoline-6-yl}-4-(dimethylamino)-2-butenamide (Compound 4):

(i) Oxalyl chloride (33 mmol) was added to a suspension of 4-bromocrotonic acid (15 mmol, prepared by reacting methyl 4-bromocrotonate with barium oxide in the presence of concentrated H$_2$SO$_4$) in CH$_2$Cl$_2$ (25 ml). Three drops of DMF were added and the mixture was stirred for 1.5 hours. The solvents were thereafter removed under reduced pressure and the residual oil was dissolved in THF (20 ml). The solution was cooled in an ice bath and a solution of 4-[(3,4-dichloro-6-fluorophenyl)amino]-6-nitroquinazoline (compound 1), prepared as described hereinabove, in THF (50–100 ml) was added dropwise. A solution of N,N-diisopropylamine (15 mmol) in THF (10 ml) was then added and the reaction mixture was cooled and stirred for one hour. Ethyl acetate (80 ml) and water (100 ml) were thereafter added, the layers were separated and the organic layer was washed with brine, dried over sodium sulfate and evaporated 4-Bromo-N-{4-(3,4-dichloro-6-fluorophenyl)amino] quinazoline-6-yl}-2-butenamide, as an inseparable mixture with the 4-chloro product in a typical ratio of 4:1 to 5:1, was obtained in 66% yield. MS (m/z): 425 (M+)⁺, 471 (MH+)⁺; $^1$H-NMR (DMSO-d$_6$): δ=1.37 (s, 2H), 2.33 (d, 1H), 4.62 (dd, 2H), 6.69 (d, 1H), 7.19 (dt, 1H), 8.10 (mt, 4H) 8.72 (s, 1H), 9.08 (s, 1H), 10.24 (s, 1H), 10.87 (s, 1H) ppm; Anal. Calc: C, 46.47; H, 2.60; N, 12.04. Found: C, 47.31; H, 3.2; N, 11.57. HPLC analysis: C-18 column, 55% acetate buffer/ 45% acetonitrile, flow=1.5 ml/min; r.t.=19.5 minutes (first peak), 21.9 minutes (second peak).

(ii) To a stirred solution of 4-bromo-N-{4-(3,4-dichloro-6-fluorophenyl)amino]quinazoline-6-yl}-2-butenamide (564 mg, 1.28 mmol) in dry THF (120 ml) dimethylamine (2 M in THF, 38 ml) was added dropwise and the reaction mixture was heated at 80° C. for 15 minutes. Ethyl acetate (50 ml) and saturated NaHCO$_3$ (50 ml) were thereafter added and the layers were separated. Washing the organic layer with brine, drying over magnesium sulfate, evaporation and purification by silica gel chromatography (using 5% MeOH/95% $CH_2Cl_2$ as eluent) gave the product in 73% yield (317 mg). MS (m/z): 434.1 (MH+); $^1$H-NMR (DMSO-$d_6$): δ=2.18 (s, 6H), 3.08 (d, 2H), 3.92 (s, 1H), 6.36 (d, 1H), 6.86 (dt, 1H), 7.22 (mt, 4H), 7.76 (d, 2H), 7.86 (dd, 1H), 7.92 (dd, 1H), 8.83 (s, 1H) 10.47 (s, 1H); Anal. calcd.: C, 55.31; H, 4.18; N, 16.13. Found: C, 54.48; H, 4.85; N, 15.36. HPLC analysis: C-18 column, 45% acetate buffer, PH=3.8/ 55% acetonitile, flow=1 ml/min; r.t.=6.65 minutes.

Synthesis of N-{4-[(3-iodophenyl)amino]quinazoline-6-yl}-4-(dimethylamino)-2-butenamide (Compound 5):

(i) 3-Iodoaniline (12.57 grams, 57 mmol) was reacted with 4-chloro-6-nitroquinazoline (4 grams, 57 mmol), in iso-propylalcohol, as is described hereinabove, to give 4-[(3-iodophenyl)amino]-6-nitroquinazoline (5.99 grams, 78% yield), which was thereafter reacted (620 mg, 1.58 mmol) with hydrazine hydrate and Raney®Nickel, according to the procedure described hereinabove, to give 4-[(3-iodophenyl) amino]-6-aminoquinazoline (180 mg, 31% yield).

(ii) A solution of 4-[(3-iodophenyl)amino]-6-aminoquinazoline was reacted with bromocrotonic acid and dimethylamine, as is described hereinabove in Compound 4, to give N-{4-[(3-iodophenyl)amino]quinazoline-6-yl}-4-(dimethylamino)-2-butenamide. MS (m/z): 465 (M+H)$^+$, 509 (M+)$^+$; $^1$H-NMR (DMSO-$d_6$): δ=4.38 (d, 1H), 4.49 (d, 1H), 6.5 (dd, 1H), 6.94 (dt, 1H), 7.19 (t, 1H), 7.47 (d, 1H), 7.85 (mt, 3H), 8.27 (s, 1H), 8.58 (s, 1H), 8.82 (s, 1H) 10.59 (s, 1H); Anal. Calc: C, 42.46; H, 2.77; N, 11.0. Found: C, 46.52; H, 3.04; N, 12.06. HPLC analysis: C-18 column, 55% acetate buffer/45% acetonitrile, flow=1.0 ml/min; r.t.=26.55 minutes (first peak), 29.99 minutes (second peak).

Synthesis of N-{4-[(3-iodophenyl)amino]quinazoline-6-yl}-4-(methylamino)-2-butenamide (Compound 5a):

N-{4-[(3-iodophenyl)amino]quinazoline-6-yl}-4-(methylamino)-2-butenamide was prepared as described above in Compound 5, using methylaniline instead of dimethylamine in step (ii).

Synthesis of N-{4-[(3-bromophenyl)amino]quinazoline-6-yl}-4-(methylamino)-2-butenamide (Compound 6):

(i) 3-Bromoaniline (1.72 grams, 10 mmol) was reacted with 4-chloro-6-nitroquinazoline (523 mg, 2.5 mmol), in iso-propylalcohol, as is described hereinabove, to give 4-[(3-bromophenyl)amino]-6-nitroquinazoline (823 mg, 95% yield), which was thereafter reacted (590 mg, 1.7 mmol) with hydrazine hydrate, according to the procedure described hereinabove, to give 4-[(3-bromophenyl)amino]-6-aminoquinazoline (332 mg, 62% yield).

(ii) 4-[(3-bromophenyl)amino]-6-aminoquinazoline is reacted with bromocrotonic acid and dimethylamine, as is described hereinabove in Compound 5, to give N-{4-[(3-bromophenyl)amino]quinazoline-6-yl}4-(dimethylamino)-2-butenamide.

Synthesis of carbon-11 labeled α,β-unsaturated [4-(phenylamino)quinazoline-6-yl]acrylamides—general procedure:

The radiosynthesis is carried out by a fully automated route using the Nuclear Interface MeI module, carbon-11 $CO_2$ (Approx. 700 mCi) is trapped at −160° C., and transferred thereafter, using a stream of argon, to a first reactor that contains vinyl magnesium bromide in THF (90% trapping efficiency). Addition of phtaloyl dichloride and ditert-butylpyridine gives the carbon-11 labeled acryloyl chloride. The labeled acryloyl chloride is distilled during 4 minutes at 100° C., using a stream of argon (20–30 ml/min) to a second reactor, which contains 300 μl of THF at −50° C. At the end of the distillation the temperature is raised to 10° C., and a solution of 5–7 mg of 4-(phenylamino)-6-aminoquinazoline in 300 μl of anhydrous THF is added thereto. After two minutes, 600 μl of a HPLC solvent (such as 48% $CH_3CN$ in 52% acetate buffer pH=3.8) is added and the solution is injected to HPLC (C18-reverse phase-prep Column, 15 ml/min. flow rate). The product is collected into a solid phase extraction vial containing 50 ml of water and 1 ml of 1 M NaOH. The solution is passed through an activated, pre-washed (with 10 ml water) C18 cartridge, and washed with 10 ml sterile water. The product is eluted using 1 ml of ethanol followed by 5 ml of saline and collected in a sterile product vial in 18% decay-corrected (EOB) radiochemical yield. Overall synthesis time, including purification, is 35 minutes.

Synthesis of carbon-11 labeled N-{4-[(3,4-dichloro-6-fluorophenyl)amino]quinazoline-6-yl}acrylamide (carbon-11 labeled Compound 3):

Carbon-11 labeled acryloyl chloride was obtained by the general procedure described hereinabove, and was reacted for two minutes with 5–7 mg of 4-[(3,4-dichloro-6-fluorophenyl)amino]-6-aminoquinazoline. HPLC solvent (600 μl of 48% $CH_3CN$ and 52% acetate buffer pH=3.8) was added thereafter, and the solution was injected to HPLC apparatus as described hereinabove. The retention time of the product was 22 minutes. The product was collected, passed through the activated, water-washed, C18 cartridge and collected in a sterile product vial in 18% decay-corrected (EOB) radiochemical yield. The radiochemical purity thereof was analyzed by reverse phase HPLC (μ Bondapak analytical column), using 40% $CH_3CN$ in 60% acetate buffer (pH=3.8) as elute, at a flow rate of 1.7 ml/min (retention time was 11.7 minutes), and found to be 100%, SA of 1700 Ci/mmol.

Synthesis of carbon-11 labeled N-{4-[(3-bromo/iodophenyl)amino]quinazoline-6-yl}acrylamide:

Carbon-11 labeled acryloyl chloride is obtained by the general procedure described hereinabove, and is reacted with 4-[(3-bromo/iodophenyl)amino]-6-aminoquinazoline, according to the procedure described hereinabove.

Synthesis of carbon-11 labeled N-{4-[(3,4-dichloro-6-fluorophenyl)amino]-7-[3-(4-morpholinyl)propoxy]quinazoline-6-yl}acrylamide (carbon-11 labeled morpholino-substituted Compound 3):

Carbon-11 labeled acryloyl chloride is obtained by the general procedure described hereinabove, and is reacted with 6-amino-4-[(3,4-dichloro-6-fluorophenyl)amino]-7-[3-(4-morpholinyl)propoxy]quinazoline, according to the procedure described hereinabove.

Synthesis of carbon-11 labeled N-{4-[(3-bromo/iodophenyl)amino]-7-([3-(4-morpholinyl)propoxy]quinazoline-6-yl}acrylamide:

Carbon-11 labeled acryloyl chloride is obtained by the general procedure described hereinabove, and is reacted with 6-amino-4-[(3-bromo/iodophenyl)amino]-7-[3-(4-morpholinyl)propoxy]quinazoline, according to the procedure described hereinabove.

Synthesis of carbon-11 labeled α,β-unsaturated [4-(phenylamino)quinazoline-6-yl]-4-(dimethylamino)-2-butenamide—general procedure:

Carbon-11 labeled methyl iodide is generated, by a well-known procedure [20], in a first reactor and is thereafter distilled, during 2–3 minutes, into a second reactor containing 3 milligrams of a substituted [4-(phenylamino)-quinazoline-6-yl]alkylamide, obtained by the general procedure described hereinabove. At the end of the distillation, the second reactor is sealed and heated at 140° C. for several minutes. A HPLC solvent is thereafter added thereto and the mixture is separated on reversed-phase HPLC column. The product is diluted with water and collected by a solid phase extraction.

Synthesis of carbon-11 labeled α,β-unsaturated N-{4-[3,4-dichloro-6-fluorophenylamino)quinazoline-6-yl]-4-(dimethylamino)-2-butenamide (carbon-11 labeled Compound 4):

4-Bromo-N-{4-(3,4-dichloro-6-fluorophenyl)amino]quinazoline-6-yl}-2-butenamide (0.0258 mmol), obtained as described hereinabove, was dissolved in dry DMSO in a closed test tube. Methylamine (20M in THF, 1 ml) was quickly added and the reaction mixture was immediately cooled in ice-water bath (0° C.) for 12–15 minutes. 1.0 M NaOH in water (10 ml) was then added and the mixture was stirred for two minutes The resulting aqueous solution was slowly filtered trough two activated C-18 Seppak (8 ml EtOH followed by 10 ml water). The C-18 Seppaks were thereafter dried by means of nitrogen stream (10 minutes), and the product was thereafter rinsed out with dry THF (4 ml). The THF solution was dried with sodium sulfate, filtered and evaporated under nitrogen stream. The obtained N-{4-(3,4-dichloro-6-fluorophenyl)amino]quinazoline-6-yl}-4-(methylamino)-2-butenamide was reacted, without further purification, with carbon-11 labeled methyl iodide according to the general procedure described hereinabove.

Synthesis of fluorine-18 labeled α,β-unsaturated [4-(phenylamino)quinazolin-6-yl]acrylamides—general procedure:

The Kryptofix®2.2.2—potassium $^{18}$F-fluoride—DMSO solution described above is added to 2–3 mg of a preselected dinitrobenzene in a screw-top test tube (8 ml, Corning). The tube is capped, shaken and heated in a microwave for 3.5 minutes. The tube is cooled in an ambient water bath, and the contents thereof are diluted with 10 ml of water and loaded onto an activated (ethanol) and equilibrated (water) C18 Sep-Pak (classic, short body, Waters). The cartridge is washed with water (10 ml) and the desired corresponding intermediate, fluorine-18 labeled fluoronitrobenzene, is eluted with ethanol (2 ml) into a small glass test tube. The reduction vessel is prepared by adding to a flat-bottomed glass vial (25 ml), sequentially, a few borosilicate glass beads, 100 μl 4:1 ethanol-water, 250 μl Raney®Nickel slurry, and 60 μl hydrazine monohydrate. After capping with a septum-equipped screw cap (vented with a large diameter needle) the vial is shaken and placed in a 40° C. heating block. The ethanolic fluorine-18 labeled fluoronitrobenzene solution is diluted with 0.5 ml water and added slowly to the reduction vessel. After 5 minutes, the vessel is cooled in an ambient water bath, and the vial content is filtered through a 0.45 μl m filter (Puradisc, polypropylene, Whatman) into another flat-bottomed 25 ml vial. Eight ml of water and 10 ml of ether are then added to the filtered solution, and by capping and inverting several times to mix, the corresponding fluorine-18 labeled fluoroaniline reduction product is extracted into the ether layer. An 8 ml screw-top test tube is then charged with a solution of 4–5 mg of a 4-chloro-6-nitroquinazoline in 300 μl 2-propanol. The ethereal radiolabeled aniline solution is added to the tube by passing it through MgSO$_4$ (2 grams) and a new 0.45 μm filter. The ether is removed under a stream of helium, while warming the tube in an ambient water bath. Concentrated HCl (1 μl) is added thereafter and the capped tube is heated in a 110° C. oil bath for 15 minutes. After cooling the tube in ambient water, the acid is neutralized and the free base is liberated with the addition of 50 μl of 5M NaOH. Dichloromethane (0.3 ml) and hexane (0.3 ml) are added to the tube and the solution is filtered through a 0.2 μm filter (Acrodisc, nylon. Gelman). The fluorine-18 labeled 4-[(fluorophenyl)amino]-6-nitroquinazoline is purified by silica SEP-PAK and reduced to obtain the amine derivative thereof, which is further reacted with acryloyl chloride as described herein.

Synthesis of fluorine-18 labeled N-{4-[(3,4-dichloro-6-fluorophenyl)amino]quinazoline-6-yl}acrylamide (fluorine-18 labeled Compound 3):

Fluorine-18 labeled 4-[(3,4-dichloro-6-fluorophenyl)amino]-6-nitro quinazoline (compound 1) was obtained by the radiosynthesis procedure described hereinabove, using 2–3 mg of 1,2-dichloro-4,5-dinitrobenzene in the reaction with the $^{18}$F-fluoride ion to provide 1,2-dichloro-4-$^{18}$F-fluoro-5-nitrobenzene, which was reduced to the corresponding aniline and reacted with 4-chloro-6-nitroquinazoline as described. The fluorine-18 labeled 4-[(3,4-dichloro-6-fluorophenyl)amino]-6-nitroquinazoline was further reacted as described to yield the final fluorine-18 labeled product.

Synthesis of fluorine-18 labeled N-{4-[(3,4-dichloro-6-fluorophenyl)amino]-7-[3-(4-morpholinyl)propoxy]quinazoline-6-yl}acrylamide (fluorine-18 labeled morpholino-substituted Compound 3):

Fluorine-18 labeled 4-[(3,4-dichloro-6-fluorophenyl)amino-]7-fluoro-6-nitroquinazoline is obtained by the radiosynthesis procedure described hereinabove, using 1,2-dichloro-4,5-dinitrobenzene in the reaction with the $^{18}$F-fluoride ion to provide 1,2-dichloro-4-$^{18}$F-fluoro-5-nitrobenzene, which is reduced to the corresponding aniline. The obtained aniline is reacted with 4-chloro-7-fluoro-6-nitroquinazoline as described. The fluorine-18 labeled 4-[(3,4-dichloro-6-fluorophenyl)amino]-7-fluoro-6-nitroquinazoline is then reacted with the sodium salt of 3-(4-morpholinyl)-1-propanol as described hereinabove and the fluorine-18 labeled 4-[(3,4-dichloro-6-fluorophenyl) amino]-7-[3-(4-morpholinyl)propoxy]-6-nitroquinazoline is further reduced to the corresponding aminoquinazoline and reacted with acryloyl chloride as described to yield the final fluorine-18 labeled product.

Synthesis of fluorine-18 labeled N-{4-[(3,4-dichloro-6-fluorophenyl)amino]quinazoline-6-yl}4-(dimethylamino)-2-butenamide (fluorine-18 labeled Compound 4):

Fluorine-18 labeled 4-[(3,4-dichloro-6-fluorophenyl) amino]-6-nitro quinazoline (compound 1) is obtained by the radiosynthesis procedure described hereinabove, using 1,2-dichloro-4,5-dinitrobenzene in the reaction with the $^{18}$F-fluoride ion to provide 1,2-dichloro-4-$^{18}$F-fluoro-5-nitrobenzene, which is reduced to the corresponding aniline and reacted with 4-chloro-6-nitroquinazoline as described. The fluorine-18 labeled 4-[(3,4-dichloro-6-fluorophenyl) amino]-6-nitroquinazoline is reduced to the corresponding fluorine-18 labeled 6-aminoquinazoline, which is farther reacted with 4-bromocrotonyl chloride (obtained by reacting oxalyl chloride and 4-bromocrotonic acid) and dimethylamine, as described, to yield the final fluorine-18 labeled product.

Synthesis of bromine-76 labeled and bromine-77 labeled N-{4-[(3-bromophenyl)amino]quinazolin-6-yl}acrylamide:

3-Bromoaniline is coupled with 4-chloro-6-nitroquinazoline, to produce 4-[(3-bromophenyl)amino]-6-nitroquinazoline, which is reduced thereafter to the corresponding 6-aminoquinazoline. The 4-[(3-bromophenyl)amino]-6-aminoquinazoline is then reacted with bistributyltin, using tetrakis(triphenylphosphine)palladium in THF solution as the reaction catalyst, as is described hereinbelow (see, iodine-124 labeled Compound 5). The stanylated quinazoline is then reacted with bromine-76 or bromine-77, in the presence of an oxidizing agent, to produce bromine-76 labeled or bromine-77 labeled 4-[(3-bromophenyl)amino]-6-aminoquinazoline, which is farther reacted with acryloyl chloride as described, to yield the final bromine-76 labeled or bromine-77 labeled product.

Synthesis of bromine-76 labeled and bromine-77 labeled N-{4-[(3-bromophenyl)amino]-7-[3-(4-morpholinyl)propoxy]quinazoline-6-yl}acrylamide:

3-Bromoaniline is coupled with 4-chloro-7-fluoro-6-nitroquinazoline, to produce 4-[(3-bromophenyl)amino]-7-fluoro-6-nitroquinazoline, which is reacted thereafter with the sodium salt of 3-(4-morpholinyl)-1-propanol, as described hereinabove, to produce 4-[(3-bromophenyl)amino]-7-[3-(4-morpholinyl)propoxy]-6-nitroquinazoline. The morpholino-substituted 6-nitroquinazoline is then reduced to the corresponding 6-aminoquinazoline, which is further reacted with bistributyltin, bromine-76 or bromine-77 and acryloyl chloride, as described hereinabove, to yield the final bromine-76 labeled or bromine-77 labeled product.

Synthesis of bromine-76 labeled and bromine-77 labeled N-{4-[(3-bromophenyl)amino]quinazoline-6-yl}4-(dimethylamino)-2-butenamide (bromine-labeled Compound 6):

3-Bromoaniline is coupled with 4-chloro-6-nitroquinazoline, to produce 4-[(3-bromophenyl)amino]-6-nitroquinazoline, which is reduced thereafter to the corresponding 6-aminoquinazoline, as described. The 4-[(3-bromophenyl)amino]-6-aminoquinazoline is then reacted with bistributyltin, using tetrakis(triphenylphosphine)palladium in THF solution as the reaction catalyst, as is described hereinbelow. The stanylated quinazoline is then reacted with bromine-76 or bromine-77, in the presence of an oxidizing agent, to produce bromine-76 labeled or bromine-77 labeled 4-[(3-bromophenyl)amino]-6-aminoquinazoline, which is further reacted with 4-bromocrotonyl chloride (obtained by reacting oxalyl chloride and 4-bromocrotonic acid) and dimethylamine, as described, to yield the final bromine-76 labeled or bromine-77 labeled product.

Synthesis of iodine-123 labeled, iodine-124 labeled and iodine-131 labeled N-{4-[(3-iodophenyl)amino]quinazolin-6-yl}acrylamide:

3-Bromoaniline is coupled with 4-chloro-6-nitroquinazoline, to produce 4-[(3-bromophenyl)amino]-6-nitroquinazoline, which is reduced thereafter to the corresponding 6-aminoquinazoline. The 4-[(3-bromophenyl)amino]-6-aminoquinazoline is then reacted with bistributyltin, using tetrakis(triphenylphosphine)palladium in triethylamine solution as the reaction catalyst. The stanylated quinazoline is then reacted with iodine-123, iodine-124 or iodine-131, in the presence of an oxidizing agent, to produce iodine-123 labeled, iodine-124 or iodine-131 labeled 4-[(3-bromophenyl)amino]-6-aminoquinazoline, as is described hereinbelow, which is further reacted with acryloyl chloride as described, to yield the final iodine-123 labeled, iodine-124 labeled or iodine-131 labeled product.

Synthesis of iodine-123 labeled, iodine-124 labeled and iodine-131 labeled N-{4-[(3-iodophenyl)amino]-7-[3-(4-morpholinyl)propoxy]quinazoline-6-yl}acrylamide:

3-Bromoaniline is coupled with 4-chloro-7-fluoro-6-nitroquinazoline, to produce 4-[(3-bromophenyl)amino]-7-fluoro-6-nitroquinazoline, which is reacted thereafter with the sodium salt of 3-(4-morpholinyl)-1-propanol, as described hereinabove, to produce 4-[(3-bromophenyl)amino]-7-[3-(4-morpholinyl)propoxy]-6-nitroquinazoline. The morpholino-substituted 6-nitroquinazoline is then reduced to the corresponding 6-aminoquinazoline, which is further reacted with bistributyltin, iodine-123, iodine-124 or iodine-131 and acryloyl chloride, as described hereinabove, to yield the final iodine-123 labeled, iodine-124 labeled or iodine-131 labeled product.

Synthesis iodine-124 labeled N-{4-[(3-iodophenyl)amino]quinazoline-6-yl}4-(dimethylamino)-2-butenamide (iodine-124 labeled Compound 5):

(i) 3-Bromoaniline was coupled with 4-chloro-6-nitroquinazoline, to produce 4-[(3-bromophenyl)amino]-6-nitroquinazoline, which was reduced thereafter to the corresponding 6-aminoquinazoline. 4-[3-Bromophenyl)amino]-6-aminoquinazoline (300 mg, 0.95 mmol) was dissolved in dry THF (20 ml) and bistributyltin (1.92 ml, 3.78 mmol), followed by tetrakis(triphenylphosphine)palladium (547.8 mg, 0.474 mmol) in dry THF (0.5 ml), were then added and the reaction mixture was gently refluxed for 16 hours. Evaporation of the solvent, followed by purification on aluminium oxide 90 column (70–230 mesh), using a gradient eluent of from 20:80 hexane:dichloromethane to 100% dichloromethane gave the stanylated product 4-[(3-tributyltinphenyl)amino]-6-aminoquinazoline (85 mg, 20% yield). MS (m/z): 527 (M+2H)$^+$; $^1$H-NMR (CDCl$_3$): δ=0.91 (t, 9H), 1.07 (t, 6H), 1.31 (dt, 6H), 1.58 (mt, 6H), 6.95 (d, 1H), 7.19 (d, 1H), 7.22 (d, 1H), 7.37 (dd, 1H), 7.66 (d, 1H), 7.74 (d, 1H) 8.59 (s, 1H), 10.42 ppm.

(ii) 4-[(3-Tributyltinphenyl)amino]-6-aminoquinazoline (4 mg) was dissolved in EtOH (1 ml), in a conic vial, and [I-124]NaI, obtained as described above, in 0.1N NaOH (15 μl) was added thereto. 0.1N HCl (150 μl) and chloramine-T (1 mg/1 ml, 150 μl) were then added and the reaction mixture was stirred at room temperature for 15 minutes. Sodium metylbisulfite (200 mg/ml, 0.5 ml) was thereafter added, followed by addition of saturated solution of NaHCO$_3$ (2 ml) and saline (4 ml). The resulting aqueous solution was stirred with vortex and thereafter filtered on C-18 Seppak. The Seppak was rinsed with water (5 ml) and was thereafter dried under nitrogen stream for 10 minutes. The product was rinsed out with dry THF (4 ml). The yield was measured by evaporating the THF so as to obtain a 200 μl solution and injecting the resulting solution to HPLC preparative C-18 column, using 55% acetate buffer/45% acetonitrile, flow=1.0 ml/min; r.t.=7.18 minutes. 45% yield of the labeled compound was obtained.

(iii) A solution of iodine-124 labeled 4-[(3-iodophenyl)amino]-6-aminoquinazoline in THF (about 1 ml) in a conic vial was cooled at 0° C. for 10 minutes and 0.5 ml solution of Br/Cl-crotonylchloride in dry THF (182 mg in 3 ml) was added thereto. The reaction solution was stirred 30–40 minutes at 0° C., water was added and the solution was filtered on C-18 Seppak. The product was dried under nitrogen stream for 10 minutes and was rinsed out with dry THF (2 ml). The yield was measured by HPLC preparative C-18 column, 55% acetate buffer/45% acetonitrile, flow=1.0 ml/min; r.t.=26.55 minutes (first peak), 29.99 minutes (second peak). 30% yield of the labeled compound was obtained.

(iv) The labeled compound was dissolved in dry THF (about 2 ml), the solution was cooled for 10 minutes at 0° C. and dimethylamine (2.0M in THF, 1 ml) was added at once. The reaction mixture was stirred at 0° C. for 40 minutes. The yield was measured by HPLC preparative C-18 column, 55% acetate buffer/45% acetonitrile, flow=1.0 ml/min; r.t.=4.71 minutes. 30% yield of the final iodine-labeled compound 4 was obtained.

Synthesis of iodine-123 labeled and iodine-131 labeled N-{4-[(3-iodophenyl)amino]quinazoline-6-yl}4-(dimethylamino)-2-butenamide:

3-Bromoaniline is coupled with 4-chloro-6-nitroquinazoline, to produce 4-[(3-bromophenyl)amino]-6-nitroquinazoline, which is reduced thereafter to the corresponding 6-aminoquinazoline. The 4-[(3-bromophenyl)amino]-6-aminoquinazoline is then reacted with bistributyltin, using tetrakis(triphenylphosphine)palladium in triethylamine solution as the reaction catalyst, as is described hereinabove. The stanylated quinoline is then reacted with iodine-123 or iodine-131, in the presence of an oxidizing agent, to produce iodine-123 labeled or iodine-131 labeled 4-[(3-iodophenyl)amino]-6-aminoquinazolie, which is further reacted with 4-bromocrotonyl chloride and dimethylaniline, as described, to yield the final iodine-123 or iodine-131 labeled product.

In Vitro Activity Assays:

Autophosphorylation Inhibition Experiments in A431 Cell Lysate:

EGFR-TK source; As a source of EGFR-TK, A431 human epidermoid carcinoma cell lysate was used. A431 cells were grown in DMEM containing 10% fetal calf serum and antibiotics (penicillin and streptomuycin). After several days, the cells were removed from the flasks by incubation at 37° C. with PBS/1 mM EDTA buffer for 1 hour. The pellet obtained with centrifugation of the cell suspension (600 g×5 minutes at room temperature) was then resuspended in lysis buffer (0.02 M Hepes pH 7.4, 0.125 M NaCl, 1% Triton X-100, 10% glycerol) and left in ice for 10 minutes. Cell lysate was obtained with a further centrifugation (10,000 rpm×10 minutes at 4° C.), and the supernatant was collected and frozen at −70° C. in aliquots.

ELISA assay: EGFR-TK autophosphorylation $IC_{50}$ values were obtained by means of an ELISA assay. All the following incubations were performed at room temperature and with constant shaking. After each step the plate was washed with water (×5) and TBST buffer (×1). The final volume for each well was 150 µl.

A Corning 96 well ELISA plate was coated with monoclonal anti EGFR antibody m108 (Sugen Inc.) diluted in PBS (pH 8.2), and kept overnight at 4° C. After removing the unbound m108, the plate was washed and PBS containing 5% milk (1% fat) was added for the blocking (25 minutes).

One aliquot of A431 cell lysate was thawed and added to the plate. The amount of lysate was defined according to a previous test performed without inhibitors for the definition of the best ratio between the amount of m108 and the amount of EGFR-TK in A431 cell lysate.

After 25 minutes, seven different concentrations of each inhibitor were added, and for each case one well was left as a zero-inhibition control (no inhibitor) and one well was left as a zero-EGFR-TK control (no lysate). The inhibitors were diluted in TBS/DMSO and the final concentration of DMSO was 0.05% in each well (including the controls).

After 25 minutes, and without washing the plate, ATP/$MnCl_2$ solution was added in each well. The final concentration was 3 µM ATP/5 mM $MnCl_2$. In this step the temperature was kept at 26° C. and the plate was under constant shaking. The incubation with ATP/$MnCl_2$ was for 5 minutes.

Then, to stop the phosphorylation reaction, EDTA was added (pH 8, final concentration in each well 20 mM) and after 1 minute all the plate was washed.

Afterward, polyclonal anti-phosphotyrosine serum (Sugen, Inc.) was added (dilution of antibody in TBST containing 5% milk). The incubation was for 45 minutes.

For the colorimetric detection of phosphotyrosine in EGFR-TK, TAGO anti-rabbit peroxidase conjugate antibody (Sugen, Inc.) was added in TBST/5% milk solution (45 minutes).

After washing, the colorimetric reaction was performed by adding ABTS/$H_2O_2$ in citrate-phosphate buffer. After 5–10 minutes the plate was read on Dynaytec MR 5000 ELISA reader at 405 nm. The analysis of the data was performed using GraphPad Prism, version 2.01 (Graph[ad Software, Inc.).

Autophosphorylation Inhibition Experiments in Intact A431 Cells:

A431 cells ($10^6$) were seeded in 6-well plates and grown to 60–80% confluence in DMEM (high glucose) containing 10% fetal calf serum (FCS) and antibiotics at 37° C. The cells were then exposed to serum-free medium, at 37° C., for 18 hours.

Irreversibility assay: Variable concentrations of the inhibitor, ranging from 0.05 nM to 50 nM, were added to A431 cells for 2 hours incubation. The inhibitor was diluted in vehicle/DMSO and the final concentration of DMSO was 0.05% in each well). The medium was replaced thereafter with an inhibitor/FCS-free medium and the cells were left for either 2 or 8 hours, at 37° C. During the 8 hours period, the medium was changed three more times. After the post-incubation period, the cells were stimulated with EGF (20 ng/ml) for 5 minutes and then washed with PBS. Whole-cell lysates were obtained by scraping the cells into the well with 0.4 ml of Leammli buffer (10% glycerol, 3% sodium dodecyl sulfate, 5% b-mercaptoethanol, 50 mM Tris pH 6.8) that contained 0.001% bromophenol blue, and boiling for 5 minutes. The samples were kept at −20° C., prior to the protein determination assay described herein below.

EGFR autophosphorylation inhibition rate measurements: A431 cells ($6\times10^5$) were incubated with the inhibitor at room temperature for different times, ranging from 1 minute to 10 minutes. After the incubation, the medium was replaced with an inhibitor/FCS-free medium, the cells were kept at 37° C. for either 1 or 8 hours, stimulated thereafter with EGF and lysated as described hereinabove. The protein determination assay was then performed once with n=1 for each time point of the 1 hour post-incubation set of cells left, and with n=2 (for each time point) for the 8 hours post-incubation set of cells.

Protein determination assay: The amount of protein in each lysate was determined by a filter paper assay: Aliquots (3 ml) from each extract were loaded onto a strip (1×3 cm) of Whatman blotting paper and immersed into filtered dye-ing solution (0.25% comassie blue, 40% MeOH, 10% acetic acid) for 20 minutes at room temperature with gentle shaking. The strips were then washed (3×15 minutes) with fading solution (20% MeOH, 7% acetic acid) and dried. Each strip was extracted by constant shaking in sodium dodecyl sulfate solution (3%, 500 ml, 37° C.). After 1 hour the eluted samples were transferred to 96-well plates and read at 595 nm in a microplate reader (ELX 800, Biotek Instruments, Inc.). A standard curve was prepared using BSA (1 mg/ml).

Western blots: Identical protein amounts from each lysate sample were loaded onto polyacrylamide gel (6% or 10%), separated by electrophoresis (Hoefer Pharmacia Diotech Inc., San Francisco, USA) and transferred to nitrocellulose membrane (power supply: EPS 500/400, Amersham Pharmacia Biotech; nitrocellulose extra blotting membranes: Sartorius A G, Goettingen, Germany). A standard high molecular weight solution was loaded as a reference. For visualization of molecular weight bands, the membrane was immersed in Ponceau reagent (0.05% Ponceau, 5% acetic acid) for a few minutes, and then washed twice with TTN (10 mM Tris pH 7.4, 0.2% TWEEN 20, 170 mM NaCl) and once with water. The membrane was blocked overnight in TTN containing 5% milk (1% fat) (blocking TTN) and incubated for 90 minutes with PY20 antiphosphotyrosine antibody (Santa Cruz Biotechnology Inc., Santa Cruz, USA) diluted 1:2,000 in blocking TTN. The membrane was then washed with TTN (3×5 minutes), incubated for 90 minutes with a horseradish peroxidase-conjugated secondary antibody (Goat anti-mouse IgG H+L, Jackson ImResearch Laboratories, Inc, diluted 1:10,000 in blocking TTN), and finally washed again with TTN (3×5 minutes). The membrane was incubated in a luminol-based solution (1 minute, 0.1 M Tris pH 8.5, 250 µM luminol, 400 µM p-cumaric acid, 0.033% $H_2O_2$) and visualized using chemiluminescent detection.

Quantification of the EGFR-P (protein) bands density obtained was performed using Adobe Photoshop 5.0ME and NIH image 1.16/ppc programs.

Specific Binding Measurements in Intact A431 Cells:

A431 cells were pre-incubated with 2 ml of DMEM containing 10% FCS for 40 minutes at room temperature under shaking conditions. One set of cells were then incubated with a non-labeled inhibitor (Compound 3 or 4), in order to determine the non-specific binding, while another set of cells were incubated with a vehicle only. A radiolabeled labeled inhibitor (carbon-11 labeled Compound 3 or 4) was then be added to both sets of cells. After incubation, cells were harvested with a cell harvester (Brandel Harvrester, model N48BI, Brandel, Gaithersburg, Md., USA) and were counted in a gamma-counter (1480 Wizard™ 3"). The specific binding of the radiolabeled inhibitor was calculated by subtracting the radioactivity level of cells pre-incubated with the non-labeled inhibitor from the radioactivity level of cells pre-incubated with the vehicle only.

In Vivo Studies:

WAG rnu/rnu male rats (300–400 grams) were injected s.c. in the left or right hind limb, or in the neck, with A431 cells (1×10⁷ in 200 µl sterile PBS). Tumor growth was monitored every 2–3 days by calipers. One to two weeks after inoculation, the rats were ready to be used in the following in-vivo biodistribution, metabolic and PET studies. Tumor mass ranging between 2 and 3 grams were used in these experiments.

Biodistribution: The biodistribution of carbon-11 labeled Compounds 3 and 4 in tumor-bearing rats was evaluated as follows; Tumor bearing rats were anesthetized with pentothal (intraperitoneal injection of 85 mg/Kg), and were injected in the jugular or tail vein with carbon-11 labeled Compound 3 or 4 in saline/EtOH. Animals were sacrificed at specific time points (between 0 and 1 hour) by means of $CO_2$ asphyxiation. Blood and certain organs and tissues including tumors were collected or excised, counted in a gamma-counter and weighed. % ID/organ, % ID/gram of tissue and tissue/blood uptake ratios were calculated.

Biological Stability: The metabolism of Compounds 3 and 4 has been also studied in the blood, liver and, tumor homogenates as follows: In general, control rats were injected with the radiolabeled compounds and sacrificed at several time points. One ml of blood was then collected, and about 2 grams of liver and tumor were minced and homogenized with 4 ml of physiological solution in a tissue grinder (Fenbroek). Ether was then added and the samples were counted in a gamma-counter. Blood, homogenized liver and tumor samples were extracted and the extracted fractions were measured for activity in a gamma-counter, spotted onto TLC, and the radioactivity was detected with phosphor imaging plates.

Positron Emission Tomography studies: Preliminary dynamic PET scans were performed on a Positron Corporation HZL/R scanner (intrinsic spatial resolution: in-plane 5.8 mm, axial 6.3 mm). Rats were anaesthetized with pentothal (85 mg/Kg) and placed supine on a flat polystyrene foam support with feet taped to the support, so as to minimize movements. Each rat was injected via the jugular vein with 250 µCi of carbon-11 labeled Compound 4 and were immediately thereafter subjected to dynamic emission scans, for 60 minutes. The PET data were normalized for variations in detector sensitivity, and corrected for wobble, randoms, scatter and deadtime. Attenuation correction was applied using the measured transmission scan data. PET images of the Posicam system (Positron Corporation) were reconstructed by filtered back-projection using a Butterworth filter (cut-off 0.2 cycles/mm, order 10). In order to evaluate the specific binding of the inhibitor to the tumor, comparative experiments in which non-labeled Compound 4 was administered to the rats 10 minutes prior to injecting the carbon labeled compound were conducted. These experiments were conducted with the same rats, two days after the first set of experiments.

Experimental Results

Chemical and Radio Syntheses:

In a quest for radiolabeled irreversible EGFR-TK inhibitors for use in radioimaging and radiotherapy, derivatives of [4-(phenylamino)quinazoline-6-yl]acrylamide (such as Compound 3, substituted Compound 3, Compound 4 and Compound 5) were prepared as exemplary compounds for other radiolabeled [4-(phenylamino)quinazolines substituted by α,β-unsaturated carboxylic derivatives. This class of compounds is prepared by reacting an aniline derivative with 4-chloroquinazoline substituted by a reactive group, and reacting the reactive obtained product with a reactive α,β-unsaturated carboxylic derivative to produce the final compound.

N-{4-[(3,4-dichloro-6-fluorophenyl)amino]quinazoline-6-yl}acrylamide (Compound 3) was prepared by reacting the corresponding aniline derivative with 4-chloro-6-nitro-quinazoline to produce compound 1 (Scheme 4), reducing the nitro group of compound 1 to the amino group, using an ethanolic solution of hydrazine hydrate and Raney®Nickel as described, to produce compound 2 and reacting compound 2 with acryloyl chloride, at 0° C., to produce the final product Compound 3 (Scheme 4).

Scheme 4

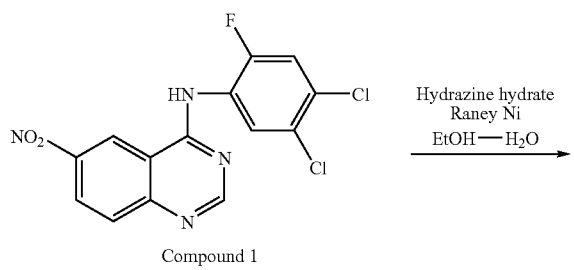

Compound 1

-continued

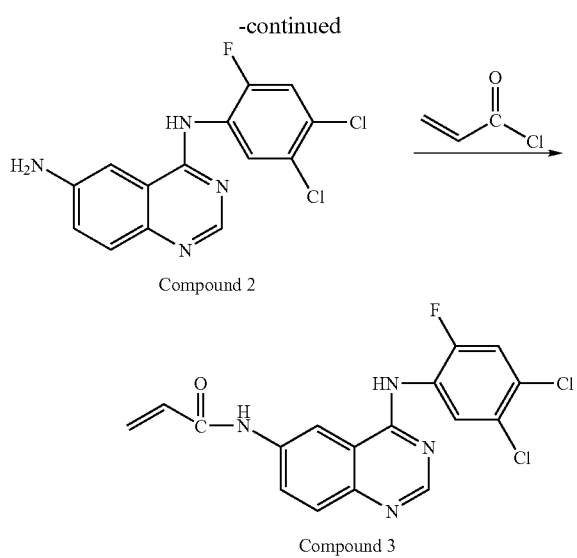

Compound 2

Compound 3

A radiolabeled Compound 3 was obtained by two optional labeling strategies. The first strategy involves the use of fluorine-18 in order to label the aniline moiety at position 6 thereof, using known procedures [17], while the second involves the use of carbon-11 labeled acryloyl synthon [18] at the final synthesis step.

Thus, fluorine-18 labeled Compound 3 was obtained by reacting 1,2-dichloro-4,5-nitrobenzene with potassium fluoride and Kryptofix®2.2.2 as phase transfer catalyst in DMSO solution. The fluorine-18 labeled product was then reduced in ethanolic solution of hydrazine hydrate and Raney®Nickel to produce the fluorine-18 labeled 3,4-dichloro-6-fluoroaniline (labeled compound 1, Scheme 5). The final fluorine-18 labeled product was obtained by using the steps described hereinabove (Scheme 4).

Scheme 5

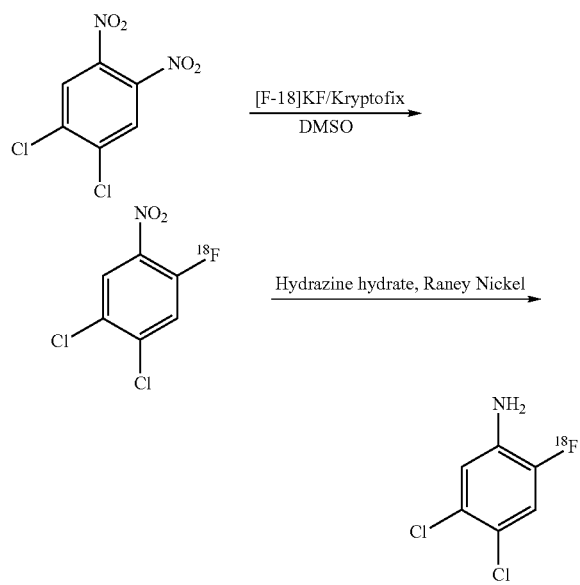

The carbon-11 labeled Compound 3 was obtained by using a carbon-11 labeled acryloyl chloride in the final step of the synthesis. The carbon-11 labeled acryloyl chloride was produced by reacting carbon-11 carbon-11 labeled $CO_2$ with vinyl magnesium bromide, phtaloyl chloride and ditertbutylpyridine, and was reacted thereafter with compound 2 to yield the final carbon-11 labeled product. This radiosynthesis was carried out by a fully automated route using the Nuclear Interface MeI module.

Using modifications of the procedures described hereinabove, other radiolabeled compounds, such as a bromine-labeled and iodine-labeled Compound 3 and a morpholino-substituted Compound 3 radiolabeled by carbon-11, fluorine-18, radioactive bromine and radioactive iodine can be prepared.

As is discussed hereinabove, in a quest for radiolabeled irreversible EGFR-TK inhibitors with improved biological half-life, radiolabeled derivatives of Compound 4 have also been prepared.

Thus, carbon-11 labeled Compound 4 was successfully obtained by an automated radiosynthesis method, depicted in Scheme 6 below so as to obtain 15% decay-corrected radiochemical yield, 100% radiochemical purity, 93% chemical purity, and specific activity of 1.8 Ci/μmol at end of bombardment (EOB).

Scheme 6

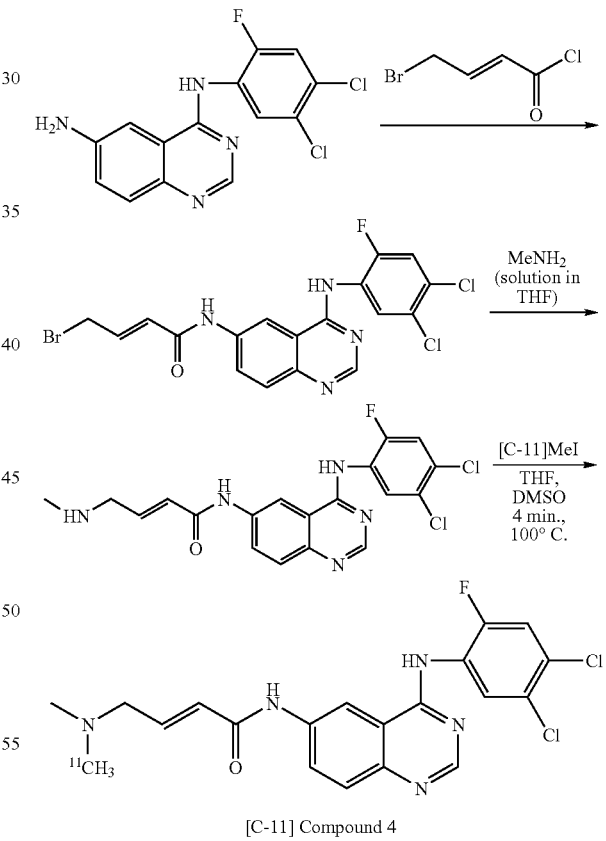

[C-11] Compound 4

Similarly, based on the fluorine-18 radiosynthesis described hereinabove, the fluorine-18 labeled Compound 4 can be prepared.

As iodine-124 has recently become increasingly significant in PET diagnostic use and a potential therapeutic radionuclides, due to its radiocharacterisitics (T1/2=4.2 days, simultaneous positron emission and electron capture), preparation of an, iodine-124 labeled irreversible EGFR inhibitor is highly desirable. Hence, based on established radioiodination chemistry, iodine-124 labeled Compound 5 was prepared, as is depicted in Scheme 7 below.

In order to demonstrate the irreversibility of the binding of Compound 3 to the receptor, the cells were incubated with variable inhibitor concentrations for two hours. After the incubation, the media was replaced with inhibitor/FCS-free

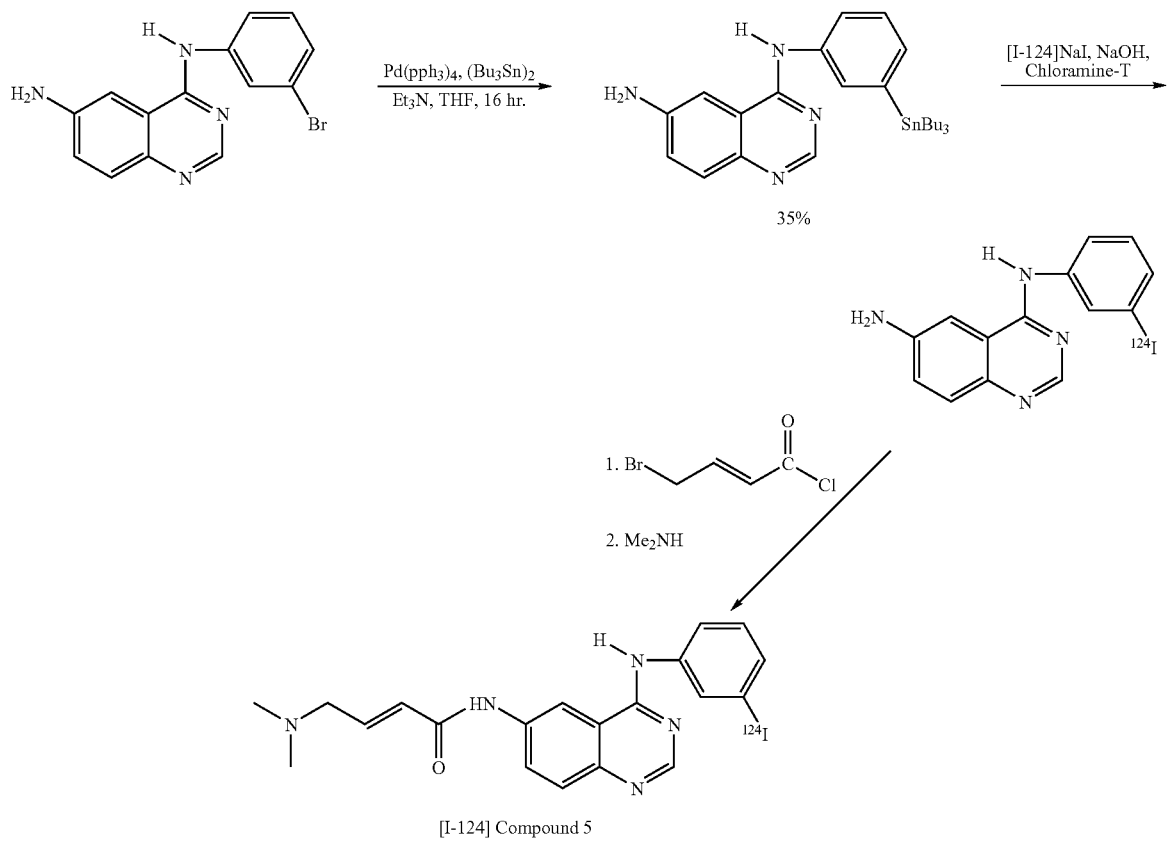

Bromine-labeled Compound 6 and other iodine labeled compounds can be similarly prepared, as is detailed hereinabove.

In Vitro Studies.

EGFR-TK autophosphorylation $IC_{50}$ values were measured for Compounds 3 and 4 in order to determine their potential as PET tracers. The method employed an ELISA assay based on an anti-EGFR antibody. Since the measured compounds have an irreversible inhibition kinetic, the $IC_{50}$ values thereof are apparent values which were calculated using a non-linear regression fit to a variable slope sigmoidal dose response curve. The ELISA assay was performed twice and the apparent $IC_{50}$ averages were obtained from 4 independent dose-response curves (n=4, $IC_{50app}$=0.042 nM±0.016). A plot of an exemplary dose-response curve of Compound 3 with an $IC_{50app}$ value of 0.051 nM and a range of 0.0088/0.294 as 95% confidence intervals is shown in FIG. 1 where $r^2$ equals 0.995. A plot of an exemplary dose-response curve of Compound 4 with an $IC_{50app}$ value of 0.06 nM and $r^2$ that equals 0.995 is shown in FIG. 5.

The irreversible nature of Compounds 3 and 4 EGFR-TK binding and the kinetic parameters thereof were evaluated by measuring the inhibition of EGFR-TK autophosphorylation in intact A431 cell line.

media and the inhibition effect was measured and compared after 2 and 8 hours. As is presented in FIG. 2, after 2 hours in an inhibitor/FCS-free media about 35%, 40% and about 100% inhibition was obtained at 0.5 nM, 5 nM and 50 nM inhibitor concentrations, respectively. Furthermore, it is shown that even after 8 hours post-incubation the inhibition was still evident for a 50 nM inhibitor concentration (about 97%). This high autophosphorylation inhibition obtained at this concentration after both 2 hours and 8 hours post-incubation periods is attributed to the high ratio of pmoles inhibitor/pmoles EGFR at this concentration. However, a small quantity of phosphorylation is observed at 50 nM after 8 hours, which can be explained by a proliferation of cells and a new biosynthesis/expression on the cell surface of new receptors.

FIGS. 3 and 4 present the decrease of EGFR autophosphorylation following varying incubation times of intact A431 cells with Compound 3 and varying inhibitor concentrations, respectively. The EGFR autophosphorylation level was measured at 1 hour and 8 hours post-incubation periods.

As is shown in FIG. 3, 10 minutes incubation time and 30 nM inhibitor concentration were needed to obtain 80% inhibition after 8 hours post-incubation period. The same effect is shown in FIG. 4 for 9 minutes incubation time and 30 nM inhibitor concentration. These results reflect the nature of the irreversible binding of the inhibitor, which maintains about the same inhibition potency at both 1 hour and 8 hours post-incubation periods.

FIG. 4 further supports the observed results by presenting this high inhibition effect only at high inhibitor concentrations.

Similar tests were performed with Compound 4, at a concentration of 20 nM. A 65% inhibition was observed 8 hours post-incubation, reflecting the irreversible binding of this inhibitor as well.

FIG. 6 presents the results obtained for the specific binding of carbon-11 labeled Compounds 4 to A431 cells. 78% specific binding of Compound 4 was obtained, indicating an increase of 10% as compared to the specific binding obtained with carbon-11 labeled Compound 3 (data not shown).

In vivo Studies:

FIG. 7 presents the results obtained in the biodistribution studies conducted with carbon-11 labeled Compound 4 in tumor (A431) bearing rats. As is shown in FIG. 7, the maximal injection dose percentages (% ID)/gram tumor/blood ratio, 2.6, was obtained two hours post injection. As is further shown in FIG. 7, a tumor uptake of 0.25% ID/gram and of 0.24% ID/gram was observed 15 minutes and 30 minutes post-adnainistration, respectively. These results indicate a significant improvement as compared with the tumor/blood ratios obtained with carbon-11 labeled Compound 3, which was 0.09% ID/gram and 0.05% ID/gram, 15 and 30 minutes post administration (data not shown). Moreover, while the tumor uptake of Compound 4 remained constant, the tumor uptake of Compound 3 decreased with time.

FIGS. 8a–b present the results obtained in the comparative metabolic studies conducted with carbon-11 labeled Compounds 3 and 4. As is shown in FIG. 8a, while metabolites of Compound 3 were detected in both the liver and blood 30 minutes post injection, no metabolites of Compound 4 were detected even at 60 minutes post injection. As is shown in FIG. 8b, 60% of Compound 4 remained intact in blood 15 minutes post injection, with no substantial reduction with time, whereas only 20% of compound 3 remained intact in blood 15 minutes post injection and no tracer was remained 45 minutes post injection. These results reflect the successful chemical structure optimization of the inhibitors of the present invention, which led to increases biological stability of Compound 4, as compared with Compound 3.

The results obtained in preliminary PET studies are presented in FIGS. 9–12.

FIG. 9 shows the sum of the non-attenuated corrected frames obtained in nude tumor bearing rats injected with carbon-11 labeled Compound 4, between 10 to 40 minutes post injection (A), and clearly demonstrate the uptake of the radiolabeled Compound 4 could be observed. Moreover, the tumor was visualized throughout a 1-hour scan. As is further shown in FIG. 9, when the same rats were pre-injected with non-labeled compound 4 (B), in an experiment conducted 2 days after that presented in A, the tumor uptake of the radiolabeled Compound 4 was blocked, reflecting again the specific, irreversible tumor binding of Compound 4.

FIG. 10 presents time activity curves generated for the tumor region in both sets of experiments. As can be seen in FIG. 10, the value of the total activity uptake of the radiolabeled Compound 4 in tumor, when administered alone was doubled as compared with its uptake after pre-injecting a non-labeled compound, a 50% specific binding of then radiolabeled inhibitor in tumor).

FIG. 11 present time activity curves of carbon-11 labeled Compound 4 in the liver and kidney of the rats. The obtained uptake values might reflect the high blood perfusion of these organs in relation to the tumor and the accumulation of radioactivity which is metabolized in these organs. However, as can be seen in FIG. 11, while activity uptake in the tumor remained constant during the first one hour scan, liver activity uptake decreased by 25% during the same one hour scanning time, suggesting that labeling with a longer lived isotope, other than carbon-11 (e.g., fluorine-18 and iodine-124) may result in better results.

The preliminary in-vitro and in-vivo studies described hereinabove demonstrate the high stability, affinity and specific tumor binding of the irreversible inhibitors of the present invention, Compound 4 in particular, which provides for successful imaging. These compounds can therefore be considered promising candidates for optimal labeling, resulting into the best imaging characteristics. As such, the radiolabeled compounds of the present invention can be efficiently used in, for example, imaging of various tumor organs.

As is known in the art, EGFR is overexpressed prostate cancer. To date, imaging tools (including PET) for diagnosing recurrence and metastatic sites of prostatic cancer are suboptimal due to excretion of the radiopharmaceuticals in the bladder, which result in masking of the prostatic bed. In order to evaluate the efficacy of the radiolabeled compounds of the present invention in radioimaging of prostate cancer, the excretion of carbon-11 labeled Compound 4 was measured and compared with that of PDG. The obtained results arc presented in FIG. 12 and clearly demonstrate that while FDG is excreted in the bladder in great quantities, carbon-11 labeled Compound 4 had a slower and minimal bladder excretion.

Thus, a method was developed for the synthesis of radiolabeled irreversible EGFR-TK ATP-site inhibitors. A member of these inhibitors family (Compound 3) was found to be highly potent irreversible EGFR-TK inhibitor and highly potent biological tracer and was successfully radiolabeled with both carbon-11 and fluorine-18 in yields and reaction times suitable for its use as a biological tracer. Another member of this family (Compound 4), which was structurally optimized, was found to be even higher potent irreversible EGFR-TK inhibitor and higher potent biological tracer, exerting superb biological stability and tumor binding specifity. Therefore, this class of radioactive labeled compounds can be used to measure differences in EGFR-TK expression and ATP binding site fractional occupancy in vitro and in vivo and can be used as efficient PET tracers in, for example, cancer diagnosis, staging and therapy protocol selection, e.g., in predicting which patients would benefit from EGF-directed therapeutic approaches such as those based on anti-EGF antibodies, EGF-directed fusion toxins, or EGFR-TK inhibitors. Another member of these inhibitors family, which is radiolabeled with either a radioactive bromine or a radioactive iodine can be used for radioimaging and radiotherapy with respect to EGFR-TK expression. Thus, bromine-76 labeled and iodine-124 labeled compounds can be used for PET radioimaging and iodine-123 labeled compounds can be used for SPECT radioimaging, while bromine-77 labeled, iodine-124 and iodine-131 labeled compounds can be used for radiotherapy.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES CITED BY NUMERALS

1. Escobar, N. I.; Morales, A. M.; Ducongu, J.; Torres, I. C.; Fernandez, E.; Gomez, J. A. Pharmacokinetics, biodistribution and dosimetry of 99mTc-labeled anti-human epidermal growth factor receptor humanized monoclonal antibody R3 in rats. *Nucl. Med. Biol*. 1998, 25, 17–23.
2. Iznaga-Escobar, N.; Torres, L. A.; Morales, A.; Ramos, M.; Alvarez, I.; Perez, N.; Fraxedas, R.; Rodriguez, O.; Rodriguez, N.; Perez, R.; Lage, A; Stabin, M. G. *J. Nucl. Med*. 1998, 39, 15–23.
3. Capala, J.; Barth, R. F.; Bailey, M. Q.; Fenstermaker, R. A.; Marek, M. J.; Rhodes, B. A. Radiolabeling of epidermal growth factor with Tc and in vivo localization following intracerebral injection into normal and glioma-bearing rats. *Bioconjug. Chem*. 1997, 8, 289–295.
4. Holmberg, A.; Marquez, M.; Westlin, J.-E.; Nilsson, S. Labeling of polypeptides with technetium-99m using a dextran spacer. *Cancer Res*. 1995, 55, 5710s–5713s.
5. Remy, S.; Reilly, R. M.; Sheldon, K.; Gariepy, J. A new radioligand for the epidermal growth factor receptor: In labeled human epidermal growth factor derivatized with a bifunctional metal-chelating peptide. *Bioconjugate Chem*. 1995, 6, 683–690.
6. Reilly, R. M.; Gariepy, J. Investigation of factors influencing the sensitivity of tumor imaging with phantoms and a receptor binding radiopharmaceutical. *J. Nucl. Med*. 1996, 37 (supplement), 199P (abstract number 911).
7. Scott-Robson, S.; Capala, J.; Malmborg, P.; Lundqvist, H. Production of Br and its use in labeling proteins. *Acta Radiol. Suppl*. 1991, 376, 64.
8. Scott-Robson, S.; Capala, J.; Carlsson, J.; Malmborg, P.; Lundqvist, H. Distribution and stability in the rat of a Br/I-labeled polypeptide, epidermal growth factor. *Int. J. Appl. Instrum.[B]* 1991, 18, 241–246.
9. Fry, D. W.; Kraker, A. J.; McMichael, A.; Ambroso, L. A.; Nelson, J. M.; Leopold, W. R.; Connors, R. W.; Bridges, A. J. A specific inhibitor of the epidermal growth factor receptor tyrosine kinase. *Science* 1994, 265, 1093–1095.
10. Levitzki, A.; Gazit, A. *Science* 1995 267, 1782–1788.
11. Mulholland, G. K.; Winkle, W.; Mock, B. H.; Sledge, G. *J. Nucl. Med*. 1995, 36 (supplement), 71P.
12. Johnstrom P., Fredriksson A., Thorell J.-O., and Stone-Elander S.—*J. Labelled Cpd. Radiopharm*. 41: 623 (1998).
13. Mulholland, G. K.; Zheng, Q.-H.; Winkle, W. L.; Carlson, K. A. *J. Nucl. Med*. 1997, 38, 141P (abstract number 529).
14. Eckelman, W. C. The application of receptor theory to receptor-binding and enzyme-binding oncologic radiopharmaceuticals. *Nucl. Med. Biol*. 1994, 21, 759–769.
15. Smaill J. B.; ReG. W.; Loo J. A.; Greis K. D.; Chan O. H.; Reyner E. L.; Lipka E.; Showalter H. D.; Vincent P. W.; Elliott W. L.; Denny W. A. *J Med Chem*. 43, 1380–1397 (2000).
16. Smaill J. B. et al. *J Med Chem*, 42, 1803–1815 (1999).
17. Mishani E., Cristel M. E., Dence C. S., McCarthy T. J., and Welch M. J. *Nucl. Med. Biol*. 24: 269 (1997).
18. Lasne M. C.; Cairon P.; Barre L. *Appl. Radiat. Isot*., 43, 621–625, (1992).
19. Tsou H.-R. et al. *J. Med. Chem*. 44, 2719–2734 (2001).
20. Mishani E., Ben-david I., Rozen Y., Laki d., Bocher M. and Chisin R., *J. Labl. Comp. Radiopharm*. 44, 379, 2001.

What is claimed is:
1. A radiolabeled compound of a formula:

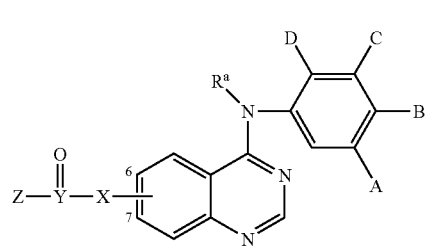

Formula II wherein:
Q1 is X—Y(=O)-Z and Q2 is selected from the group consisting of hydrogen, halogen, alkoxy, hydroxy, thiohydroxy, thioalkoxy, alkylamino and amino, or
Q1 is selected from the group consisting of hydrogen, halogen, alkoxy, hydroxy, thiohydroxy, thioalkoxy, alkylamino and amino and Q2 is X—Y(=O)-Z;
X is selected from the group consisting of —NR$^1$—, —O—, —NH—NR$^1$—, —O—NR$^1$—, NH—CHR$^1$—, —CHR$^1$—NH—, —CHR$^1$—O—, —O—CHR$^1$—, —CHR$^1$—CH$_2$— and —CHR$^1$—S— or absent;
Y is selected from the group consisting of a non-radioactive carbon and a radioactive carbon;
Z is selected from the group consisting of —R$^2$C=CHR$^3$, —C≡C—R$^3$ and —R$^2$C=C=CHR$^3$;
R$^a$ is selected from the group consisting of hydrogen or alkyl having 1–8 carbon atoms;
A, B, C and D are each independently selected from the group consisting of hydrogen, a non-radioactive derivatizing group, and a radioactive derivatizing group, whereas said non-radioactive group is selected from the group consisting of halogen, alkyl, haloalkyl, hydroxy, alkoxy, carboxy, carbalkoxy, thiocarboxy, thiohydroxy, thioalkoxy, alkylsulfinyl, alkylsulfonyl, amino, diamino, carbamyl, dicarbamoyl, nitro and cyano, and said radioactive derivatizing group is selected from a radioactive bromine, a radioactive iodine and a radioactive fluorine;
R$^1$ is selected from the group consisting of hydrogen, and substituted or non-substituted alkyl having 1–6 carbon atoms;
R$^2$ is selected from the group consisting of hydrogen, halogen and alkyl having 1–6 carbon atoms; and
R$^3$ is a substituted alkyl having 1–6 carbon atoms, which comprises a substituted amino group;

provided that the compound comprises at least one radioactive atom.

2. The radiolabeled compound of claim 1, wherein said substituted alkyl comprises a radioactive atom.

3. The radiolabeled compound of claim 1, wherein said substituted amino group is selected from the group consisting of an alkylamino group and a dialkylamino group.

4. The radiolabeled compound of claim 3, wherein said substituted amino group comprises said radioactive atom.

5. The radiolabeled compound of claim 4, wherein said radioactive atom is a radioactive carbon.

6. The radiolabeled compound of claim 5, wherein said radioactive carbon is carbon-11.

7. The radiolabeled compound of claim 1, wherein said alkoxy comprises a morpholino group.

8. The radio labeled compound of claim 1, wherein said alkylamino comprises a N-piperazinyl group.

9. The radiolabeled compound of claim 1, wherein Q1 is X—Y(=O)-Z and Q2 is selected from the group consisting of hydrogen, halogen, alkoxy, hydroxy, thiohydroxy, thioalkoxy, alkylamino and amino.

10. The radiolabeled compound of claim 1, wherein Q1 is X—Y(=O)-Z and Q2 is hydrogen.

11. The radiolabeled compound of claim 1, wherein Q1 is X—Y(=O)-Z and Q2 is alkoxy.

12. The radiolabeled compound of claim 11, wherein alkoxy comprises a morpholino group.

13. The radiolabeled compound of claim 1, wherein Q1 is X—Y(=O)-Z and Q2 is alkylamino.

14. The radiolabeled compound of claim 13, wherein said alkylamino comprises a N-piperazinyl group.

15. The radiolabeled compound of claim 10, wherein X is said —NR$^1$— and Z is said —R$^2$C=CHR$^3$.

16. The radiolabeled compound of claim 15, wherein each of R$^1$ and R$^2$ is hydrogen.

17. The radio labeled compound of claim 16, wherein said substituted alkyl comprises a radioactive atom.

18. The radiolabeled compound of claim 16, wherein said substituted amino group is selected from the group consisting of an alkylamino group and a dialkylamino group.

19. The radiolabeled compound of claim 18, wherein said substituted amino group comprises a radioactive atom.

20. The radiolabeled compound of claim 19, wherein said radioactive atom is a radioactive carbon.

21. The radiolabeled compound of claim 20, wherein said radioactive carbon is carbon-11.

22. The radiolabeled compound of claim 1, wherein Y is said radioactive carbon.

23. The radiolabeled compound of claim 1, wherein at least one of A, B, C and D is said radioactive fluorine.

24. The radiolabeled compound of claim 1, wherein D is said radioactive fluorine.

25. The radiolabeled compound of claim 24, wherein A and B are each chlorine and C is hydrogen.

26. The radiolabeled compound of claim 1, wherein A is said radioactive bromine.

27. The radiolabeled compound of claim 1, wherein A is said radioactive iodine.

28. The radiolabeled compound of claim 1, wherein said radioactive carbon is carbon-11.

29. The radiolabeled compound of claim 28, wherein A and B are each chlorine, C is hydrogen and D is fluorine.

30. The radiolabeled compound of claim 28, wherein A is bromine or iodine and B, C and D are each hydrogen.

31. The radiolabeled compound of claim 6, wherein A and B are each chlorine, C is hydrogen and D is fluorine.

32. The radiolabeled compound of claim 6, wherein A is bromine or iodine and B, C and D are each hydrogen.

33. The radiolabeled compound of claim 21, wherein A and B are each chlorine, C is hydrogen and D is fluorine.

34. The radiolabeled compound of claim 21, wherein A is bromine or iodine and B, C and D are each hydrogen.

35. The radiolabeled compound of claim 1, wherein said radioactive fluorine is fluorine-18.

36. The radiolabeled compound of claim 1, wherein said radioactive bromine is bromine-76 or bromine-77.

37. The radiolabeled compound of claim 1, wherein said radioactive iodine is iodine-123, iodine-124 or iodine-131.

38. The radiolabeled compound of claim 37, wherein said radioactive iodine is iodine-124.

39. The radiolabeled compound of claim 12, wherein Y is said radioactive carbon.

40. The radiolabeled compound of claim 39, wherein said radioactive carbon is carbon-11.

41. The radiolabeled compound of claim 40, wherein A and B are each chlorine, C is hydrogen and D is fluorine.

42. The radiolabeled compound of claim 40, wherein A is bromine or iodine and B, C and D are each hydrogen.

43. The radiolabeled compound of claim 12, wherein at least one of A, B, C and D is a radioactive atom selected from the group consisting of a radioactive fluorine, a radioactive bromine and a radioactive iodine.

44. A pharmaceutical composition comprising as an active ingredient the radiolabeled compound of claim 1 and a pharmaceutical acceptable carrier.

45. A method of monitoring the level of epidermal growth factor receptor within a body of a patient, the method comprising:

(a) administering to the patient the radiolabeled compound of claim 1; and (b) employing a nuclear imaging technique selected from the group consisting of positron emission tomography (PET) and single photon emission computed tomography (SPECT) for monitoring a distribution of the compound within the body or within a portion thereof.

46. A method of radiotherapy comprising administering to a patient a therapeutically effective amount of the radiolabeled compound of claim 1.

47. A method of synthesizing a radiolabeled compound of a formula:

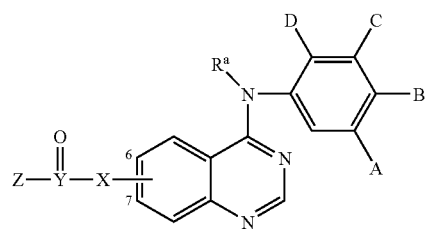

Formula II wherein:

X—Y(=O)-Z is at position 6 or 7 of the quinazoline ring;

X is selected from the group consisting of —NR$^1$—, —O—, —NH—NR$^1$—, —O—NR$^1$—, NH—CHR$^1$—, —CHR$^1$—NH—, —CHR$^1$—O—, —O—CHR$^1$—, —CHR$^1$—CH$_2$— and —CHR$^1$—S— or absent;

Y is carbon-11;

Z is selected from the group consisting of —R²C═CHR³, —C≡C—R³ and —R²C═C═CHR³;

Rᵃ is selected from the group consisting of hydrogen or alkyl having 1–8 carbon atoms;

A, B, C and D are each independently hydrogen or a non-radioactive derivatizing group selected from the group consisting of hydrogen, halogen, alkyl, haloalkyl, hydroxy, alkoxy, carboxy, carbalkoxy, thiocarboxy, thiohydroxy, thioalkoxy, alkylsulfinyl, alkylsulfonyl, amino, diamino, carbamyl, dicarbamoyl, nitro and cyano;

R¹ is selected from the group consisting of hydrogen and substituted or non-substituted alkyl having 1–6 carbon atoms;

R² is selected from the group consisting of hydrogen, halogen and alkyl having 1–6 carbon atoms; and R³ is a substituted alkyl having 1–6 carbon atoms, which comprises a substituted amino group, the method comprising:

(a) coupling an aniline derivatized by said Rᵃ, A, B, C and D with a 4-chloroquinazoline substituted at position 6 and/or 7 by at least one reactive group, so as to produce a reactive 4-(phenylamino)quinazoline derivatized by said A, B, C and D;

(b) reacting said reactive 4-(phenylamino)quinazoline with a reactive carbon-11 labeled α,β-unsaturated carboxylic derivative, said reactive α,β-unsaturated carboxylic derivative terminating with a second reactive group, so as to produce a carbon-11 labeled 4-(phenylamino)quinazoline substituted by said α,β-unsaturated carboxylic group terminating with said second reactive group; and (c) reacting said carbon-11 labeled 4-(phenylamino) quinazoline substituted by said α,β-unsaturated carboxylic group terminating with said second reactive group, with a reactive substituted alkyl having 1–6 carbon atoms.

48. The method of claim 47, wherein said X—Y(═O)-Z is at position 6 of the quinazoline ring.

49. The method of claim 47, wherein said reactive 4-(phenylamino)quinazoline is 4-(phenylamino)-6-nitroquinazoline, the method further comprising, prior to step (b):

(c) reducing said 4-(phenylamino)-6-nitroquinazoline so as to produce a 4-(phenylamino)-6-aminoquinazoline derivatized by said A, B, C and D.

50. The method of claim 47, wherein said 4-chloroquinazoline is substituted at positions 6 and 7 by a first and a third reactive groups, the method further comprising, prior to step (b):

(d) reacting said reactive 4-(phenylamino)quinazoline with a chemically reactive group.

51. The method of claim 50, wherein said chemically reactive group comprises a morpholinoalkoxy group.

52. The method of claim 47, wherein said reactive carbon-11 labeled α,β-unsaturated carboxylic derivative is carbon-11 labeled 4-bromocrotonyl chloride.

53. A method of synthesizing a radiolabeled compound of a formula:

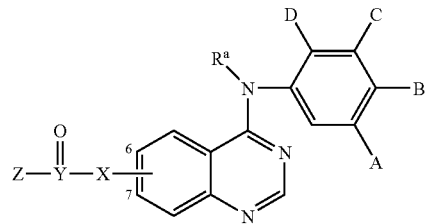

Formula II wherein:

X—Y(═O)-Z is at position 6 or 7 of the quinazoline ring;

X is selected from the group consisting of —NR¹—, —O—, —NH—NR¹—, —O—NR¹—, NH—CHR¹—, —CHR¹—NH—, —CHR¹—O—, —O—CHR¹—, —CHR¹—CH₂— and —CHR¹—S— or absent;

Y is a non-radioactive carbon;

Z is selected from the group consisting of —R²C═CHR³, —C≡C—R³ and —R²C═C═CHR³;

Rᵃ is selected from the group consisting of hydrogen or alkyl having 1–8 carbon atoms;

A, B, C and D are each independently selected from the group consisting of hydrogen, a non-radioactive derivatizing group and a fluorine-18, whereas said non-radioactive derivatizing group is selected from the group consisting of hydrogen, halogen, alkyl, haloalkyl, hydroxy, alkoxy, carboxy, carbalkoxy, thiocarboxy, thiohydroxy, thioalkoxy, alkylsulfinyl, alkylsulfonyl, amino, diamino, carbamyl, dicarbamoyl, nitro and cyano, provided that at least one of A, B, C and D is said fluorine-18;

R¹ is selected from the group consisting of hydrogen, and substituted or non-substituted alkyl having 1–6 carbon atoms;

R² is selected from the group consisting of hydrogen, halogen and alkyl having 1–6 carbon atoms; and R³ is a substituted alkyl having 1–6 carbon atoms, which comprises a substituted amino group, the method comprising:

(a) preparing a fluorine-18 labeled aniline derivatized by said Rᵃ, A, B, C and D, wherein at least one of A, B, C and D is said fluorine-18;

(b) coupling said fluorine-18 labeled aniline derivatized by said Rᵃ, A, B, C and D with 4-chloroquinazoline substituted at position 6 and/or 7 by at least one reactive group, so as to produce a reactive fluorine-18 labeled 4-(phenylamino)quinazoline derivatized by said A, B, C and D;

(c) reacting said reactive fluorine-18 labeled 4-(phenylamino)quinazoline with a reactive α,β-unsaturated carboxylic derivative, said reactive α,β-unsaturated carboxylic derivative terminating with a second reactive group, so as to produce a fluorine-18 labeled 4-(phenylamino)quinazoline substituted by an α,β-unsaturated carboxylic group terminating with said second reactive group; and (d) reacting said a fluorine-18 labeled 4-(phenylamino) quinazoline substituted at position 6 or 7 by an α,β-unsaturated carboxylic group terminating with said reactive group with a reactive substituted alkyl having 1–6 carbon atoms.

54. The method of claim 53, wherein said X—Y(=O)-Z is at position 6 of the quinazoline ring.

55. The method of claim 53, wherein said reactive fluorine-18 labeled 4-(phenylamino)quinazoline is fluorine-18 labeled 4-(phenylamino)-6-nitroquinazoline, the method further comprising, prior to step (c):
(d) reducing said fluorine-18 labeled 4-(phenylamino)-6-nitroquinazoline, so as to produce a fluorine-18 labeled 4-(phenylamino)-6-aminoquinazoline derivatized by said A, B, C and D.

56. The method of claim 53, wherein said 4-chloroquinazoline is substituted at positions 6 and 7 by a first and a third reactive groups, the method further comprising, prior to step (c):
(e) reacting said reactive fluorine-18 labeled 4-(phenylamino)quinazoline with a chemically reactive group.

57. The method of claim 56, wherein said chemically reactive group comprises a morpholinoalkoxy group.

58. The method of claim 53, wherein said reactive α,β-unsaturated carboxylic derivative terminating with said second reactive group is 4-bromocrotonyl chloride.

59. The method of claim 53, wherein said reactive substituted alkyl is dimethylamine.

60. A method of synthesizing a radiolabeled compound of a formula:

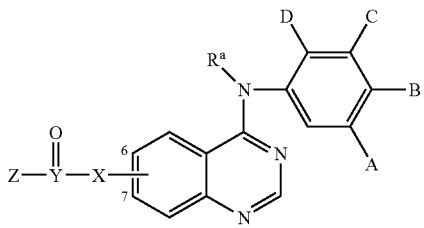

Formula II wherein:
X—Y(=O)-Z is at position 6 or 7 of the quinazoline ring;
X is selected from the group consisting of —NR$^1$—, —O—, —NH—NR$^1$—, —O—NR$^1$—, NH—CHR$^1$—, —CHR$^1$—NH—, —CHR$^1$—O—, —O—CHR$^1$—, —CHR$^1$—CH$_2$— and —CHR$^1$—S— or absent;
Y is a non-radioactive carbon;
Z is selected from the group consisting of —R$^2$C=CHR$^3$, —C≡C—R$^3$ and —R$^2$C=C=CHR$^3$;
R$^a$ is selected from the group consisting of hydrogen or alkyl having 1–8 carbon atoms;
A, B, C and D are each independently selected from the group consisting of hydrogen, a non-radioactive derivatizing group and a radioactive atom, whereas said non-radioactive group is selected from the group consisting of halogen, alkyl, haloalkyl, hydroxy, alkoxy, carboxy, carbalkoxy, thiocarboxy, thiohydroxy, thioalkoxy, alkylsulfinyl, alkylsulfonyl, amino, diamino, carbamyl, dicarbamoyl, nitro and cyano, and said radioactive derivatizing group is selected from a radioactive bromine and a radioactive iodine, provided that at least one of A, B, C and D is said radioactive bromine or said radioactive iodine;
R$^1$ is selected from the group consisting of hydrogen, and substituted or non-substituted alkyl having 1–6 carbon atoms;
R$^2$ is selected from the group consisting of hydrogen, halogen and alkyl having 1–6 carbon atoms; and
R$^3$ is a substituted alkyl having 1–6 carbon atoms, which comprises a substituted amino group, the method comprising:
(a) coupling an aniline derivatized by said R$^a$, A, B, C and D, wherein at least one of A, B, C and D is a halogen, with a 4-chloroquinazoline substituted at position 6 and/or 7 by at least one reactive group, so as to produce a reactive 4-(phenylamino)quinazoline derivatized by said A, B, C and D, wherein at least one of A, B, C and D is said halogen;
(b) radiolabeling said reactive 4-(phenylamino)quinazoline derivatized by said A, B, C and D with a radioactive bromine or a radioactive iodine, so as to produce a radioactive bromine labeled or a radioactive iodine labeled reactive 4-(phenylamino)quinazoline derivatized by said A, B, C and D, wherein at least one of said A, B, C and D is said radioactive bromine or said radioactive iodine;
(c) reacting said radioactive bromine labeled or radioactive iodine labeled reactive 4-(phenylamino)quinazoline with a reactive α,β-unsaturated carboxylic derivative, said reactive α,β-unsaturated carboxylic derivative terminating with a second reactive group, so as to produce a radioactive bromine labeled or radioactive iodine labeled 4-(phenylamino)quinazoline substituted at position 6 or 7 by an α,β-unsaturated carboxylic group terminating with said second reactive group; and
(d) reacting said radioactive bromine labeled or radioactive iodine labeled 4-(phenylamino)quinazoline substituted at position 6 or 7 by an α,β-unsaturated carboxylic group terminating with said second reactive group with a reactive substituted alkyl having 1–6 carbon atoms.

61. The method of claim 60, wherein said radioactive bromine is bromine-76 or bromine-77.

62. The method of claim 60, wherein said radioactive iodine is iodine-123, iodine-124 or iodine-131.

63. The method of claim 60, wherein said X—Y(=O)-Z is at position 6 of the quinazoline ring.

64. The method of claim 60, wherein said reactive 4-(phenylamino)quinazoline is 4-(phenylamino)-6-nitroquinazoline, the method further comprising, prior to step (b):
(d) reducing said 4-(phenylamino)-6-nitroquinazoline, so as to produce a 4-(phenylamino)-6-aminoquinazoline derivatized by said A, B, C and D, wherein at least one of said A, B, C and D is said halogen.

65. The method of claim 60, wherein said halogen is bromine.

66. The method of claim 60, wherein said 4-chloroquinazoline is substituted at positions 6 and 7 by a first and a third reactive groups, the method further comprising, prior to step (c):
(e) reacting said reactive radioactive bromine labeled or radioactive iodine labeled 4-(phenylamino)quinazoline with a chemically reactive group.

67. The method of claim 66, wherein said chemically reactive group comprises a morpholinoalkoxy group.

68. The method of claim 66, wherein said reactive α,β-unsaturated carboxylic derivative terminating with said second reactive group is 4-bromocrotonyl chloride.

69. The method of claim 60, wherein said reactive substituted alkyl is dimethylamine.

70. A method of synthesizing a radiolabeled compound of a formula:

Formula II

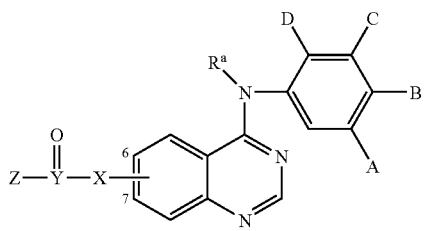

wherein:
X—Y(=O)-Z is at position 6 or 7 of the quinazoline ring;
X is selected from the group consisting of —NR¹—, —O—, —NH—NR¹—, —O—NR¹—, NH—CHR¹—, —CHR¹—NH—, —CHR¹—O—, —O—CHR¹—, —CHR¹—CH₂— and —CHR¹—S— or absent;
Y is a non-radioactive carbon;
Z is selected from the group consisting of —R²C=CHR³, —C≡C—R³ and —R²C=C=CHR³;
Rᵃ is selected from the group consisting of hydrogen or alkyl having 1–8 carbon atoms;
A, B, C and D are each independently hydrogen or a non-radioactive derivatizing group selected from the group consisting of hydrogen, halogen, alkyl, haloalkyl, hydroxy, alkoxy, carboxy, carbalkoxy, thiocarboxy, thiohydroxy, thioalkoxy, alkylsulfinyl, alkylsulfonyl, amino, diamino, carbamyl, dicarbamoyl, nitro and cyano;
R¹ is selected from the group consisting of hydrogen, and substituted or non-substituted alkyl having 1–6 carbon atoms;
R² is selected from the group consisting of hydrogen, halogen and alkyl having 1–6 carbon atoms; and
R³ is a substituted alkyl having 1–6 carbon atoms, which comprises a substituted amino group, said substituted alkyl further comprising a carbon-11 atom, the method comprising:
(a) coupling an aniline derivatized by said Rᵃ, A, B, C and D with a 4-chloroquinazoline substituted at position 6 or 7 by a first reactive group, so as to produce a reactive 4-(phenylamino)quinazoline derivatized by said A, B, C and D;
(b) reacting said reactive 4-(phenylamino)quinazoline with a reactive α,β-unsaturated carboxylic derivative, said reactive α,β-unsaturated carboxylic derivative terminating with a second reactive group, so as to produce a 4-(phenylamino)quinazoline substituted at position 6 or 7 by an α,β-unsaturated carboxylic group terminating with said second reactive group;
(c) reacting said 4-(phenylamino)quinazoline substituted at position 6 or 7 by said α,β-unsaturated carboxylic group terminating with said second reactive group with a reactive substituted alkyl having 1–6 carbon atoms, so as to produce a 4-(phenylamino)quinazoline substituted at position 6 or 7 by said α,β-unsaturated carboxylic group terminating with said reactive substituted alkyl; and
(d) reacting said 4-(phenylamino)quinazoline substituted at position 6 or 7 by said α,β-unsaturated carboxylic group terminating with said reactive substituted alkyl with a carbon-11 labeled reactive compound.

71. The method of claim 70, wherein said X—Y(=O)-Z is at position 6 of the quinazoline ring.

72. The method of claim 70, wherein said reactive 4-(phenylamino)quinazoline is 4-(phenylamino)-6-nitroquinazoline, the method further comprising, prior to step (b):
(e) reducing said 4-(phenylamino)-6-nitroquinazoline so as to produce a 4-(phenylamino)-6-aminoquinazoline derivatized by said A, B, C and D.

73. The method of claim 70, wherein said second reactive group is halogen.

74. The method of claim 73, wherein said halogen is selected from the group consisting of bromine and iodine.

75. The method of claim 70, wherein said reactive α,β-unsaturated carboxylic derivative terminating with said second reactive group is 4-bromocrotonyl chloride.

76. The method of claim 70, wherein said reactive substituted alkyl having 1–6 carbon atoms is methylamine.

77. The method of claim 70, wherein said carbon-11 labeled reactive compound is carbon-11 methyl iodide.

78. The radiolabeled compound of claim 37, wherein said radioactive iodine is iodine-131.

79. A radiolabeled compound of a formula:

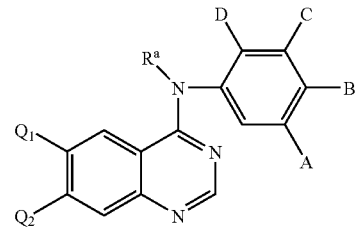

Formula I wherein:
Q1 is X—Y(=O)-Z and Q2 is selected from the group consisting of an alkoxy comprising a morpholino group and an alkylamino comprising a N-piperazinyl group, or
Q1 is selected from the group consisting of an alkoxy comprising a morpholino group and an alkylamino comprising a N-piperazinyl group, and Q2 is X—Y(=O)-Z;
X is selected from the group consisting of —NR¹—, —O—, —NH—NR¹—, —O—NR¹—, NH—CHR¹—, —CHR¹—NH—, —CHR¹—O—, —O—CHR¹—, —CHR¹—CH₂— and —CHR¹—S— or absent;
Y is selected from the group consisting of a non-radioactive carbon and a radioactive carbon;
Z is selected from the group consisting of —R²C=CHR³, —C≡C—R³ and —R²C=C=CHR³;
Rᵃ is selected from the group consisting of hydrogen or alkyl having 1–8 carbon atoms;
A, B, C and D are each independently selected from the group consisting of hydrogen, a non-radioactive derivatizing group, and a radioactive derivatizing group, whereas said non-radioactive group is selected from the group consisting of halogen, alkyl, haloalkyl, hydroxy, alkoxy, carboxy, carbalkoxy, thiocarboxy, thiohydroxy, thioalkoxy, alkylsulfinyl, alkylsulfonyl, amino, diamino, carbamyl, dicarbamoyl, nitro and cyano, and said radioactive derivatizing group is selected from a radioactive bromine, a radioactive iodine and a radioactive fluorine;

R¹ is selected from the group consisting of hydrogen, and substituted or non-substituted alkyl having 1–6 carbon atoms;

R² is selected from the group consisting of hydrogen, halogen and alkyl having 1–6 carbon atoms; and R³ is selected from the group consisting of hydrogen, halogen, carboxy, alkenyl, alkoxy, carbonyl, substituted or non-substituted alkyl having 1–6 carbon atoms and substituted or non-substituted phenyl;

provided that the compound comprises at least one radioactive atom.

80. The radiolabeled compound of claim 79, wherein Q1 is X—Y(═O)-Z and Q2 is said alkoxy comprising a morpholino group.

81. The radiolabeled compound of claim 79, wherein Q1 is X—Y(═O)-Z and Q2 is said alkylamino comprising a N-piperazinyl group.

82. The radiolabeled compound of claim 79, wherein X is said —NR¹— and Z is said —R²C═CHR³.

83. The radiolabeled compound of claim 82, wherein each of R¹, R², and R³ is hydrogen.

84. The radiolabeled compound of claim 82, wherein R³ is a substituted alkyl having 1–6 carbon atoms.

85. The radiolabeled compound of claim 84, wherein said substituted alkyl comprises a radioactive atom.

86. The radiolabeled compound of claim 79, wherein Y is said radioactive carbon.

87. The radiolabeled compound of claim 79, wherein at least one of A, B, C and D is said radioactive fluorine.

88. The radiolabeled compound of claim 79, wherein D is said radioactive fluorine.

89. The radiolabeled compound of claim 88, wherein A and B are each chlorine and C is hydrogen.

90. The radiolabeled compound of claim 79, wherein A is said radioactive bromine.

91. The radiolabeled compound of claim 79, wherein A is said radioactive iodine.

92. The radiolabeled compound of claim 79, wherein said radioactive carbon is carbon-11.

93. The radiolabeled compound of claim 92, wherein A and B are each chlorine, C is hydrogen and D is fluorine.

94. The radiolabeled compound of claim 92, wherein A is bromine or iodine and B, C and D are each hydrogen.

95. The radiolabeled compound of claim 86, wherein A and B are each chlorine, C is hydrogen and D is fluorine.

96. The radiolabeled compound of claim 86, wherein A is bromine or iodine and B, C and D are each hydrogen.

97. The radiolabeled compound of claim 86, wherein A and B are each chlorine, C is hydrogen and D is fluorine.

98. The radiolabeled compound of claim 86, wherein A is bromine or iodine and B, C and D are each hydrogen.

99. The radiolabeled compound of claim 79, wherein said, radioactive fluorine is fluorine-18.

100. The radiolabeled compound of claim 79, wherein said radioactive bromine is bromine-76 or bromine-77.

101. The radiolabeled compound of claim 79, wherein said radioactive iodine is iodine-123, iodine-124 or iodine-131.

102. The radiolabeled compound of claim 101, wherein said radioactive iodine is iodine-131.

103. The radiolabeled compound of claim 101, wherein said radioactive iodine is iodine-124.

104. The radiolabeled compound of claim 84, wherein Y is said radioactive carbon.

105. The radiolabeled compound of claim 104, wherein said radioactive carbon is carbon-11.

106. The radiolabeled compound of claim 105, wherein A and B are each chlorine, C is hydrogen and D is fluorine.

107. The radiolabeled compound of claim 105, wherein A is bromine or iodine and B, C and D are each hydrogen.

108. The radiolabeled compound of claim 84, wherein at least one of A, B, C and D is a radioactive atom selected from the group consisting of a radioactive fluorine, a radioactive bromine and a radioactive iodine.

109. A pharmaceutical composition comprising as an active ingredient the radiolabeled compound of claim 79, and a pharmaceutical acceptable carrier.

110. A method of monitoring the level of epidermal growth factor receptor within a body of a patient, the method comprising:

(a) administering to the patient the radiolabeled compound of claim 79; and (b) employing a nuclear imaging technique selected from the group comprising of positron emission tomography (PET) and single photon emission computed tomography (SPECT), for monitoring a distribution of the compound within the body or within a portion thereof.

111. A method of radiotherapy comprising administering to a patient a therapeutically effective amount of the radiolabeled compound of claim 79.

112. A method of synthesizing a radiolabeled compound of a formula:

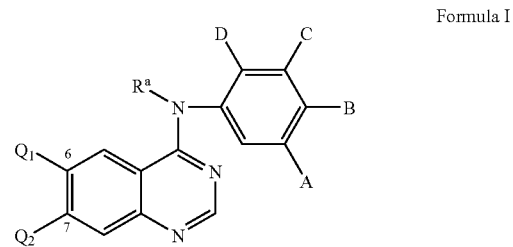

Formula I wherein:

Q1 is X—Y(═O)-Z and Q2 is selected from the group consisting of an alkoxy comprising a morpholino group and an alkylamino comprising a N-piperazinyl group, or Q1 is selected from the group consisting of an alkoxy comprising a morpholino group and an alkylamino comprising a N-piperazinyl group, and Q2 is X—Y(═O)-Z;

X is selected from the group consisting of —NR¹—, —O—, —NH—NR¹—, —O—NR¹—, NH—CHR¹—, —CHR¹—NH—, —CHR¹—O—, —O—CHR¹—, —CHR¹—CH₂— and —CHR¹—S— or absent;

Y is carbon-11;

Z is selected from the group consisting of —R²C═CHR³, —C≡C—R³ and —R²C═C═CHR³;

Rᵃ is selected from the group consisting of hydrogen or alkyl having 1–8 carbon atoms;

A, B, C and D are each independently selected from the group consisting of hydrogen and a non-radioactive derivatizing group selected from the group consisting of hydrogen, halogen, alkyl, haloalkyl, hydroxy, alkoxy, carboxy, carbalkoxy, thiocarboxy, thiohydroxy, thioalkoxy, alkylsulfinyl, alkylsulfonyl, amino, diamino, carbamyl, dicarbamoyl, nitro and cyano;

R[1] is selected from the group consisting of hydrogen and substituted or non-substituted alkyl having 1–6 carbon atoms;

R[2] is selected from the group consisting of hydrogen, halogen and alkyl having 1–6 carbon atoms; and R[3] is selected from the group consisting of hydrogen, halogen, carboxy, alkenyl, alkoxy, carbonyl, substituted or non-substituted alkyl having 1–6 carbon atoms and substituted or non-substituted phenyl, the method comprising:
  (a) coupling an aniline derivatized by said R[a], A, B, C and D with a 4-chloroquinazoline substituted at position 6 and 7 by a first and a second reactive group, so as to produce a reactive 4-(phenylamino)quinazoline derivatized by said A, B, C and D;
  (b) reacting said reactive 4-(phenylamino)quinazoline with a chemically reactive group, said chemically reactive group comprises said morpholinoalkoxy group or said N-piperazinyl group, so as to produce a reactive fluorine-18 labeled 4-(phenylamino)quinazoline derivatized by said A, B, C and D and substituted by said group; and
  (c) reacting said reactive 4-(phenylamino)quinazoline substituted by said group with a reactive carbon-11 labeled α,β-unsaturated carboxylic derivative.

113. The method of claim 112, wherein said X—Y(=O)-Z is at position 6 of the quinazoline ring.

114. The method of claim 112, wherein said reactive 4-(phenylamino)quinazoline is 4-(phenylamino)-6-nitroquinazoline, the method further comprising, prior to step (b):
  (d) reducing said 4-(phenylamino)-6-nitroquinazoline so as to produce a 4-(phenylamino)-6-aminoquinazoline derivatized by said A, B, C and D.

115. The method of claim 112, wherein said chemically reactive group comprises a morpholinoalkoxy group.

116. The method of claim 112, wherein said reactive carbon-11 labeled α,β-unsaturated carboxylic derivative is carbon-11 labeled acryloyl chloride.

117. A method of synthesizing a radiolabeled compound of a formula:

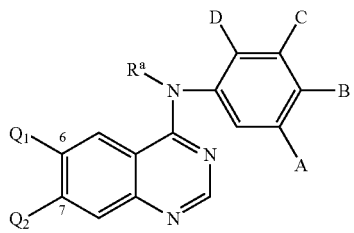

Formula I wherein:

Q1 is X—Y(=O)-Z and Q2 is selected from the group consisting of an alkoxy comprising a morpholino group and an alkylamino comprising a N-piperazinyl group, or Q1 is selected from the group consisting of an alkoxy comprising a morpholino group and an alkylamino comprising a N-piperazinyl group, and Q2 is X—Y(=O)-Z;

X is selected from the group consisting of —NR[1]—, —O—, —NH—NR[1]—, —O—NR[1]—, NH—CHR[1]—, —CHR[1]—NH—, —CHR[1]—O—, —O—CHR[1]—, —CHR[1]—CH$_2$— and —CHR[1]—S— or absent;

Y is a non-radioactive carbon;

Z is selected from the group consisting of —R[2]C=CHR[3], —C≡C—R[3] and —R[2]C=C=CHR[3];

R[a] is selected from the group consisting of hydrogen or alkyl having 1–8 carbon atoms;

A, B, C and D are each independently selected from the group consisting of hydrogen, a non-radioactive derivatizing group, and a fluorine-18, whereas said non-radioactive derivatizing group is selected from the group consisting of hydrogen, halogen, alkyl, haloalkyl, hydroxy, alkoxy, carboxy, carbalkoxy, thiocarboxy, thiohydroxy, thioalkoxy, alkylsulfinyl, alkylsulfonyl, amino, diamino, carbamyl, dicarbamoyl, nitro and cyano, provided that at least one of A, B, C and D is said fluorine-18;

R[1] is selected from the group consisting of hydrogen, and substituted or non-substituted alkyl having 1–6 carbon atoms;

R[2] is selected from the group consisting of hydrogen, halogen and alkyl having 1–6 carbon atoms; and R[3] is selected from the group consisting of hydrogen, halogen, carboxy, alkenyl, alkoxy, carbonyl, substituted or non-substituted alkyl having 1–6 carbon atoms and substituted or non-substituted phenyl, the method comprising:
  (a) preparing a fluorine-18 labeled aniline derivatized by said R[a], A, B, C and D, wherein at least one of A, B, C and D is said fluorine-18;
  (b) coupling said fluorine-18 labeled aniline derivatized by said R[a], A, B, C and D with 4-chloroquinazoline substituted at position 6 and 7 by a first and a second reactive group, so as to produce a reactive fluorine-18 labeled 4-(phenylamino)quinazoline derivatized by said A, B, C and D;
  (c) reacting said reactive fluorine-18 labeled 4-(phenylamino)quinazoline with a chemically reactive group, said chemically reactive group comprises morpholinoalkoxy group or said N-piperazinyl group, so as to produce a reactive fluorine-18 labeled 4-(phenylamino)quinazoline derivatized by said A, B, C and D and substituted by said group; and
  (d) reacting said reactive fluorine-18 labeled 4-(phenylamino)quinazoline substituted by said group with a reactive α,β-unsaturated carboxylic derivative.

118. The method of claim 117, wherein said X—Y(=O)-Z is at position 6 of the quinazoline ring.

119. The method of claim 117, wherein said reactive fluorine-18 labeled 4-(phenylamino)quinazoline is fluorine-18 labeled 4-(phenylamino)-6-nitroquinazoline, the method further comprising, prior to step (c):
  (e) reducing said fluorine-18 labeled 4-(phenylamino)-6-nitroquinazoline, so as to produce a fluorine-18 labeled 4-(phenylamino)-6-aminoquinazoline derivatized by said A, B, C and D.

120. The method of claim 117, wherein said reactive α,β-unsaturated carboxylic derivative is acryloyl chloride.

121. A method of synthesizing a radiolabeled compound of a formula:

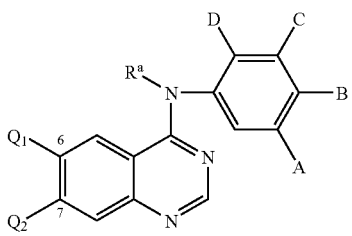

Formula I wherein:
Q1 is X—Y(=O)-Z and Q2 is selected from the group consisting of an alkoxy comprising a morpholino group and an alkylamino comprising a N-piperazinyl group, or Q1 is selected from the group consisting of an alkoxy comprising a morpholino group and an alkylamino comprising a N-piperazinyl group, and Q2 is X—Y(=O)-Z;

X is selected from the group consisting of —$NR^1$—, —O—, —NH—$NR^1$—, —O—$NR^1$—, NH—$CHR^1$—, —$CHR^1$—NH—, —$CHR^1$—O—, —O—$CHR^1$—, —$CHR^1$—$CH_2$— and —$CHR^1$—S— or absent;

Y is a non-radioactive carbon;

Z is selected from the group consisting of —$R^2C$=$CHR^3$, —C≡C—$R^3$ and —$R^2C$=C=$CHR^3$;

$R^a$ is selected from the group consisting of hydrogen or alkyl having 1–8 carbon atoms;

A, B, C and D are each independently selected from the group consisting of hydrogen, a non-radioactive derivatizing group and a radioactive atom, whereas said non-radioactive group is selected from the group consisting of halogen, alkyl, haloalkyl, hydroxy, alkoxy, carboxy, carbalkoxy, thiocarboxy, thiohydroxy, thioalkoxy, alkylsulfinyl, alkylsulfonyl, amino, diamino, carbamyl, dicarbamoyl, nitro and cyano, and said radioactive derivatizing group is selected from a radioactive bromine and a radioactive iodine, provided that at least one of A, B, C and D is said radioactive bromine or said radioactive iodine;

$R^1$ is selected from the group consisting of hydrogen, and substituted or non-substituted alkyl having 1–6 carbon atoms;

$R^2$ is selected from the group consisting of hydrogen, halogen and alkyl having 1–6 carbon atoms; and $R^3$ is selected from the group consisting of hydrogen, halogen, carboxy, alkenyl, alkoxy, carbonyl, substituted or non-substituted alkyl having 1–6 carbon atoms and substituted or non-substituted phenyl, which comprises a substituted amino group, the method comprising:

(a) coupling an aniline derivatized by said $R^a$, A, B, C and D, wherein at least one of A, B, C and D is a halogen, with a 4-chloroquinazoline substituted at position 6 and 7 by a first and a second reactive group, so as to produce a reactive 4-(phenylamino)quinazoline derivatized by said A, B, C and D, wherein at least one of A, B, C and D is said halogen;

(b) radiolabeling said reactive 4-(phenylamino)quinazoline derivatized by said A, B, C and D with a radioactive bromine or a radioactive iodine, so as to produce a radioactive bromine labeled or a radioactive iodine labeled reactive 4-(phenylamino)quinazoline derivatized by said A, B, C and D, wherein at least one of said A, B, C and D is said radioactive bromine or said radioactive iodine;

(c) reacting said reactive radioactive bromine labeled or radioactive iodine labeled 4-(phenylamino)quinazoline with a chemically reactive group, said chemically reactive group comprises morpholinoalkoxy group or said N-piperazinyl group, so as to produce a reactive fluorine-18 labeled 4-(phenylamino)quinazoline derivatized by said A, B, C and D and substituted by said group; and (d) reacting said radioactive bromine labeled or radioactive iodine labeled reactive 4-(phenylamino)quinazoline substituted by said group with a reactive α,β-unsaturated carboxylic derivative.

122. The method of claim 121, wherein said radioactive bromine is bromine-76 or bromine-77.

123. The method of claim 121, wherein said radioactive iodine is iodine-123, iodine-124 or iodine-131.

124. The method of claim 121, wherein said X—Y(=O)-Z is at position 6 of the quinazoline ring.

125. The method of claim 121, wherein said reactive 4-(phenylamino)quinazoline is 4-(phenylamino)-6-nitroquinazoline, the method further comprising, prior to step (b):

(e) reducing said 4-(phenylamino)-6-nitroquinazoline, so as to produce a 4-(phenylamino)-6-aminoquinazoline derivatized by said A, B, C and D, wherein at least one of said A, B, C and D is said halogen.

126. The method of claim 121, wherein said halogen is bromine.

127. The method of claim 121, wherein said reactive α,β-unsaturated carboxylic derivative is acryloyl chloride.

128. A method of synthesizing a radiolabeled compound of a formula:

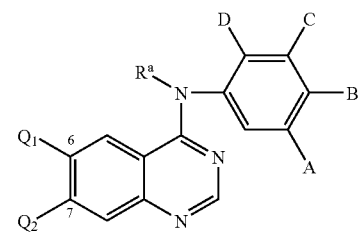

Formula I wherein:
Q1 is X—Y(=O)-Z and Q2 is selected from the group consisting of an alkoxy comprising a morpholino group and an alkylamino comprising a N-piperazinyl group, or Q1 is selected from the group consisting of an alkoxy comprising a morpholino group and an alkylamino comprising a N-piperazinyl group, and Q2 is X—Y(=O)-Z;

X is selected from the group consisting of —$NR^1$—, —O—, —NH—$NR^1$—, —O—$NR^1$—, NH—$CHR^1$—, —$CHR^1$—NH—, —$CHR^1$—O—, —O—$CHR^1$—, —$CHR^1$—$CH_2$— and —$CHR^1$—S— or absent;

Y is a non-radioactive carbon;

Z is selected from the group consisting of —$R^2C$=$CHR^3$, —C≡C—$R^3$ and —$R^2C$=C=$CHR^3$;

$R^a$ is selected from the group consisting of hydrogen or alkyl having 1–8 carbon atoms;

A, B, C and D are each independently selected from the group consisting of hydrogen and a non-radioactive derivatizing group selected from the group consisting of hydrogen, halogen, alkyl, haloalkyl, hydroxy, alkoxy, carboxy, carbalkoxy, thiocarboxy, thiohydroxy, thioalkoxy, alkylsulfinyl, alkylsulfonyl, amino, diamino, carbamyl, dicarbamoyl, nitro and cyano;

$R^1$ is selected from the group consisting of hydrogen, and substituted or non-substituted alkyl having 1–6 carbon atoms;

$R^2$ is selected from the group consisting of hydrogen, halogen and alkyl having 1–6 carbon atoms; and $R^3$ is a substituted alkyl having 1–6 carbon atoms, said substituted alkyl comprising a carbon-11 atom, the method comprising:

(a) coupling an aniline derivatized by said $R^a$, A, B, C and D with a 4-chloroquinazoline substituted at position 6 and 7 by a first and a second reactive group, so as to produce a reactive 4-(phenylamino) quinazoline derivatized by said A, B, C and D;

(b) reacting said reactive 4-(phenylamino)quinazoline with a chemically reactive group, said chemically reactive group comprises morpholinoalkoxy group or said N-piperazinyl group, so as to produce a reactive fluorine-18 labeled 4-(phenylamino) quinazoline derivatized by said A, B, C and D and substituted by said group;

(c) reacting said reactive 4-(phenylamino)quinazoline with a reactive α,β-unsaturated carboxylic derivative, said reactive α,β-unsaturated carboxylic derivative terminating with a third reactive group, so as to produce a 4-(phenylamino)quinazoline substituted at position 6 or 7 by an α,β-unsaturated carboxylic group terminating with said second reactive group;

(d) reacting said 4-(phenylamino)quinazoline substituted at position 6 or 7 by said α,β-unsaturated carboxylic group terminating with said third reactive group with a reactive substituted alkyl having 1–6 carbon atoms, so as to produce a 4-(phenylamino) quinazoline substituted at position 6 or 7 by said α,β-unsaturated carboxylic group terminating with said reactive substituted alkyl; and (e) reacting said 4-(phenylamino)quinazoline substituted at position 6 or 7 by said α,β-unsaturated carboxylic group terminating with said reactive substituted alkyl with a carbon-11 labeled reactive compound.

129. The method of claim 128, wherein said X—Y (=O)-Z is at position 6 of the quinazoline ring.

130. The method of claim 128, wherein said reactive 4-(phenylamino)quinazoline is 4-(phenylamino)-6-nitroquinazoline, the method further comprising, prior to step (b):

(e) reducing said 4-(phenylamino)-6-nitroquinazoline so as to produce a 4-(phenylamino)-6-aminoquinazoline derivatized by said A, B, C and D.

131. The method of claim 128, wherein said third reactive group is halogen.

132. The method of claim 131, wherein said halogen is selected from the group consisting of bromine and iodine.

133. The method of claim 128, wherein said reactive α,β-unsaturated carboxylic derivative terminating with said third reactive group is 4-bromocrotonyl chloride.

134. The method of claim 128, wherein said reactive substituted alkyl having 1–6 carbon atoms is methylamine.

135. The method of claim 128, wherein said carbon-11 labeled reactive compound is carbon-11 methyl iodide.

\* \* \* \* \*